(12) United States Patent
Kotra et al.

(10) Patent No.: US 10,716,791 B2
(45) Date of Patent: Jul. 21, 2020

(54) INHIBITORS OF PEPTIDYL ARGININE DEIMINASE (PAD) ENZYMES AND USES THEREOF

(71) Applicant: UNIVERSITY HEALTH NETWORK, Toronto (CA)

(72) Inventors: Lakshmi P. Kotra, Toronto (CA); Ewa Wasilewski, Etobicoke (CA)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 15/753,208

(22) PCT Filed: Aug. 15, 2016

(86) PCT No.: PCT/CA2016/050958
§ 371 (c)(1),
(2) Date: Feb. 16, 2018

(87) PCT Pub. No.: WO2017/027967
PCT Pub. Date: Feb. 23, 2017

(65) Prior Publication Data
US 2018/0250307 A1 Sep. 6, 2018

Related U.S. Application Data

(60) Provisional application No. 62/205,939, filed on Aug. 17, 2015.

(51) Int. Cl.
| | | |
|---|---|---|
| *A61K 31/5377* | (2006.01) |
| *A61K 31/4178* | (2006.01) |
| *A61K 31/4192* | (2006.01) |
| *A61K 31/496* | (2006.01) |
| *C07D 295/185* | (2006.01) |
| *C07D 403/12* | (2006.01) |
| *C07D 405/12* | (2006.01) |
| *C07D 307/68* | (2006.01) |
| *C07D 413/12* | (2006.01) |
| *C07D 233/90* | (2006.01) |
| *C07D 295/15* | (2006.01) |
| *C07D 249/02* | (2006.01) |
| *A61P 25/00* | (2006.01) |
| *A61P 19/00* | (2006.01) |
| *A61P 17/00* | (2006.01) |

(52) U.S. Cl.
CPC ...... *A61K 31/5377* (2013.01); *A61K 31/4178* (2013.01); *A61K 31/4192* (2013.01); *A61K 31/496* (2013.01); *A61P 17/00* (2018.01); *A61P 19/00* (2018.01); *A61P 25/00* (2018.01); *C07D 233/90* (2013.01); *C07D 249/02* (2013.01); *C07D 295/15* (2013.01); *C07D 295/185* (2013.01); *C07D 307/68* (2013.01); *C07D 403/12* (2013.01); *C07D 405/12* (2013.01); *C07D 413/12* (2013.01)

(58) Field of Classification Search
None
See application file for complete search history.

(56) References Cited

U.S. PATENT DOCUMENTS

| | | |
|---|---|---|
| 4,766,110 A | 8/1988 | Ryan et al. |
| 4,818,748 A | 4/1989 | Bender et al. |
| 5,223,516 A | 6/1993 | Delaney et al. |
| 5,955,576 A | 9/1999 | Vlasuk et al. |
| 7,371,743 B2 | 5/2008 | Priepke et al. |
| 2012/0108562 A1 | 5/2012 | Chen et al. |

FOREIGN PATENT DOCUMENTS

| | | | |
|---|---|---|---|
| DE | 2755036 A1 * | 6/1978 | .......... C07D 207/16 |
| WO | WO 92/22313 | 12/1992 | |
| WO | WO 00/23421 | 4/2000 | |
| WO | WO 2014/019092 | 2/2014 | |

OTHER PUBLICATIONS

Chang et al J. Med. Chem. (1971) 14(6), 484-487. (Year: 1971).*
Morier et al. International Journal of Peptide & Protein Research (1981), 18(5), 513-515. (Year: 1981).*
Morier et al. European Journal of Medicine Chem. (1979), 14(5), 425-433. (Year: 1979).*
Ito, Nobuyuki. Cancer Science 94(1), (2003) 3-8.*
Monasoon, Olivier. Straightforward glycosylation of alcohols and amino acids mediated by ionic liquid. Carbohydrate Research. 352 (2012) 202-205.*
Database Registry Chemical Abstracts Service, Columbus, Ohio, Accession No. RN 1487909-43-2, Entered STN: Dec. 5, 2013.*
Popescu, B. F.; Lucchinetti, C. F. Pathology of demyelinating diseases. Annu. Rev. Pathol. 2012, 7, 185-217.
Dutta, R.; Trapp, B. D. Pathogenesis of axonal and neuronal damage in multiple sclerosis. Neurology 2007, 68(2), S22-S31.
Noseworthy, J.H. Progress in determining the causes and treatment of multiple sclerosis. Nature 1999, 399, A40-A47.
Moscarello, M. A. et al. Inhibition of peptidyl-arginine deiminases reverses protein-hypercitrullination and disease in mouse models of multiple sclerosis. Dis. Model. Mech. 2013, 6, 467-478.

(Continued)

*Primary Examiner* — Samantha L Shterengarts
(74) *Attorney, Agent, or Firm* — Bereskin & Parr/S.E.N.C.R.L., s.r.l.; Michael Fenwick

(57) ABSTRACT

The present application relates to a-substituted amino acid compounds of the Formula (I), compositions comprising these compounds and their use, in particular for the treatment of diseases, disorders or conditions characterized by or associated with the hypercitrullination of proteins by peptidyl arginine deiminase (PAD) enzymes.

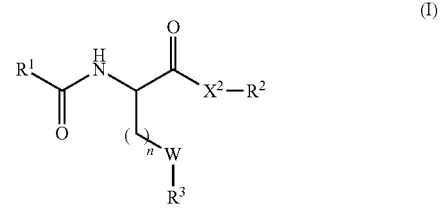

(I)

4 Claims, 13 Drawing Sheets

(56) References Cited

OTHER PUBLICATIONS

Hashim, G.A.; Wood, D.D.; Moscarello, M.A. Myelin lipophilin induced demyelinating diseases of the central nervous system. Neurochem. Res. 1980, 5, 1117-1115.

Sospedra, M.; Martin, R. Immunology of multiple sclerosis. Annu. Rev. Immunol. 2005, 23, 683-747.

Lebar, R.; Lubetzki, C.; Vincent, C.; Lombrail, P.; Boutry, J.M. The M2 autoantigen of central nervous system myelin, a glycoprotein present in oligodendrocyte membrane. Clin. Exp. Immunol. 1986, 66(2), 423-434.

Bahreini, S.A.; Jabalameli, M.R.; Saadatnia, M.; Zahednasab, H. The role of non-HLA single nucleotide polymorphisms in multiple sclerosis susceptibility. J. Neuroimmunol. 2010, 229, 5-15.

Steinman, L.; Zamvil, S.S. Multiple sclerosis in need of a critical reappraisal. Med. Hypothesis. 2006, 54, 99-106.

Lopez-Diego, R. S.; Weiner, H. L. Novel therapeutic strategies for multiple sclerosis—a multifaceted adversary. Nature Rev. Drug Discov. 2008, 7, 909-925.

Weinstock-Guttman, B.; Jacobs, L. D. What is new in the treatment of multiple sclerosis. Drugs 2000, 59, 401-410.

Quirke, A.M.; Fisher, B.A.; Kinloch, A.J.; Venables, P.J. Citrullination of autoantigens: upstream of TNFα in the pathogenesis of rheumatoid arthritis. FEBS Lett. 2011, 585(23), 3681-3688.

Lange, S.; Gögel, S.; Leung, K.Y.; Vernay, B.; Nicholas, A.P.; Causey, C.P.; Thompson, P.R.; Greene, N.D.; Ferretti, P. Protein deiminases: new players in the developmentally regulated loss of neural regenerative ability. Dev. Biol. 2011, 355(2), 205-214.

Kidd, B.A.; Ho, P.P.; Sharpe, O.; Zhao, X.; Tomooka, B.H.; Kanter, J.L.; Steinman, L.; Robinson, W.H. Epitope spreading to citrullinated antigens in mouse models of autoimmune arthritis and demyelination. Arthritis Res. Ther. 2008, 10, R119.

Harauz, G.; Musse, A.A. A tale of two citrullines—structural and functional aspects of myelin basic protein deimination in health and disease. Neurochem. Res. 2007, 32, 137-158.

Moscarello, M.A.; Wood, D.D.; Ackerley, C.; Boulias, C. Myelin in multiple sclerosis is developmentally immature. J. Clin. Invest. 1994, 94, 146-154.

Wood, D.D.; Bilbao, J.M.; O'Connors, P.; Moscarello, M.A. Acute multiple sclerosis (Marburg type) is associated with developmentally immature myelin basic protein. Ann. Neurol. 1996, 40, 18-24.

Brady, G.W.; Fein, D.B.; Wood, D.D.; Moscarello, M.A. The interaction of basic proteins from normal and multiple sclerosis myelin with phosphatidylglycerol vesicles. FEBS Lett. 1981, 125, 159-160.

Brady, G.W.; Murthy, N.S.; Fein, D.B.; Wood, D.D.; Moscarello, M.A. The effect of basic myelin protein on multilayer membrane formation. Biophys. J. 1981, 34(2), 345-350.

Boggs, J.M.; Wood, D.D.; Moscarello, M.A. Hydrophobic and electrostatic interactions of myelin basic proteins with lipid. Participation of N-terminal and C-terminal portions. Biochemistry 1981, 20(5), 1065-1073.

Epand, R.M.; Moscarello, M.A.; Zierenberg, B.; Vail, W.J. The folded conformation of the encephalitogenic protein of the human brain. Biochemistry 1974, 13, 1264-1267.

Deber, C.M.; Hughes, D.W.; Fraser, P.E.; Pawagi, A.B.; Moscarello, M.A. Binding of human normal and multiple sclerosis-derived myelin basic protein to phospholipid vesicles: effects on membrane head group and bilayer regions. Arch. Biochem. Biophys. 1986, 245(2), 455-463.

Carrillo-Vico, A.; Leech, M.D.; Anderton, S.M. Contribution of myelin autoantigen citrullination to T cell autoaggression in the central nervous system. J. Immunol. 2010, 184 (6), 2839-2846.

Raijmakers, R.; Vogelzangs, J.; Croxford, J.L.; Wesseling, P.; van Venrooij, W.J.; Pruijn, G.J. Citrullination of central nervous system proteins during the development of experimental autoimmune encephalomyelitis. J. Comp. Neurol. 2005, 486(3), 243-253.

Gyorgy, B.; Toth, E.; Tarcsa, E.; Falus, A.; Buzas, E. I. Citrullination: a posttranslational modification in health and disease. Int. J. Biochem. Cell. Biol. 2006, 38 (10), 1662-1677.

Curis, E.; Nicolis, I.; Moinard, C.; Osowska, S.; Zerrouk, N.; Benazeth, S.; Cynober, L. Almost all about citrulline in mammals. Amino Acids 2005, 29 (3), 177-205.

Vossenaar, E.R.; Zendman, A.J.; van Venrooij, W.J.; Pruijn, G.J. Pad, a growing family of citrullinating enzymes: genes, features and involvement in disease. Bioessays 2003, 25(11), 1106-1118.

Anzilotti, C.; Pratesi, F.; Tommasi, C.; Migliorini, P. Peptidylarginine deiminase 4 and citrullination in health and disease. Autoimmun Rev. 2010, 9(3), 158-160.

Jiang, H., Zhang, Sheng-Le, Pernis, Benvenuto. T Cells in Murine Experimental Allergic Encephalomyelitis. Science, 256:1212-1215, 1992.

Chirivi, R. G. S.; van Rosmale, J. W. G.; Jenniskens, G. J.; Pruijn, G. J.; Raats, J. M.-H. itrullination: A trget for disease intervention in multiple sclerosis and other inflammatory disorders. J. Clin. Cell. Immunol. 2-13, 4, 3.

Musse, A.A.; Harauz, G. Molecular "negativity" may underlie multiple sclerosis: role of the myelin basic protein family in the pathogenesis of MS. Int. Rev. Neurobiol. 2007, 79, 149-172.

Deraos, G.; Chatzantoni, K.; Matsoukas, M.T.; Tselios, T.; Deraos, S.; Katsara, M.; Papathanasopoulos, P.; Vynios, D.; Apostolopoulos, V.; Mouzaki, A.; Matsoukas, J. Citrullination of linear and cyclic altered peptide ligands from myelin basic protein (MBP(87-99)) epitope elicits a Th1 polarized response by T cells isolated from multiple sclerosis patients: implications in triggering disease. J. Med. Chem. 2008, 51(24), 7834-7842.

Moscarello, M. A.; Lei, H.; Mastronardi, F. G.; Winer, S.; Tsui, H.; Li, Z.; Ackerley, C.; Zhang, L.; Raijmakers, R.; Wood, D. D. Inhibition of peptidyl-arginine deiminases reverses protein-hypercitrullination and disease in mouse models of multiple sclerosis. Dis. Model. Mech. 2013, 6(2), 467-478.

Suzuki, A.; Yamada, R.; Yamamoto, K. Citrullination by Peptidylarginine Deiminase in Rheumatoid Arthritis. Ann. N.Y. Acad. Sci. 2007, 1108, 323-339.

Arita, K.; Hashimoto, H.; Shimizu, T.; Nakashima, K.; Yamada, M.; Sato, M. Structural basis for Ca(2+)-induced activation of human PAD4. Nature Struct. Mol. Biol. 2004, 11, 777-783.

Knuckley, B.; Luo, Y.; Thomson, P. R. Profiling protein arginine deiminase 4 (PAD4): A novel screen to identify PAD4 inhibitors. Bioorg. Med. Chem. 2008, 16(2), 739-745.

Luo, Y.; Knuckley, B.; Lee, Y. H.; Stallcup, M. R.; Thomson, P. R. A fluoroacetamidine-based inactivator of protein arginine deiminase 4: design, synthesis, and in vitro and in vivo evaluation. J. Am. Chem. Soc. 2006, 128, 1092-1093.

Bello, A. M.; Poduch, E.; Wei, L.; Moscarello, M.; Kotra, L. P. Interrogation of the active site of protein arginine deiminase (PAD) using designer probes. ACS Med. Chem. Lett. 2013, 4 (2), 249-253.

Ishigami, A. et al. Importance of research on peptidylarginine deiminase and citrullinated proteins in age-related disease. Geriatr. Gerontol. Int. 2010, 10 Suppl. 1, S53-S58.

Gould, R. M. et al. Messenger RNAs located in myelin sheath assembly sites. J. Neurochem. 2000, 75, 1834-1844.

Moscarello, M. A. et al. Peptidylarginine deiminase: a candidate factor in demyelinating disease. J. Neurochem. 2002, 81, 335-343.

Bartzokis, G. Age-related myelin breakdown: a developmental model of cognitive decline and Alzheimer's disease. Neurobiol. Aging 2004, 25, 5-18.

Tian, J. et al. Relationships between arteriosclerosis, cerebral amyloid angiopathy and myelin loss from cerebral cortical white matter in Alzheimer's disease. Neuropathol. Appl. Neurobiol. 2004, 30, 46-56.

Asaga, H. et al. Protein deimination in the rat brain: generation of citulline-containing proteins in cerebrum perfused with oxygen-deprived media. Biomed. Res. 2000, 21, 197-205.

Asaga, H. et al. Protein deimination in the rat brain after kainite administration: citulline-containing proteins as a novel marker of neurodegeneration. Neurosci. Lett. 2001, 299, 5-8.

Asaga, H. et al. Increased and type II specific expression of peptidylarginine deiminase in activated-microglia but not hyperplastic astrocytes following kainic acid-evoked neurodegeration in the rat brain. Neurosci. Lett. 2002, 326, 129-132.

Shimada, N. et al. Developmental and age-related changes of peptidylarginine deiminase 2 in the mouse brain. J. Neurosci. Res. 2010, 88, 798-806.

(56) References Cited

OTHER PUBLICATIONS

Wei, L. et al. Novel Inhibitors of Protein Arginine Deiminase with Potential Activity in Multiple Sclerosis Animal Model. J. Med. Chem. 2013, 56 (4), 1715-1722.

Acharya, N. K. et al. Neuronal PAD4 expression and protein citrullination: possible role in production of autoantibodies associated with neurodegenerative disease. J. Autoimmun. 2012, 38, 369-380.

Ishigami, A. et al. Abnormal accumulation of citullinated proteins catalyzed by peptidylarginine deiminase in hippocampal extracts from patients with Alzheimer's disease. J. Neurosci. Res. 2005, 80, 120-128.

Akiyama, K. et al. Localization of peptidylarginine deiminase type II in a stage-specific immature oligodendrocyte from rat cerebral hemisphere. Neurosci. Lett. 1999, 274, 53-55.

Lamensa JWE, Moscarello MA. Deimination of Human Myelin Basic Protein by a Peptidylarginine Deiminase from Bovine Brain. J Neurochem 1993; 61: 987-996.

Sambandam T, Belousova M, Accaviti-Lope MA, Blanquicett C, Geurcello V, Raijmakers R, Nicholas AP. Increased peptidylarginine deiminase type II in hypoxic astrocytes. Biochem Biophys Res Commun 2004; 325: 1324-1329.

Guerrin M, Ishigami A, Mechin M-C, Nachat R, Valmary S, Sebbag M, Simon M, Senshu T, Serre G. cDNA cloning, gene organization and expression analysis of human peptidylarginine deiminase type I. Biochem J. 2003, 370, 167-174.

Akiyama K, Inoue K, Senshu T. Immunocytochemical demonstration of skeletal muscle type peptidylarginine deiminase in various rat tissues. Cell Biol Int Rep 1990; 14: 267-273.

Dekan, Z.; Vetter, I.; Daly, N. L.; Craik, D. J.; Lewis, R. J.; Alewood, P. F. alpha-Conotoxin ImI incorporating stable cystathionine bridges maintains full potency and identical three dimensional structure. J. Am. Chem. Soc. 2011, 133, 15866-15869.

Nakamura, T.; Noguchi, T.; Kobayashi, H.; Miyachi, H.; Hashimoto, Y. Mono- and dihydroxylated metabolites of thalidomide: synthesis and TNF-alpha production inhibitory activity. Chem. Pharm. Bull. (Tokyo) 2006, 54, 1709-1714.

Fujisaki, F.; Toyofuki, K.; Egami, M.; Ishida S.; Nakamoto, N.; Kashige, N.; Miake, F.; and Sumoto, K. Antibacterial Activity of Some 5-Dialkylaminomethylhydantoins and Related Derivatives. Chem. Pharm. Bull 61(10):1090-1093, 2013.

Sureshbabu, V.V.; Venkataramanarao, R.; Naik, S.A.; Chennakrishnareddy, G. Synthesis of Tetrazole Analogues of Amino Acids Using Fmoc Chemistry: Isolation of Amino Free Tetrazoles and Their Incorpration into Peptides. Tetrahedron Letters. 48:7038-7041, 2007.

Perez, M. and Pleixats, R. FeCl3-Catalyzed Conjugate Addition of Secondary Amines, Imidazole and Pyrazole to Methyl 2-Acetamidoacrylate. Preparation of beta-Dialkylamino-alpha-alamine and beta-(N-heteroaryl)-alpha-alanine Derivatives. Tetrahedron. 51(30):8355-8362, 1995.

Knuckley, B.; Luo, Y. and Thompson, P.R. Profiling Protein Arginine Deiminase 4 (PAD4): A Novel Screen to Identify PAD4 Inhibitors. Bioorganic & Medicinal Chemistry 16:739-745, 2008.

Database CAS Registry: Registry No. (Entry Date): 935779-65-0 (2007), 170305-13-2 (1995).

Database CAS Registry: Registry No. (Entry Date): 86938 (1984).

Database CAS Registry: Registry No. (Entry Date): 1487909-43-2 (May 12, 2013).

Database CAS Registry: Registry No. (Entry Date): 1609202-52-9 (2013); 171514-07-1, 1427556-98-6, 1427556-99-7 (2012); 1310039-76-9 (2011); 1043452-31-8, 90035-60-2 (2010_; 1236069-69-4 (2009); 849411-41-2 (2005); 169498-38-8 (1995).

Database CAS Registry: Registry No. (Entry Date): 331755-10-3 (2001); 30134-53-3, 197892-55-0 (1999); 204767-38-4 (1998); 188067-47-2 (1997); 4909-53-9 (1996); 150716-05-5 (1993).

Database CAS Registry: Registry No. (Entry Date): 1822161-62-5 (Mar. 12, 2015), 1822161-63-6 (Mar. 12, 2015).

* cited by examiner

| Treatment | PAD2 Staining | Citrulline Staining | Results |
|---|---|---|---|
| Healthy mice |  |  | Normal PAD2 and citrullination levels. |
| PBS treatment |  |  | Higher amount of PAD2 and citrulline |
| KP-302 treatment |  |  | Much reduced levels of PAD2 and citrulline |
| KP-305 treatment |  |  | Much reduced levels of PAD2 and citrulline |

INHIBITORS OF PEPTIDYL ARGININE DEIMINASE (PAD) ENZYMES AND USES THEREOF

CROSS REFERENCE TO RELATED APPLICATIONS

This is a national stage application of PCT/CA2016/050958, filed Aug. 15, 2016, which claims priority from U.S. Provisional patent application Ser. No. 62/205,939, filed Aug. 17, 2015, all of which are incorporated herein by reference in their entirety.

FIELD

The present application relates to α-substituted amino acid compounds, compositions comprising these compounds and their use, in particular for the treatment of diseases, disorders or conditions characterized by or associated with the hypercitrullination of proteins by peptidyl arginine deiminase (PAD) enzymes.

BACKGROUND

Demyelination and Multiple Sclerosis.

Demyelination is a neuropathological state where the insulating myelin sheath on the axons of the neurons is degraded, the pathogenesis of which could be due to a variety of causes.[1] Multiple sclerosis (MS), one such clinical condition, is a chronic and most common demyelinating disease, affecting about 2.2 million people worldwide.[2] It is characterized by a patchy degradation of myelin on the axons, known as demyelinated lesions, and the healing of these patches occurs via scar formation called plaques.

A variety of causes such as genetic, immunological and environmental factors are suggested to play a role leading to this condition.[3] The most common theory is the autoimmune theory which postulates that sensitization of T cells in the periphery leads to their travel through a disrupted blood brain barrier to attack and destroy myelin.[4] Several CNS proteins have been shown to induce this condition, including myelin proteolipid protein (PLP),[5] myelin-associated glycoprotein (MAG),[6] myelin oligodendrocyte glycoprotein (MOG),[7] transaldolase and S100.[6] Genetic studies indicate the involvement of about 30 single nucleotide polymorphisms (SNPs), although it remains to be seen as to the relevance of these SNPs for MS therapeutics development.[8]

Current MS therapies reduce the frequency of relapses but do not delay the progression of the disease nor do they reverse the destruction of myelin.[9,10,11] The most popular treatment is Copaxone™ (also known as Copolymer-1, Cop-1, or Glatiramer acetate), marketed by Teva Pharmaceuticals. This is an immunomodulator drug and is a random polymer of four amino acids-glutamic acid, lysine, alanine and tyrosine—in the same proportion found in myelin basic protein (MBP).

Currently, there is a need for novel mechanisms of preventing and potentially reversing demyelination, such that the treatment options for demyelinating diseases such as multiple sclerosis can be conceived with better safety profiles and with clear molecular mechanisms of action.

Citrullination and Demyelination.

In general, immunological self-tolerance is an important defense against many autoimmune diseases and its breakdown in the body leads to various autoimmune diseases. This primarily arises from the immune recognition of self-proteins that have undergone post-translational modifications under pathophysiological conditions that would not happen under normal circumstances.

Citrullination, a post-translational event, in general is involved in many cellular processes such as gene regulation, embryonic development and differentiation.[12,13] Lately, the abnormal role of (hyper)citrullination in a variety of diseases has been uncovered, including in MS, rheumatoid arthritis, Alzheimer's, scrapie, psoriasis and Creutzfeld-Jacob disease.[14,15]

In MS, extensive studies of hypercitrullinated MBP indicated that MBP, a key component of the myelin sheath and critical for the maintenance of myelin compaction, contained the non-coded amino acid citrulline in abnormal proportions. In normal brain, the "citrullinated MBP" accounts for 20% of the total MBP, whereas in chronic MS it accounts for 45%[16] and in fulminating MS it is 90% of the MBP.[17] In a number of studies using a variety of biophysical techniques,[18,19,20,21,22] it was demonstrated that citrullinated MBP prevented compaction of the bilayer, resulting in destabilization of the membrane and subsequent degradation leading to demyelination, and an irreversible damage to the axons.[23,24]

Thus, hypercitrullination is at the root of neuropathogenesis due to demyelination. In the central nervous system, peptidyl arginine deiminases (specifically PAD2 and PAD4) are responsible for the citrullination.

PAD Enzymes and Citrullination.

Peptidyl arginine deiminase (PAD) catalyzes the post-translational citrullination of proteins.[25,26,27] Citrullination is the process of deimination of Arg residues on select proteins, or in other words, transformation of Arg into citrulline via deimination (Scheme 1). There are five isozymes of PAD that exist in humans: PAD-1, -2, -3, -4 and -6. Their expression in tissues varies significantly, regulated by transcriptional and post-transcriptional mechanisms. PAD2 and PAD4 are specifically implied in MS, as enhanced levels of these two isoforms are observed in CNS under inflamed conditions.[28,29]

Scheme 1

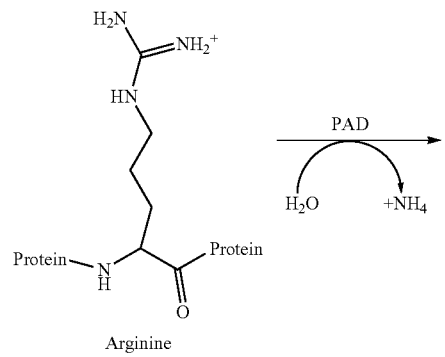

Arginine

-continued

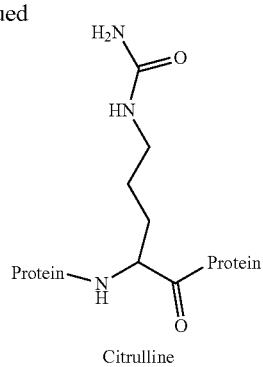

Citrulline

There is convincing evidence in vivo that higher levels of PAD activities and hypercitrullination are observed in MS.[30] For example, a routinely used MOG-EAE model for MS, which is a CD4(+) T cell-driven model, induced with the immunodominant 35-55 peptide of myelin oligodendrocyte glycoprotein (pMOG35-55) was used to test whether citrullination of a T cell epitope can contribute to disease etiopathology.[23,31] In this experimental model, the PAD2 and PAD4 enzymes were significantly upregulated in the inflamed CNS of the animals. T cells that responded specifically to the citrullinated pMOG could not initiate the EAE lesion, but these cells could provoke exacerbation of pathology if transferred into mice with an ongoing EAE. This experiment strongly suggested that once inflammation in MS is established, citrullination of target autoantigens can allow an expanded repertoire of T cells to contribute to CNS pathology, and enhanced levels of PAD enzymes are observed in these tissues.[31] A similar study using the peptides from myelin basic protein (MBP) epitopes indicated that self-antigens could potentially trigger the disease in susceptible individuals carrying citrullinated peptide epitopes.[32,33]

Inhibitors of PAD Enzymes:

A non-specific, active site PAD inhibitor, 2-chloroacetamidine (2CA), attenuated MS disease, decreased the amount of citrullinated protein and decreased PAD activity in the brain in four animal models of MS: two neurodegenerative and two autoimmune disease models.[34]

2CA is a covalent inhibitor of PAD4 (FIG. 2).

A non-specific, active site PAD inhibitor, 2-chloroacetamidine (2CA), was previously shown to attenuate MS disease, decrease the amount of citrullinated protein and decrease PAD activity in the brain in four different animal models of MS.[35] In one of these murine models, early and prolonged 2CA administration essentially prevented the disease. However, fully progressive clinical disease re-emerged promptly after therapy cessation at 6 months.[34] Thus, there remains a need to identify improved therapeutics for inhibiting disease-related hypercitrullination.

Structures of PAD Enzymes.

Structurally, PAD enzymes are $Ca^{2+}$-dependent enzymes that catalyze the conversion of arginine residues in proteins to citrulline via the deimination of the guanidinium moiety in the side chain of Arg residues.[36,37] The structure consists of the N-terminal domain predominately folded into β-sheets, and the C-terminal domain where the catalytic site is located. The catalytic site, where the substrate binds, has two Asp residues, one His residue and a Cys residue that are involved in the deimination reaction. Acidic amino acids, Asp350 and Asp473, function as general base residues during the hydrolysis of the amine in the guanidinium moiety of the peptidyl arginines. These two Asp residues are located in the bottom of the substrate-binding pocket (FIG. 2). 2CA, due to its acetamidine structure carrying a positive charge, binds at this anionic pocket and modifies the Cys residue that is in close proximity (FIG. 1). 2CA does not carry any additional structural features that provide it with specificity to inhibit PAD enzymes only, and not any other similar enzymes.

Over the past decade, there have been only a handful of efforts focused on understanding various ligands, their interactions and the inhibitors targeting PAD enzymes, and most notably, various peptide derivatives to understand the substrate and inhibitor properties targeting PAD enzymes.[33,38,39,40] The most potent non-peptidic compounds from these investigations are chlortetracycline, a tetracycline derivative with an $IC_{50}$ of 100±10 μM as a competitive inhibitor and a substrate analog, F-amidine with an $IC_{50}$ of 21±2.1 μM as an irreversible inactivator.

Non-immune small molecule therapies targeting specific neurological mechanisms are much needed for neurodegenerative diseases because immune-based therapies are not effective. PAD enzymes hypercitrullinate proteins in the brain leading to the pathology and neurodegeneration in Alzheimer's disease (AD).[41] This mechanism has been shown to operate in other neurodegenerative diseases such as MS, Parkinson's disease, amyotropic lateral sclerosis (ALS), multiple systems atrophy (MSA) and prion diseases such as Creutzfeldt-Jakob disease where hypercitrullination of myelin, higher expression of PAD2 and PAD4, and associated neurodegeneration are also observed.[58,42,43,44,45,46,47,48,49,67] PAD2 and PAD4 are shown to cause the pathology in brain regions such as hippocampus and cerebral cortex, ultimately leading to neurodegeneration and cell death. In MS and Alzheimer's disease, enhanced levels and activities of PAD, hypercitrullinated proteins, and ultimately neurodegeneration have been correlated with disease in patients' brain samples. In MS animal models, inhibition of PAD activities by treatment with small molecule inhibitors leads to the prevention and reversal of neurodegeneration and/or highly reduced inflammatory response in the brain.[50,51]

PAD enzymes and their catalytic activities leading to higher levels of citrullinated proteins in brain regions such as hippocampus, cerebral cortex and myelin are correlated to neurodegenerative changes typical for AD.[52] Throughout the process of neurodegeneration process, PAD2 and PAD4 specifically are abundantly expressed in brain.[69,53] Collectively evidence suggests that an abnormal activation of PAD2 and PAD4 in hippocampi of patients with AD finally leading to neurodegeneration.[70] Similar observations have been made in the mouse and rat models of AD.[54] Observations described here in the area of protein citrullination, inhibition of PAD enzymes and the development of novel inhibitors of PAD to prevent and/or reverse neurodegeneration and associated inflammation[67,68] will have applications as novel therapeutics targeting neurodegenerative diseases such as AD, MS, ALS, MSA, CJD etc.

Though current literature suggests the mammalian enzyme peptidylarginine deiminase type II (PAD2) does not use free arginine as a substrate[55] the enzyme is responsible for the conversion of peptide-bound positive arginine to neutral citrulline by means of a calcium ($Ca^{2+}$)-induced deimination reaction.[55,56] This deimination affects the behaviour of proteins in the cellular environment since it induces proteins to unfold, which could subsequently act as a catalyst for the aggregation of susceptible proteins.[57] The reaction catalyzed by PAD2 is localized to peptides in the astrocytes in the cerebral tissue that, as mentioned above, are reservoirs of arginine storage within the brain.[58]

SUMMARY OF THE APPLICATION

In vitro enzymology experiments disclosed herein revealed that the compounds described herein are, in one aspect of the disclosure, inhibitors of PAD1, PAD2 and/or PAD4. The compounds of the present application are, in one embodiment of the disclosure, useful as medicaments, for example, for treating diseases, disorders or conditions characterized by or associated with the hypercitrullination of proteins by peptidyl arginine deiminase (PAD) enzymes such as PAD1, PAD2 and PAD4.

Accordingly, the present application includes compounds of the formula (I)

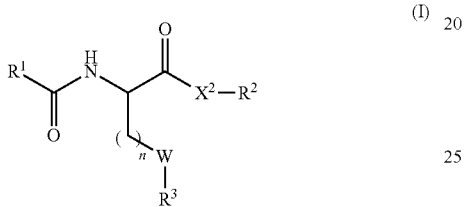

wherein:
$R^1$ is $C_{1-10}$alkyl, $C_{3-10}$cycloalkyl, $X^1$—$(CH_2)_{0-4}C_{3-10}$cycloalkyl, —$X^1$—$(CH_2)_{0-4}$aryl, $C_{6-10}$ aryl, $C_{5-10}$heteroaryl, hetero-$C_{3-10}$cycloalkyl, —$X^1$—$(CH_2)_{0-4}$heteroaryl, —$X^1$—$C_{1-10}$alkyl or $X^1$—$(CH_2)_{0-4}$heterocycloalkyl, each of which are optionally substituted with 1 to 3 substituents which are independently halo or $C_{1-6}$alkyl, and where $X^1$ if present is O or NH;
$X^2$ is O or NH; $R^2$ is $C_{1-6}$alkyl, $C_{6-10}$aryl, $C_{5-10}$heteroaryl, $(CH_2)_{1-4}$aryl, $(CH_2)_{1-4}C_{5-10}$ heteroaryl, $(CH_2)_{1-4}C(O)OC_{1-4}$ alkyl, $C_{6-10}$alkylaryl, $(CH_2)_{1-4}C(O)OH$, $(CH_2)_{1-4}C_{3-10}$ cycloalkyl or $(CH_2)_{1-4}NR^4R^5$, each of which are optionally substituted with 1 to 3 substituents independently which are halo, $C_{1-6}$alkyl, fluoro-substituted $C_{1-6}$alkyl, $C_{1-6}$-alkoxy, or —C(O)—N(R')$_2$ where each R' is independently or simultaneously H or $C_{1-6}$-alkyl;
n is 0, 1, 2 or 3;
$R^3$ is a PAD active site interacting group;
$R^4$ and $R^5$ are independently H, $C_{1-4}$alkyl, C(O)$C_{1-4}$alkyl, C(O)$C_{1-4}$alkylaryl or C(O)aryl; and
W is —CH$_2$— or —C(O);
or a pharmaceutically acceptable salt, solvate thereof, or stereoisomer thereof.

In another embodiment, $R^3$ is:
CN,

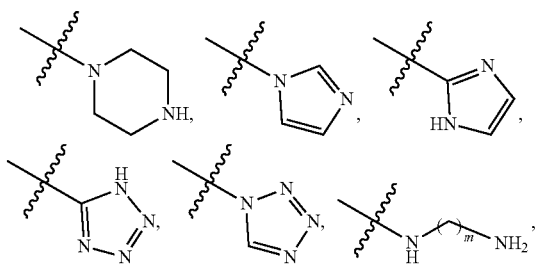

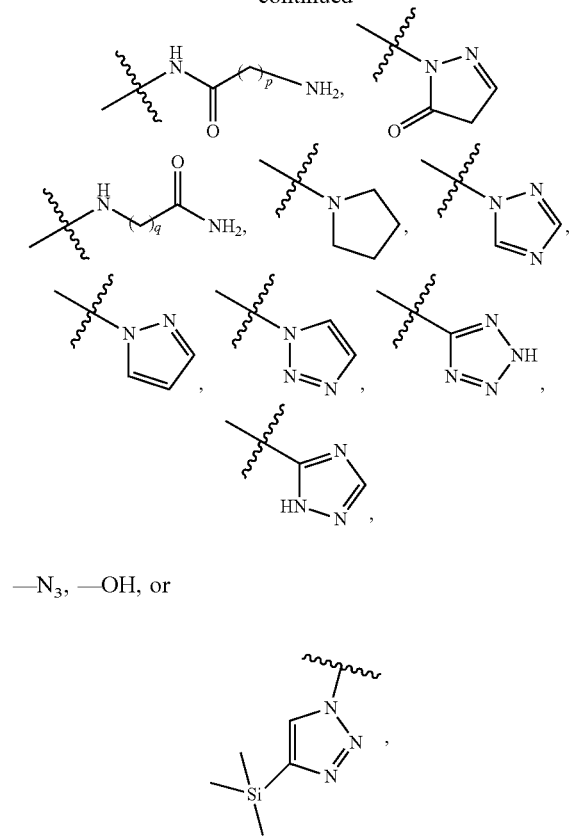

—N$_3$, —OH, or in which m, p, and q are, independently, 1, 2 or 3 and each cyclic group is unsubstituted or substituted with 1 to 3 substituents independently $C_{1-4}$alkyl, CN, OH, CN-substituted $C_{1-4}$alkyl, OH-substituted $C_{1-4}$alkyl or —N(R")$_2$ where each R" is independently or simultaneously H or $C_{1-6}$alkyl.

The present disclosure also includes a method for treating diseases, disorders or conditions characterized by or associated with the hypercitrullination of proteins by PAD enzymes comprising administering a therapeutically effective amount of one or more compounds of the Formula I as defined above.

Examples of such diseases, disorders or conditions include, for example, Parkinson's disease, amyotrophic lateral sclerosis (ALS), multiple system atrophy (MSA), multiple sclerosis (MS), arthritis, rheumatoid arthritis, Alzheimer's disease, psoriasis, and prion diseases such as scrapie and Creutzfeld-Jacob disease.

The present application also includes a composition comprising one or more compounds of Formula I as described above and a carrier. In an embodiment, the composition is a pharmaceutical composition comprising one or more compounds of Formula I as described above and a pharmaceutically acceptable carrier.

Other features and advantages of the present application will become apparent from the following detailed description. It should be understood, however, that the detailed description and the specific examples while indicating embodiments of the application are given by way of illustration only, the scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which.

DETAILED DESCRIPTION OF THE APPLICATION

I. Definitions

Figure 1:
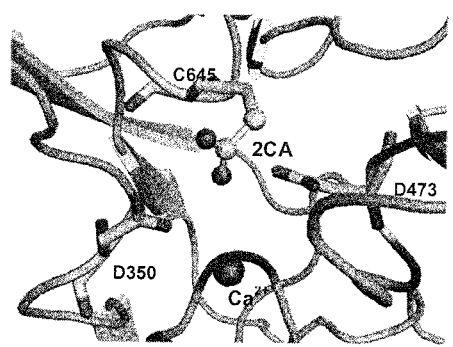
FIG. 1 shows a model of the covalent complex of 2CA bound to Cys645 in the active site of PAD4. The sphere labeled $Ca^{2+}$ is one of the $Ca^{2+}$ ions in proximity to the active site.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 50, 55, 60, 65, 70, 75, 80, 85, 90, 95 or 100% of the starting material or substrate is converted to product.

The term "suitable", as in for example, "suitable reagents", "suitable conditions", "suitable solvent" or "suitable amount" means that the selection of a particular compound, group or conditions would depend on the specific synthetic manipulation to be performed, and the identity of the molecule to be transformed, but the selection would be well within the skill of a person trained in the art. All process steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "compound(s) of the disclosure" or "compound(s) of the present disclosure" and the like as used herein includes compounds of Formula I, and a pharmaceutically acceptable salt and/or solvate thereof, or stereoisomer thereof as defined herein.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

An acid addition salt which is suitable for, or compatible with, the treatment of subjects as used herein means any non-toxic organic or inorganic salt of any basic compound.

Basic compounds that form an acid addition salt include, for example, compounds comprising an amine group. Illustrative inorganic acids which form suitable salts include hydrochloric, hydrotrifluoroacetic, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art. In an embodiment, the acid addition salt is a hydrochloride or hydrotrifluoroacetic acid salt.

A base addition salt which is suitable for, or compatible with, the treatment of subjects as used herein means any non-toxic organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "stereoisomer," as used herein, refers to all possible different isomeric as well as conformational forms which a compound of the formula (I) may possess, including all possible stereochemically and conformationally isomeric forms, all diastereomers, enantiomers and/or conformers of the basic molecular structure. In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early MS can be treated to prevent progression, or alternatively a subject in remission can be treated with a compound or composition described herein to prevent recurrence. Treatment methods comprise administering to a subject a therapeutically effective amount of one or more of the compounds of the application and optionally, consists of a single administration, or alternatively comprises a series of administrations. For example, the compounds of the application may be administered at least once a week. However, in another embodiment, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, the age of the patient, the concentration, the activity of the compounds of the application, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition characterized by or associated with the hypercitrullination of proteins by PAD enzymes or manifesting a symptom associated with a disease, disorder or condition characterized by or associated with the hypercitrullination of proteins by PAD enzymes.

As used herein, the term "effective amount" or "therapeutically effective amount" means an amount effective, at dosages and for periods of time necessary to achieve the desired result. For example, in the context of treating a disease, disorder or condition characterized by or associated with the hypercitrullination of proteins by peptidyl arginine deiminase (PAD) enzymes, an effective amount is an amount that, for example, reduces the hypercitrullination of proteins compared to the hypercitrullination of proteins without administration of the compound. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

The terms "characterized by" or "associated with" as used herein refers to a disease, disorder or condition in a subject wherein at least one of the causes is an enhanced level of activity in one or more of the PAD enzymes that catalyze the post-translational citrullination of proteins, compared to subjects that do not have the disease, disorder or condition. In an embodiment, PAD enzyme is PAD1, PAD2, PAD3, PAD4 and/or PAD6. In a further embodiment, the PAD enzyme is PAD1, PAD2 and/or PAD4. In yet another embodiment, the PAD enzyme is PAD2 and/or PAD4.

The term "administered" as used herein means administration of a therapeutically effective dose of a compound or composition of the application to a cell either in cell culture or in a patient.

Figure 2:
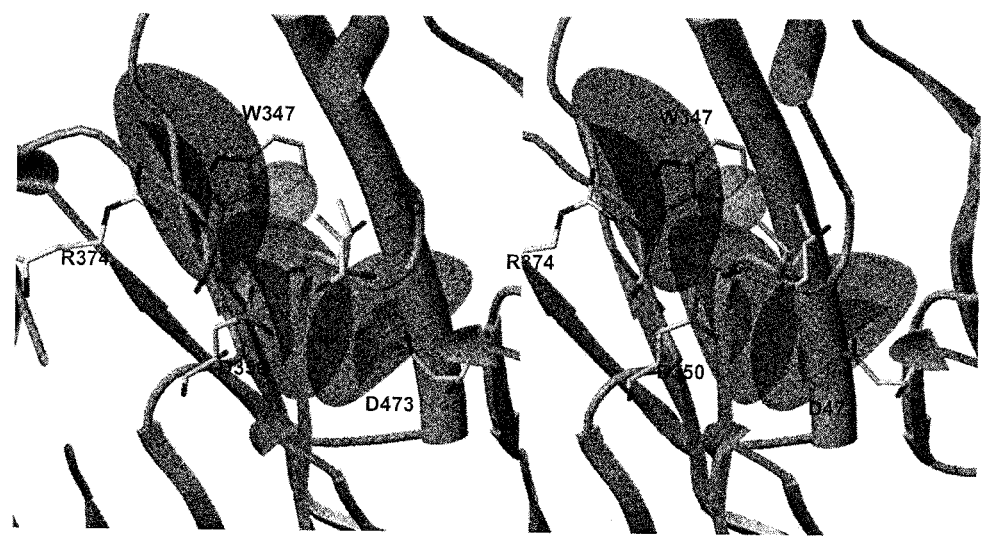
FIG. 2 shows a stereo view of the four selected features in the catalytic site of PAD4 overlapped onto the enzyme (cartoon model; source: crystal structure of PAD4 bound by a substrate analog N-benzoyl ethyl ester-L-arginine amide, PDB code: 1WDA).

The phrase "PAD active site interacting group" as used herein refers to a chemical group or moiety which is structurally capable of binding and/or interacting with the active site or catalytic site of a PAD enzyme, such as PAD1, PAD2 and/or PAD4, to effect inhibition of the PAD enzyme catalytic activity. Examples of PAD active site interacting groups include, but are not limited to, hetero-atom containing moieties such as, heterocycles, heteroaromatics, etc., which fit into the active site of a PAD enzyme, as depicted, for example, in FIGS. 1 and 2.

The use of the term "$C_{x\text{-}y}$" where x and y are integers means a moiety which includes at least x and no more than y carbon atoms. However, for groups containing heteroatoms this term would also include such atoms, though they are not carbon. For example, "$C_{5\text{-}10}$heteroaryl" denotes aryl groups in a ring of size 5, 6, 7, 8, 9, or 10 heavy atoms, of which at least one atom is O, S, or N. See the definitions below for further examples.

The term "alkyl" as used herein, whether it is used alone or as part of another group, means straight or branched chain, saturated alkyl groups. The term $C_{1\text{-}6}$alkyl means an alkyl group having 1, 2, 3, 4, 5 or 6 carbon atoms.

The term "cycloalkyl" as used herein, whether it is used alone or as part of another group, means cyclic, saturated alkyl groups. The term $C_{3\text{-}6}$cycloalkyl means a cycloalkyl group having 3, 4, 5 or 6 carbon atoms.

The term "heterocycloalkyl", as used herein, whether it is used alone or as part of another group, represents a cyclic alkyl, having at least one O, S and/or N atom interrupting the carbocyclic ring structure such as tetrahydrofuranyl, tetrahydropyranyl, piperidinyl, piperazinyl, morpholino and pyrrolidinyl groups.

The term "aryl" as used herein, whether it is used alone or as part of another group, means a mono-, bicyclic, or multicyclic carbocyclic ring system having one, two or more aromatic rings and is exemplified by phenyl, naphthyl, 1,2-dihydronaphthyl, 1,2,3,4-tetrahydronaphthyl, fluorenyl, indanyl, indenyl, and the like.

The term "heteroaryl", as used herein, whether it is used alone or as part of another group, represents an "aryl" as defined above, having at least one O, S and/or N interrupting the carbocyclic ring structure, such as pyridyl, furyl, pyrrolyl, thienyl, isothiazolyl, imidazolyl, benzimidazolyl, tetrazolyl, pyrazinyl, pyrimidyl, quinolyl, isoquinolyl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

The term "optionally substituted" as used herein means that the referenced group or atom is unsubstituted or substituted with another (different) group.

II. Compounds of the Disclosure

As noted above, in vitro enzymology experiments disclosed herein revealed that α-substituted amino acid derivatives of the formula (I) are, in one embodiment of the disclosure, inhibitors of PAD1, PAD2 and/or PAD4. The compounds of the present disclosure are, in one embodiment of the disclosure, useful for treating diseases, disorders or conditions characterized by or associated with the hypercitrullination of proteins by peptidyl arginine deiminase (PAD) enzymes.

Accordingly, the present disclosure is directed to compounds of the Formula I:

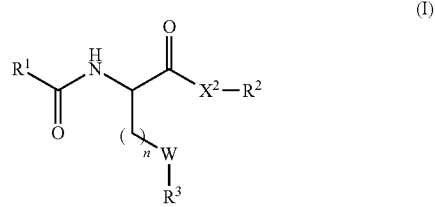

wherein:

$R^1$ is $C_{1\text{-}10}$alkyl, $C_{3\text{-}10}$cycloalkyl, —$X^1$—$(CH_2)_{0\text{-}4}C_{3\text{-}10}$cycloalkyl, $C_{6\text{-}10}$aryl, $C_{5\text{-}10}$heteroaryl, hetero-$C_{3\text{-}10}$cycloalkyl, —$X^1$—$(CH_2)_{0\text{-}4}$aryl, —$X^1$—$(CH_2)_{0\text{-}4}$heteroaryl, —$X^1$—$C_{1\text{-}10}$alkyl or —$X^1$—$(CH_2)_{0\text{-}4}$heterocycloalkyl, each of which are optionally substituted with 1 to 3 substituents independently which are halo or $C_{1\text{-}6}$alkyl, and where $X^1$ if present is O or NH;

$X^2$ is O or NH;

$R^2$ is $C_{1\text{-}6}$alkyl, $C_{6\text{-}10}$aryl, $C_{5\text{-}10}$heteroaryl, $(CH_2)_{1\text{-}4}$aryl, $(CH_2)_{1\text{-}4}C_{5\text{-}10}$heteroaryl, $(CH_2)_{1\text{-}4}C(O)OC_{1\text{-}4}$alkyl, $(CH_2)_{1\text{-}4}C(O)OH$, $C_{6\text{-}10}$alkylaryl, $(CH_2)_{1\text{-}4}C_{3\text{-}10}$cycloalkyl or $(CH_2)_{1\text{-}4}NR^4R^5$, each of which are optionally substituted with 1 to 3 substituents independently which are halo, $C_{1\text{-}6}$alkyl, fluoro-substituted $C_{1\text{-}6}$alkyl, $C_{1\text{-}6}$alkoxy, or —C(O)—N(R')$_2$ where each R' is independently or simultaneously H or $C_{1\text{-}6}$alkyl;

n is 0, 1, 2 or 3;

$R^3$ is a PAD active site interacting group;

$R^4$ and $R^5$ are independently H, $C_{1\text{-}4}$alkyl, $C(O)C_{1\text{-}4}$alkyl, $C(O)C_{1\text{-}4}$alkylaryl or $C(O)$aryl; and W is —$CH_2$— or —$C(O)$;

or a pharmaceutically acceptable salt, solvate thereof, or stereoisomer thereof.

In one embodiment, $R^3$ is a PAD active site interacting group which is —CN, —$N_3$, —OH, $C_{5\text{-}10}$heteroaryl or hetero-$C_{3\text{-}10}$cycloalkyl, the latter two groups being optionally substituted by —$(C_{1\text{-}6})$-alkyl or Si—$(CH_3)_3$, wherein the —$(C_{1\text{-}6})$-alkyl is further optionally substituted by CN.

In one embodiment, $R^3$ is a PAD active site interacting group which is:

CN, —$N_3$, —OH,

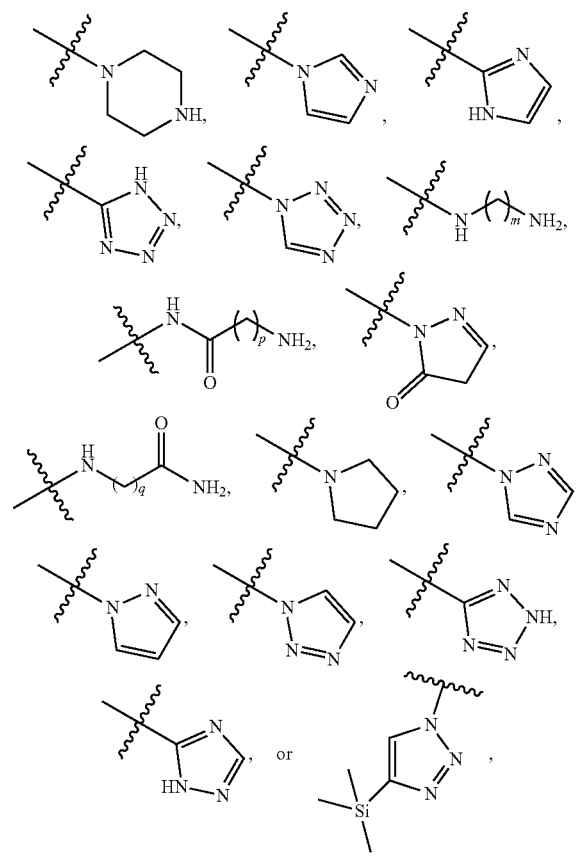

in which m, p, and q are, independently, 1, 2 or 3 and each cyclic group is unsubstituted or substituted with 1 to 3 substituents independently $C_{1-4}$alkyl, CN, OH, CN-substituted $C_{1-4}$alkyl, OH-substituted $C_{1-4}$alkyl or —$N(R'')_2$ where each R'' is independently or simultaneously H or $C_{1-6}$alkyl In another embodiment, $R^3$ is a PAD active site interacting group which is:

CN,

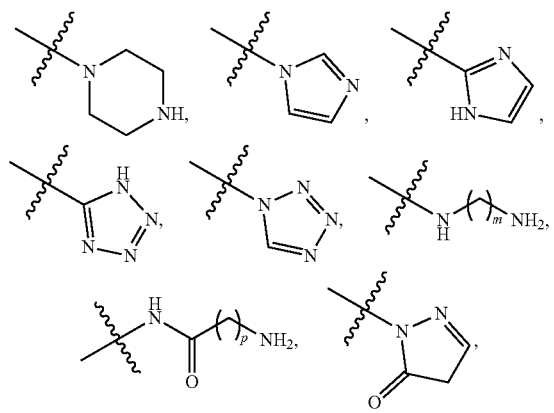

In a further embodiment, $R^3$ is a PAD active site interacting group which is:

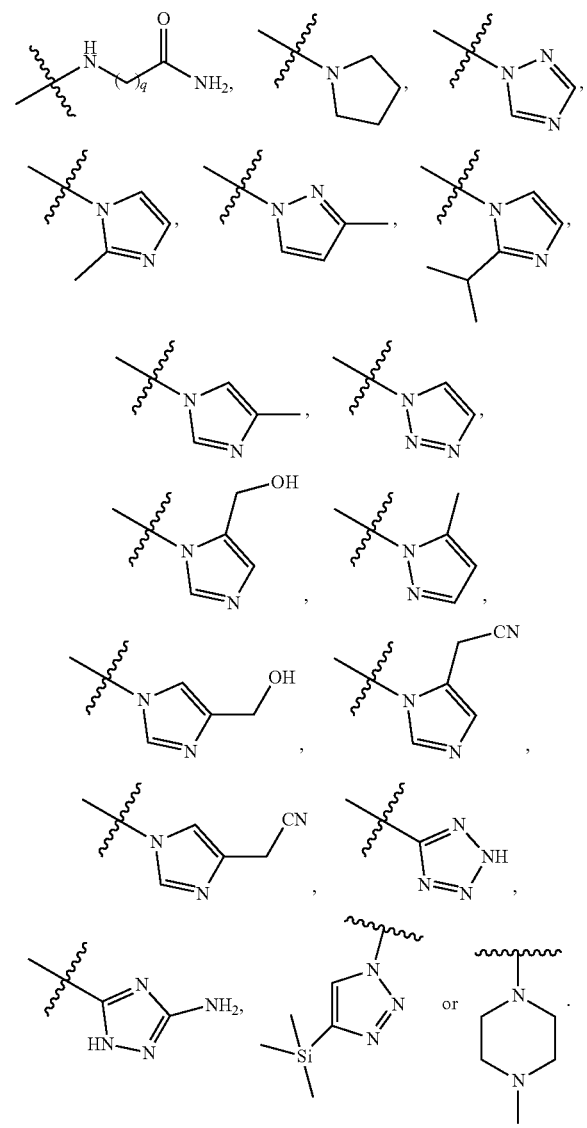

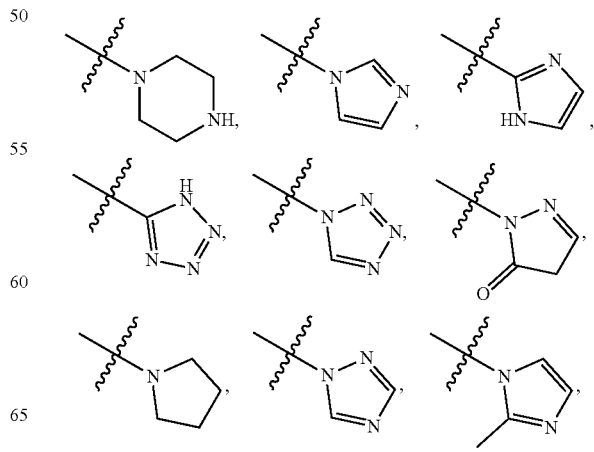

-continued

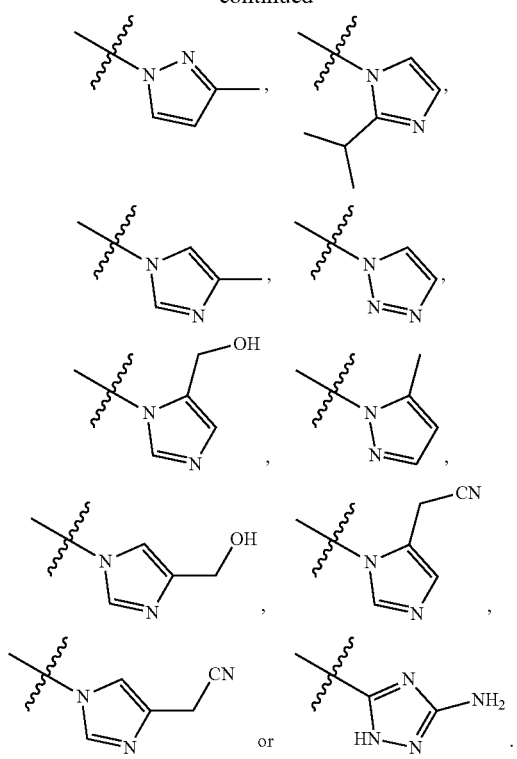

In a further embodiment, $R^3$ is a PAD active site interacting group which is:

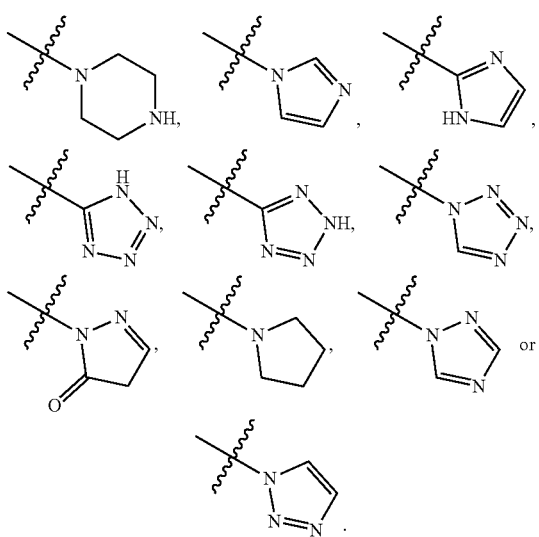

In an embodiment of the disclosure, $R^3$ is a PAD active site interacting group which is

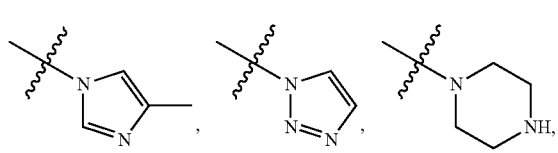

-continued

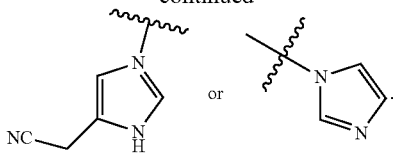

In another embodiment of the disclosure, $R^1$ is $C_{1-10}$alkyl, $C_{3-10}$cycloalkyl, $C_{6-10}$ aryl, $C_{5-10}$heteroaryl, hetero-$C_{3-10}$cycloalkyl, $X^1$—$(CH_2)_{0-4}C_{3-10}$cycloalkyl, $X^1$—$(CH_2)_{0-4}C_{6-10}$aryl, $X^1$—$(CH_2)_{0-4}C_{5-10}$heteroaryl, $X^1$—$C_{1-10}$alkyl, $(CH_2)_2$heteroaryl, or $X^1$—$(CH_2)_{0-4}$ heteroC$_{3-10}$cycloalkyl.

In a further embodiment, $R^1$ is $C_{1-6}$alkyl, $C_{3-6}$cycloalkyl, $C_6$aryl, $C_{5-6}$heteroaryl, hetero-$C_{3-6}$cycloalkyl, $X^1$—$(CH_2)_{0-4}C_{3-6}$cycloalkyl, $X^1$—$(CH_2)_{0-4}C_6$aryl, $X^1$—$(CH_2)_{0-4}C_{5-6}$ heteroaryl, or —$X^1$—$(CH_2)_{0-4}$heteroC$_{3-6}$cycloalkyl. In another embodiment, $R^1$ is $C_{1-6}$alkyl, $C_{3-6}$cycloalkyl, hetero-$C_{3-6}$cycloalkyl, $C_{5-6}$heteroaryl, $X^1$—$C_{1-6}$alkyl or $X^1$—$(CH_2)_{0-4}C_6$aryl. In a further embodiment, wherein $R^1$ is butyl, cyclohexyl, furanyl, $(CH_2)_2$furanyl, morpholinyl, piperidine, thienyl, thiazolyl, $X^1$—$C_{1-4}$alkyl or $X^1$—$CH_2$-phenyl.

In a further embodiment of the disclosure, $R^1$ is

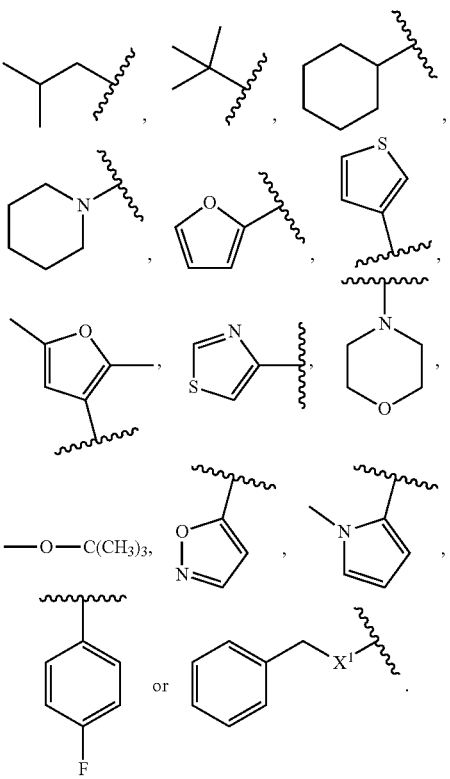

In another embodiment, $R^1$ is

-continued

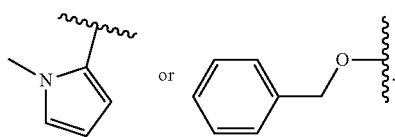

In one embodiment, R² is

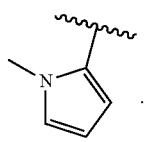 [SMILES: *c1cccn1C]

In another embodiment of the disclosure, R² is $C_{1-6}$alkyl, $C_{6-10}$aryl, $C_{5-10}$heteroaryl, $(CH_2)_{1-4}C_{6-10}$aryl, $(CH_2)_{1-4}C_{5-10}$heteroaryl, $(CH_2)_{1-4}C(O)OC_{1-4}$alkyl, $(CH_2)_{1-4}C(O)OH$, $(CH_2)_{1-4}C_{3-10}$cycloalkyl or $(CH_2)_{1-4}NR^4R^5$. In another embodiment, R² is $C_{1-4}$alkyl, $C_6$aryl, $C_{5-6}$heteroaryl, $(CH_2)_{1-4}C_6$aryl, $(CH_2)_{1-4}C_{5-9}$heteroaryl, $(CH_2)_{1-4}C(O)OC_{1-4}$alkyl, $(CH_2)_{1-4}C(O)OH$, $(CH_2)_{1-4}C_{3-6}$cycloalkyl or $(CH_2)_{1-4}NR^4R^5$. In a further embodiment, R² is $C_{1-4}$alkyl, $C_6$aryl, $C_{5-6}$heteroaryl, $(CH_2)_{1-4}C_{5-9}$heteroaryl, or $(CH_2)_{1-4}C_6$aryl. In another embodiment, the substituents on R² are independently halo, $C_{1-3}$alkyl, fluoro-substituted $C_{1-3}$alkyl, $C_{1-3}$alkoxy, or $-C(O)-NH_2$.

In another embodiment, R² is $CH_3$, $-CH(CH_3)_2$, $-CH_2CH_2OCH_3$, $-C(CH_3)_3$,

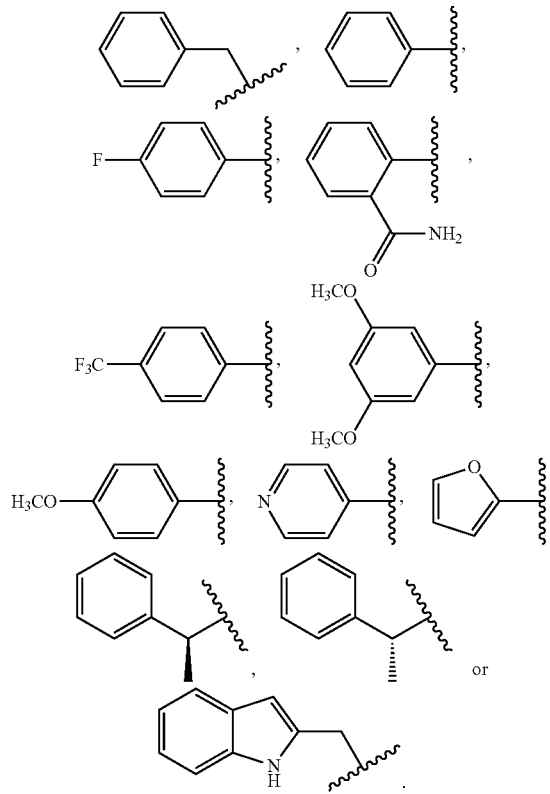

In another embodiment, R² is $CH_3$,

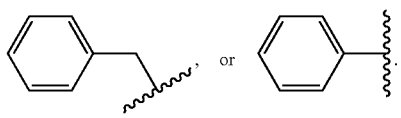 [SMILES: *Cc1ccccc1 ; *c1ccccc1]

In a further embodiment of the disclosure, X² is O. In another embodiment, X² is N.

In another embodiment, n is 0 or 1.

In an embodiment of the disclosure, n is 0 and W is $-CH_2-$. In another embodiment, n is 1 and W is $-C(O)-$.

In another embodiment of the disclosure, R⁴ and R⁵ are independently H, $C_{1-4}$ alkyl, $C(O)C_{1-4}$alkyl, $C(O)C_{1-4}$alkyl$C_{6-10}$aryl or $C(O)C_{6-10}$aryl. In another embodiment, R⁴ and R⁵ are independently H, $C_{1-4}$alkyl, $C(O)C_{1-4}$alkyl, $C(O)C_{1-4}$alkyl$C_6$aryl or $C(O)C_6$aryl.

In embodiment of the disclosure, the compound of Formula I is:

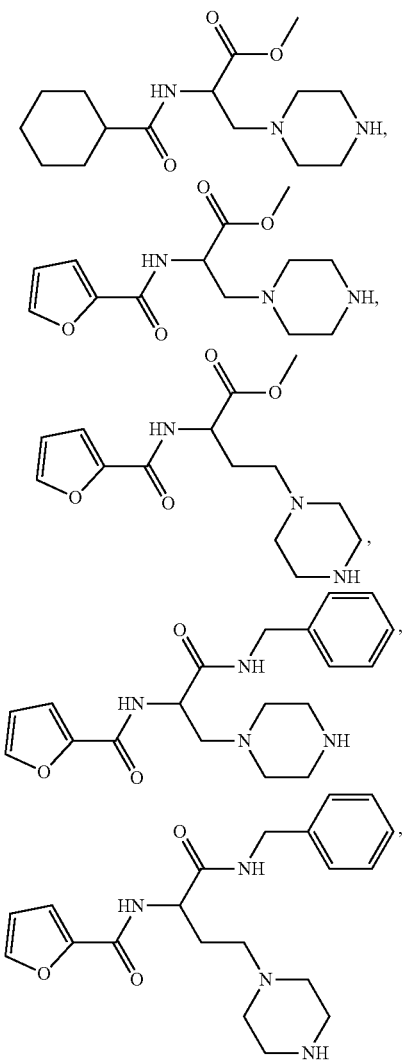

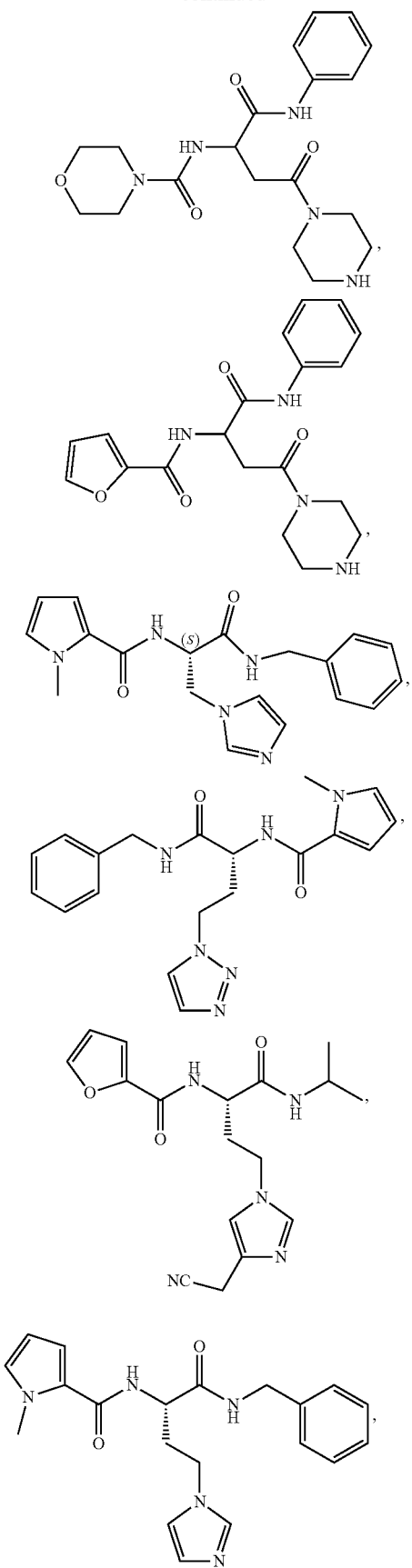
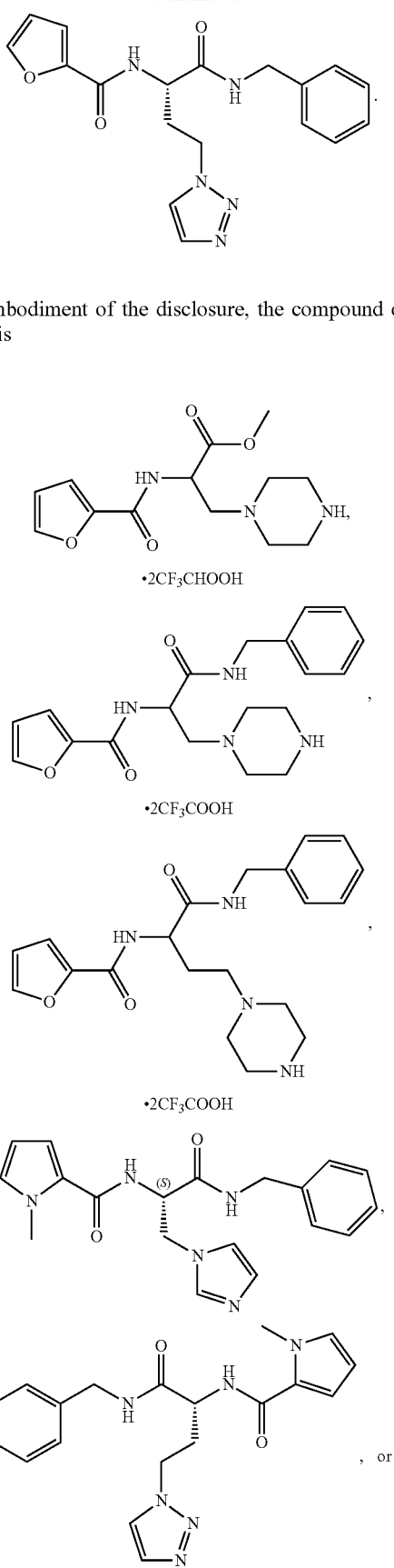
In embodiment of the disclosure, the compound of Formula I is

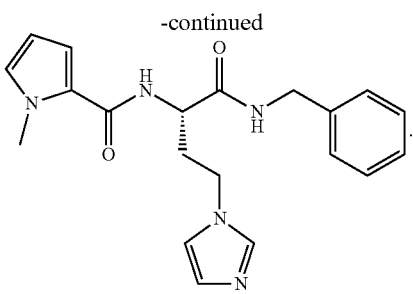

In a further embodiment, the compounds of Formula I are acid addition salts. In a further embodiment, the acid salt is a trifluoroacetic acid salt. In another embodiment, the acid salt is a hydrochloric acid salt. The preparation of salts of the compounds of the application can be performed by methods known in the art. For example, a solution of a suitable acid, for example, trifluoroacetic acid in a suitable solvent, for example dichloromethane can be added dropwise to a suitable amount of a solution of a compound of Formula I in a suitable solvent, for example, dichloromethane at a suitable temperature, for example at about −20° C. to about 20° C., or about 0° C., the reaction mixture stirred for a time of about 0.1 hour to about 24 hours, or about one hour, the temperature increased to a temperature of about 0° C. to about 50° C., or about room temperature, and the reaction mixture stirred for a time for the conversion of the reactants to the salt of the compound of Formula I to proceed to a sufficient extent, for example about 0.1 hour to about 24 hours, or about one hour.

The compounds of the formula (I) have at least one stereocenter as indicated by "*" in the formula below

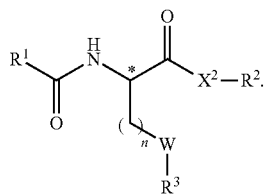

In one embodiment, the "*" denotes the "S" enantiomer. In another embodiment, the "*" denotes the "R" enantiomer.

II. Compositions of the Application

The present application also includes a composition comprising one or more compounds of Formula I:

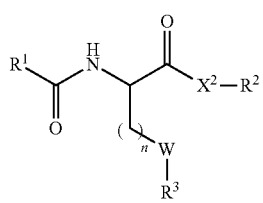

(I)

wherein the variables $R^1$-$R^3$, $X^2$, W and n are defined as above in each embodiment, and a carrier.

Said compounds of Formula I are suitably formulated into pharmaceutical compositions for administration to subjects in a biologically compatible form suitable for administration in vivo. Accordingly, the present application further includes a pharmaceutical composition comprising one or more compounds of said compound of Formula I and a pharmaceutically acceptable carrier.

The compounds of the disclosure may be formulated for administration to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the disclosure may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the disclosure and use the lyophilizates obtained, for example, for the preparation of products for injection.

A compound of the disclosure may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the disclosure may also be delivered by the use of monoclonal antibodies as individual carriers to which the compound molecules are coupled. Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Compounds of the disclosure may be used alone or in combination with other known agents useful for treating diseases, disorders or conditions characterized by or associated with the hypercitrullination of proteins by PAD enzymes such as PAD2 and PAD4. When used in combination with other agents useful in treating diseases, disorders or conditions characterized by or associated with the hypercitrullination of proteins by PAD enzymes such as PAD2 and PAD4, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the disclosure can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

III. Methods and Uses of the Disclosure

The present disclosure includes a method for treating diseases, disorders or conditions characterized by or associated with the hypercitrullination of proteins by PAD enzymes comprising administering a therapeutically effective amount of one or more compounds of the Formula (I)

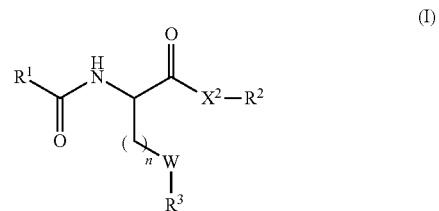

(I)

wherein the variables $R^1$-$R^3$, $X^2$, W and n are defined as above in each embodiment.

The present disclosure also includes a use of a therapeutically effective amount of one or more compounds of the Formula (I) for treating diseases, disorders or conditions characterized by or associated with the hypercitrullination of proteins by PAD enzymes

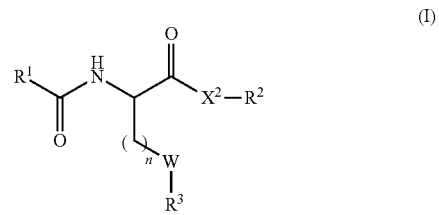

(I)

wherein the variables $R^1$-$R^3$, $X^2$, W and n are defined as above in each embodiment.

In embodiments of the disclosure, the diseases, disorders or conditions characterized by or associated with the hyper-citrullination of proteins by PAD enzymes such as PAD1, PAD2 and PAD4 include, for example, multiple sclerosis (MS), Parkinson's disease (PD), amyotrophic lateral sclerosis (ALS), multiple system atrophy (MSA), rheumatoid arthritis, Alzheimer's disease, psoriasis and prion diseases such as Creutzfeld-Jacob disease and scrapie. It is an embodiment that the disease, disorder or condition is multiple sclerosis.

In embodiments of the application, the PAD enzyme is PAD1, PAD2 and/or PAD4. In another embodiment of the application, the PAD enzyme is PAD2 and/or PAD4. In another embodiment of the application, the PAD enzyme is PAD2. In a further embodiment of the application, the PAD enzyme is PAD4.

The following non-limiting examples are illustrative of the present application:

EXAMPLES

All reagents were purchased from Sigma-Aldrich and BACHEM chemicals unless otherwise noted. The compounds were purified by column chromatography using silica gel (60 Å, 70-230 mesh) and reverse-phase (C18) silica cartridges. NMR spectra were recorded on a Bruker spectrometer (400 MHz for $^1$H, 100 MHz for $^{13}$C and 376.62 MHz for $^{19}$F). Chemical shifts δ are reported in ppm with trimethylsilane (TMS) for $^1$H and TFA for $^{19}$F as the internal standard, and are reported as s (singlet), brs (broad singlet), d (doublet), dd (doublet of doublet), t (triplet), q (quadruplet), and m (multiplet). UV-Vis and fluorescence spectra were recorded on a SpectraMax (Molecular Devices/GE Healthcare) plate reader in dioxane or PBS buffer as solvent. LC-MS analyses were conducted using a Waters™ system equipped with a Waters™ 2545 binary gradient module system and Waters™ 3100 mass detector, respectively. Final compounds were found to be more than 95% pure by two methods of HPLC analysis, and the details are presented in the Supporting Materials.

Examples 1-7 refer to the compounds and numbering as found in Scheme 1:

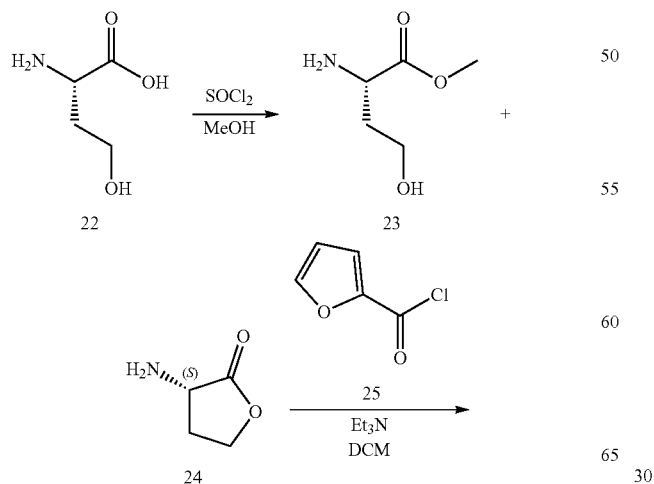

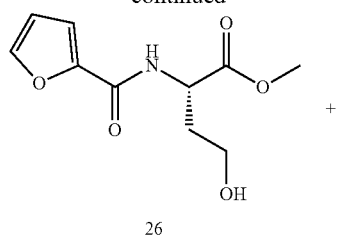

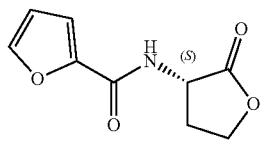

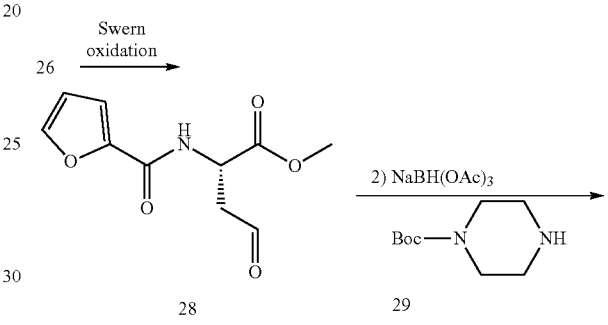

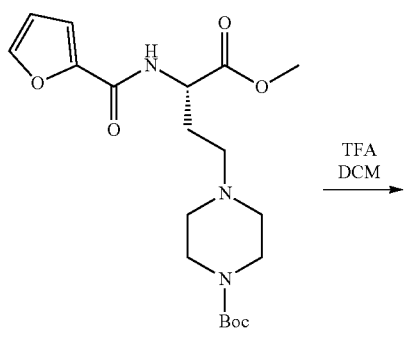

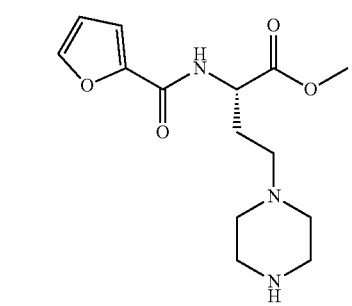

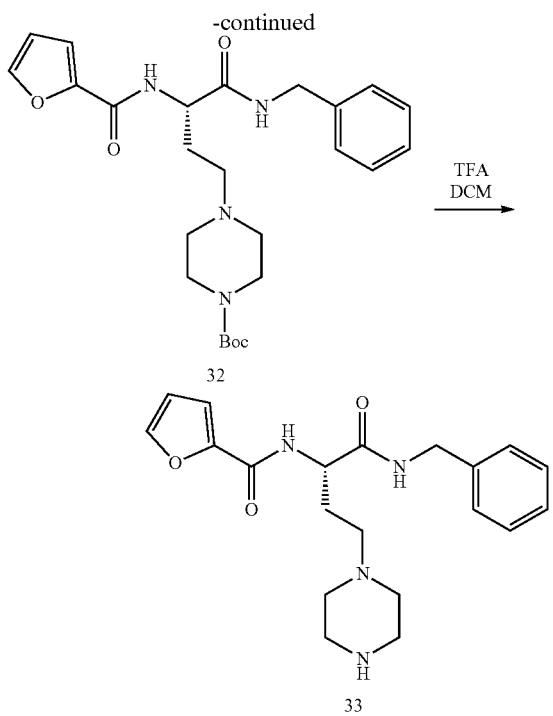

Example 1: Homoserine Methyl Ester (23) and Homoserine Lactone (24)

Thionyl chloride (10.1 mmol) was added dropwise to an ice-cooled reaction vessel containing MeOH (10 mL) under anhydrous conditions, and the resulting solution was stirred for 10 min. L-homoserine (22) (4.22 mmol) was added, and the resulting solution was stirred at 0° C. for 30 min, followed by warming to RT and stirring overnight. The solvent was removed in vaccuo to yield a 2.3:1 mixture of the hydrochloride salts of the lactone 24 and homoserine methyl ester 23. Compound 23: $^1$H NMR (MeOH-d$_4$) 4.19 (dd, J=5.14, 7.40 Hz, 1H), 3.86 (s, 3H), 3.72-3.81 (m, 2H), 2.13-2.23 (m, 1H), 2.01-2.12 (m, 1H). Compound 24: $^1$H NMR (400 MHz, MeOH-d4) 4.50-4.58 (m, 1H), 4.31-4.43 (m, 2H), 2.69-2.79 (m, 1H), 2.34 (qd, J=9.03, 11.71 Hz, 1H).

Example 2: (S)—N-(2-Oxotetrahydrofuran-3-yl) furan-2-carboxamide lactone (27) and (S)-methyl 2-(furan-2-carboxamido)-4-hydroxybutanoate hydroxyester (26)

2-Furoyl chloride (4.22 mmol) was added to an ice-cooled solution of the unpurified 2.3:1 mixture (662 mg) and DIPEA (12.7 mmol) in DCM (25 mL). The resulting solution was stirred in ice for 5 min, followed by stirring overnight at RT. The product was extracted into EtOAc, worked up and concentrated to provide the crude amide as a mixture of the lactone and hydroxy ester (769 mg). Purification by flash chromatography (EtOAc in DCM) gave pure 27 (314 mg) and 26 (319 mg). Compound 27: 1H NMR (400 MHz, MeOH-d$_4$) 7.66-7.71 (m, 1H), 7.16 (dd, J=0.75, 3.51 Hz, 1H), 6.61 (dd, J=1.76, 3.51 Hz, 1H), 4.78-4.85 (m, 1H), 4.50 (td, J=1.76, 9.03 Hz, 1H), 4.35 (ddd, J=6.65, 9.03, 10.42 Hz, 1H), 2.60 (dddd, J=1.88, 6.71, 9.00, 12.27 Hz, 1H), 2.36-2.50 (m, 1H). Compound 26: 1H NMR (400 MHz, MeOH-d$_4$) 7.67-7.72 (m, 1H), 7.16 (d, J=3.51 Hz, 1H), 6.61 (dd, J=1.76, 3.51 Hz, 1H), 4.74 (dd, J=4.77, 8.78 Hz, 1H), 3.75 (s, 3H), 3.61-3.74 (m, 2H), 2.17 (ddt, J=5.27, 8.66, 13.93 Hz, 1H), 1.97-2.09 (m, 1H).

Example 3: (S)-tert-Butyl 4-(3-(furan-2-carboxamido)-4-methoxy-4-oxobutyl)piperazine-1-carboxylate (28)

DMSO (3.0 mmol) was added over 5 min to a cold (−78° C.) solution of oxalyl chloride (1.52 mmol) in anhydrous DCM (2 mL) and stirred at −78° C. for 15 min. A solution of (S)-methyl 2-(furan-2-carboxamido)-4-hydroxybutanoate 26 (1.01 mmol) in anhydrous DCM (5 mL) was added, and the reaction mixture was stirred at −78° C. for 15 min. Et$_3$N (5.0 mmol) was added over 5 min, then warmed to RT over 20 min. The product was extracted with DCM, worked up, concentrated, and purified by Isolera system (EtOAc/hexane) to obtain the aldehyde 28 (86%). 1H NMR (400 MHz, CDCl$_3$) 9.77 (s, 1H), 7.48 (dd, J=0.75, 1.51 Hz, 1H), 7.23 (d, J=7.53 Hz, 1H), 7.12-7.17 (m, 1H), 6.51 (dd, J=1.63, 3.39 Hz, 1H), 4.99-5.08 (m, 1H), 3.74-3.85 (m, 3H), 3.11-3.33 (m, 2H).

Example 4: (S)-tert-Butyl 4-(3-(furan-2-carboxamido)-4-methoxy-4-oxobutyl)piperazine-1-carboxylate (30)

NaBH(OAc)$_3$ (1.29 mmol) was added to a solution of (S)-methyl-2-(furan-2-carboxamido)-4-oxobutanoate (28) (0.86 mmol) and tert-butyl piperazine-1-carboxylate (29) (0.96 mmol) in anhydrous 1,2-dichloroethane (15 mL), followed by 2 drops of glacial acetic acid. After the reaction mixture was stirred at RT for 2 h, the product was extracted into EtOAc, worked up and purified by Biotage™ Isolera system (EtOAc in hexane) to obtain compound 30 (90%). $^1$H NMR (CDCl3) δ 8.76 (d, J=6.53 Hz, 1H), 7.45 (dd, J=0.75, 1.76 Hz, 1H), 7.13 (dd, J=0.75, 3.51 Hz, 1H), 6.52 (dd, J=1.76, 3.51 Hz, 1H), 4.73-4.84 (m, 1H), 3.77 (s, 3H), 3.51 (t, J=4.77 Hz, 4H), 2.35-2.62 (m, 6H), 2.08-2.20 (m, 1H), 1.92-2.07 (m, 1H), 1.43-1.52 (m, 9H).

Example 5: (S)-Methyl 2-(furan-2-carboxamido)-4-(piperazin-1-yl)butanoate (31 or KP-31)

TFA (0.20 mL, 2.6 mmol) was added to an ice-cooled solution of (S)-tert-butyl 4-(3-(furan-2-carboxamido)-4-methoxy-4-oxobutyl)piperazine-1-carboxylate 30 (0.071 mmol) in anhydrous DCM (2 mL). The reaction mixture was stirred in ice for 10 min, then at RT for 2 h. Evaporation of the solvent and TFA in vacuo followed by purification on reverse phase (Isolera, 5% EtOH-95% water −0.05% TFA) gave a semipurified product. This compound was lyophilized, dissolved in MeOH and passed through a cation exchange column and eluted with 2M NH$_3$-MeOH, and further purified by Biotage™ Isolera system followed by lyophilization gave the title compound 31. $^1$H NMR (MeOH-d$_4$) 7.92 (s, 0.4H, partially exchanged amide NH), 7.73 (s, 1H), 7.15 (d, J=3.26 Hz, 1H), 6.62 (dd, J=1.63, 3.39 Hz, 1H), 4.67 (dd, J=4.89, 7.15 Hz, 1H), 3.76 (s, 3H), 2.88-2.98 (m, 4H), 2.38-2.64 (m, 6H), 2.14-2.26 (m, 1H), 1.99 (dt, J=6.68, 13.99 Hz, 1H).

Example 6: ((S)-tert-Butyl-4-(4-(benzylamino)-3-(furan-2-carboxamido)-4-oxobutyl)piperazine-1-carboxylate (32)

Trimethyl aluminum (2M in toluene, 0.38 mmol) was added to a solution of benzyl amine (0.37 mmol) in anhydrous DCM (1 mL) at RT and the resulting mixture was stirred for 15 min. A solution of (S)-tert-butyl 4-(3-(furan-2-carboxamido)-4-methoxy-4-oxobutyl)piperazine-1-carboxylate 30 (0.12 mmol) in anhydrous DCM was added at RT for 3.5 h then NaOH (aq) (1M, 1 mL). The product was extracted with DCM and purification by Biotage™ Isolera (EtOAc in hexane) to obtain the desired product 32 (64%). $^1$H NMR (CDCl3) δ 8.64 (d, J=6.53 Hz, 1H), 7.46 (d, J=1.00 Hz, 1H), 7.22-7.40 (m, 6H), 7.12 (d, J=3.51 Hz, 1H), 6.52 (dd, J=1.76, 3.51 Hz, 1H), 4.65-4.74 (m, 1H), 4.47-4.56 (m, 1H), 4.38-4.46 (m, 1H), 3.38 (br. s., 4H), 2.56-2.67 (m, 1H), 2.33-2.51 (m, 3H), 2.14-2.31 (m, 3H), 1.91 (ddt, J=3.73, 7.40, 14.74 Hz, 1H), 1.47 (s, 9H).

Example 7: (S)—N-(1-(Benzylamino)-1-oxo-4-(piperazin-1-yl)butan-2-yl)furan-2-carboxamide (33 or KP-228)

TFA (3.9 mmol) was added to an ice-cooled solution of ((S)-tert-butyl 4-(4-(benzylamino)-3-(furan-2-carboxamido)-4-oxobutyl)piperazine-1-carboxylate 32 (0.072 mmol) in anhydrous DCM (2 mL). The reaction mixture was stirred in ice for 5 min, then at RT for 1.5 h. The product was extracted into DCM and purification by reverse phase using Isolera (30 g Biotage RP-18 plus Samplet®, gradient 5-95% MeOH-0.1% TFA in water) followed by lyophilization gave compound 33 (58%). $^1$H NMR (MeOH-$d_4$) 7.72 (d, J=1.00 Hz, 1H), 7.29-7.36 (m, 4H), 7.22-7.28 (m, 1H), 7.19 (d, J=3.51 Hz, 1H), 6.63 (dd, J=1.76, 3.51 Hz, 1H), 4.70 (dd, J=5.52, 7.78 Hz, 1H), 4.37-4.47 (m, 2H), 2.84-3.02 (m, 4H), 2.67-2.83 (m, 2H), 2.22 (dt, J=6.87, 13.11 Hz, 1H), 1.96-2.09 (m, 1H). $^{19}$F NMR (377 MHz, MeOH-$d_4$) −77.1.

Examples 8-12 refer to the compounds and numbering as found in Scheme 2:

Scheme 2

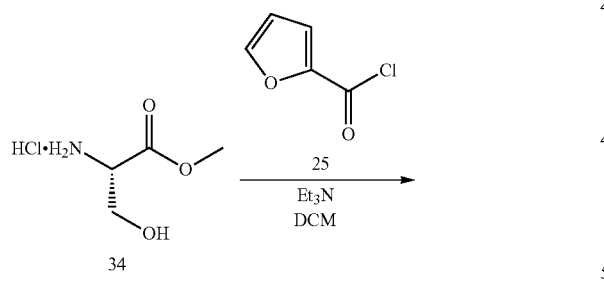

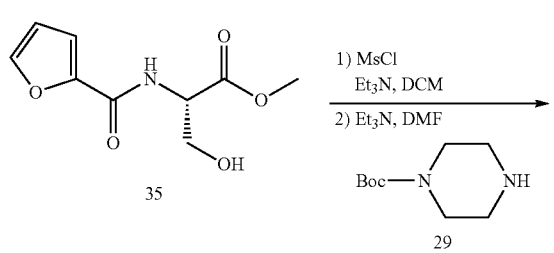

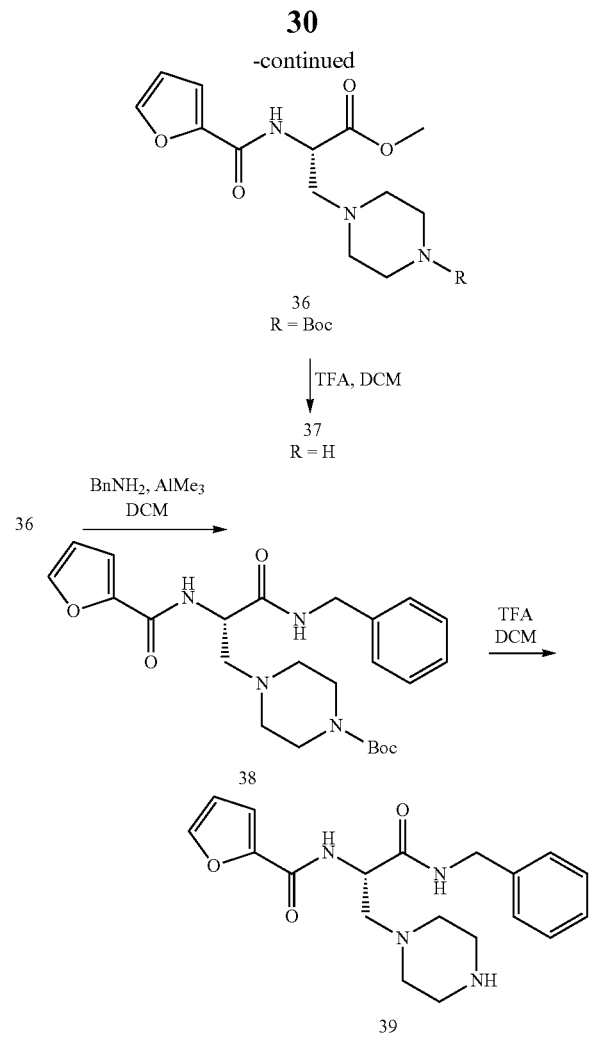

Example 8: (S)-Methyl 2-(furan-2-carboxamido)-3-hydroxypropanoate (35)

2-Furoyl chloride 25 (6.58 mmol) was added in a drop-wise manner to an ice-cooled solution of L-serine methyl ester hydrochloride 34 (6.48 mmol) and Et$_3$N (19.5 mmol) in DCM (30 mL). The resulting solution was stirred in ice for 15 min, then for 18 h at RT. The product was extracted into DCM, worked up and purified on Isolera system (EtOAc in DCM) gave a small amount of diacylated product (34.5 mg) along with the desired compound 35 (840.2 mg, 61%). $^1$H NMR (400 MHz, MeOH-$d_4$) δ 7.71 (d, J=1.00 Hz, 1H), 7.18 (d, J=3.51 Hz, 1H), 6.62 (dd, J=1.63, 3.39 Hz, 1H), 4.71 (t, J=4.27 Hz, 1H), 3.97-4.03 (m, 1H), 3.89-3.95 (m, 1H), 3.78 (s, 3H).

Example 9: (S)-tert-Butyl 4-(2-(furan-2-carboxamido)-3-methoxy-3-oxopropyl)piperazine-1-carboxylate (36)

Methanesulfonyl chloride (1.16 mmol) was added in a drop wise manner to an ice-cooled solution of (S)-methyl 2-(furan-2-carboxamido)-3-hydroxypropanoate 35 (1.01 mmol) and Et$_3$N (1.15 mmol) in DCM (5 mL). The resulting solution was stirred at 0° C. for 1 h, and tert-butyl piperazine-1-carboxylate 29 (1.18 mmol) and Et$_3$N (2.3 mmol) were added and the reaction was stirred in ice for 40 min and continued stirring at RT for 17 h. The solvent was evaporated in vacuo and DMF (3 mL) was added and the reaction mixture was heated at 70° C. for 4 h. The product was extracted into EtOAc, worked up and purified by Isolera (25 g Silicycle column plus 2 g silica dry loading, 40-80% EtOAc in hexane) gave compound 36 (63%). $^1$H NMR (CDCl$_3$) 7.45-7.53 (m, 1H), 7.08-7.21 (m, 2H), 6.52 (dd, J=1.76, 3.51 Hz, 1H), 4.74 (q, J=6.53 Hz, 1H), 3.78 (s, 3H), 3.42 (t, J=5.02 Hz, 4H), 2.79-2.91 (m, 2H), 2.40-2.53 (m, 4H), 1.46 (s, 9H).

Example 10: (S)-Methyl 2-(furan-2-carboxamido)-3-(piperazin-1-yl)propanoate (37 or KP-225))

TFA (2.6 mmol) was added to an ice-cooled solution of (S)-tert-butyl 4-(2-(furan-2-carboxamido)-3-methoxy-3-oxopropyl)piperazine-1-carboxylate 36 (0.073 mmol) in anhydrous DCM (2 mL). The reaction mixture was stirred in ice for 15 min, then at RT for 1 h. Evaporation of the solvent and TFA in vacuo followed by purification on reverse phase (Isolera) gave a product which was not pure (elution with the solvent front using 5% EtOH-95% water-0.05% TFA). Trituration with ether and lyophilization, gave compound 37 (34 mg, 91%). $^1$H NMR (MeOH-d$_4$) δ 7.71 (d, J=1.00 Hz, 1H), 7.17 (d, J=3.51 Hz, 1H), 6.62 (dd, J=1.63, 3.39 Hz, 1H), 4.83-4.87 (m, 1H), 3.77 (s, 3H), 3.22 (t, J=4.89 Hz, 4H), 2.95-3.07 (m, 2H), 2.86-2.95 (m, 2H), 2.76-2.86 (m, 2H); $^{19}$F NMR (377 MHz, MeOH-d$_4$) −77.1.

Example 11: (S)-tert-Butyl 4-(3-(benzylamino)-2-(furan-2-carboxamido)-3-oxopropyl)piperazine-1-carboxylate 38

Me$_3$Al (2M in toluene, 0.38 mmol) was added to a solution of benzyl amine (0.37 mmol) in anhydrous DCM (1 mL) at RT and the resulting mixture was stirred for 15 min. A solution of using (S)-tert-butyl 4-(2-(furan-2-carboxamido)-3-methoxy-3-oxopropyl)piperazine-1-carboxylate 36 (0.12 mmol) in anhydrous DCM (1.5 mL, plus rinsed with 2×1 mL) was added at RT for 3.5 h. NaOH$_{(aq)}$ (1M, 1 mL) was added slowly for the first 5 drops and then more rapidly followed by water (1 mL). The product was extracted with DCM, worked up and triturated with 15% EtOAc in hexane to give 38 as a white solid (71%). $^1$H NMR (CDCl$_3$) 8.12 (br. s., 1H), 7.47-7.49 (m, 1H), 7.44 (d, J=5.52 Hz, 1H), 7.33-7.38 (m, 2H), 7.28-7.32 (m, 3H), 7.11 (d, J=3.51 Hz, 1H), 6.50 (dd, J=1.76, 3.51 Hz, 1H), 4.62 (dd, J=6.40, 14.43 Hz, 1H), 4.52 (ddd, J=3.89, 5.83, 10.10 Hz, 1H), 4.35 (dd, J=4.77, 14.56 Hz, 1H), 3.28 (br. s., 4H), 2.89 (dd, J=4.02, 12.55 Hz, 1H), 2.70 (br. s., 2H), 2.51-2.58 (m, 1H), 2.30-2.37 (m, 2H), 1.45 (s, 9H).

Example 12: (S)—N-(1-(Benzylamino)-1-oxo-3-(piperazin-1-yl)propan-2-yl)furan-2-carboxamide (S5) (39 or KP-227)

TFA (0.25 mL, 3.3 mmol) was added to an ice-cooled solution of (S)-tert-butyl 4-(3-(benzylamino)-2-(furan-2-carboxamido)-3-oxopropyl)piperazine-1-carboxylate 38 (0.079 mmol) in anhydrous DCM (2 mL). The reaction mixture was stirred in ice for 10 min, then at RT for 2 h. The product was extracted into DCM, worked up and purified by reverse phase column chromatography on a Biotage™ Isolera (30 g Biotage RP-18 plus Samplet®, gradient 5-95% MeOH-0.1% TFA in water) followed by lyophilization gave compound 38 (56%). $^1$H NMR (400 MHz, MeOH-d$_4$) δ ppm 8.68 (d, J=5.02 Hz, 1H), 7.71 (dd, J=0.75, 1.76 Hz, 1H), 7.33 (d, J=4.52 Hz, 4H), 7.22-7.30 (m, 1H), 7.16-7.20 (m, 1H), 6.62 (dd, J=1.76, 3.51 Hz, 1H), 4.74 (t, J=7.28 Hz, 1H), 4.45-4.55 (m, 1H), 4.30-4.39 (m, 1H), 3.05-3.18 (m, 4H), 2.86-2.93 (m, 1H), 2.79-2.85 (m, 1H), 2.73-2.79 (m, 4H); $^{19}$F NMR (377 MHz, MeOH-d$_4$) −77.1.

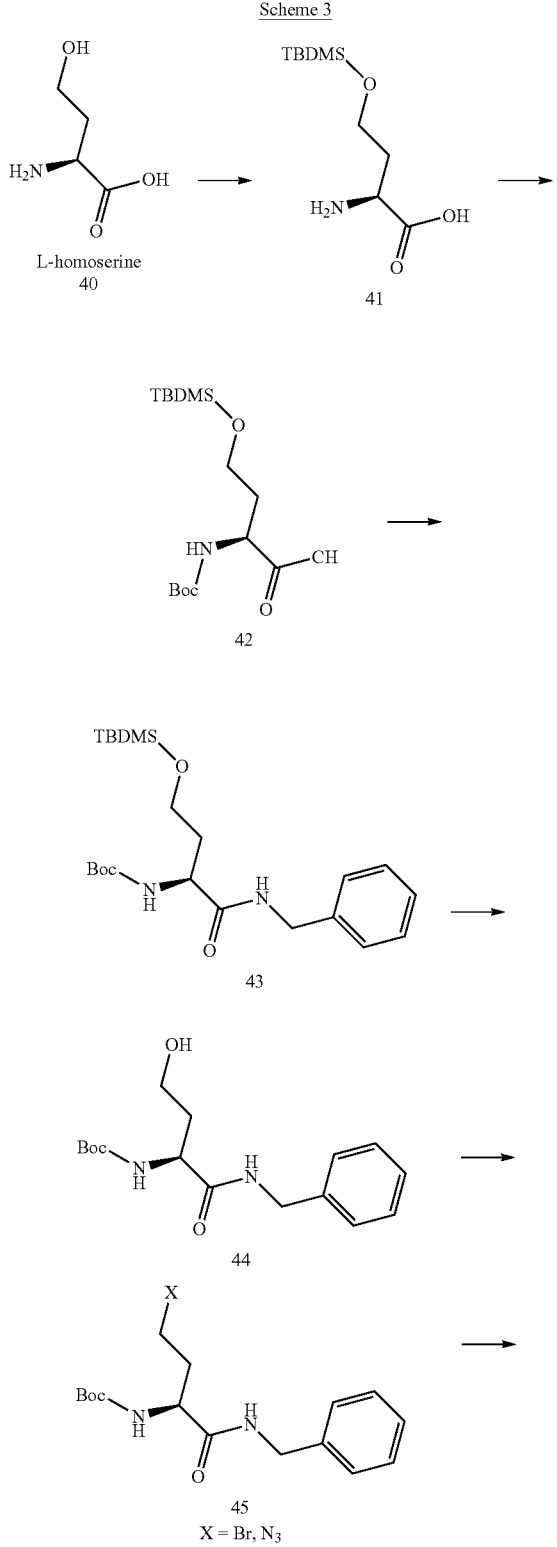

Scheme 3

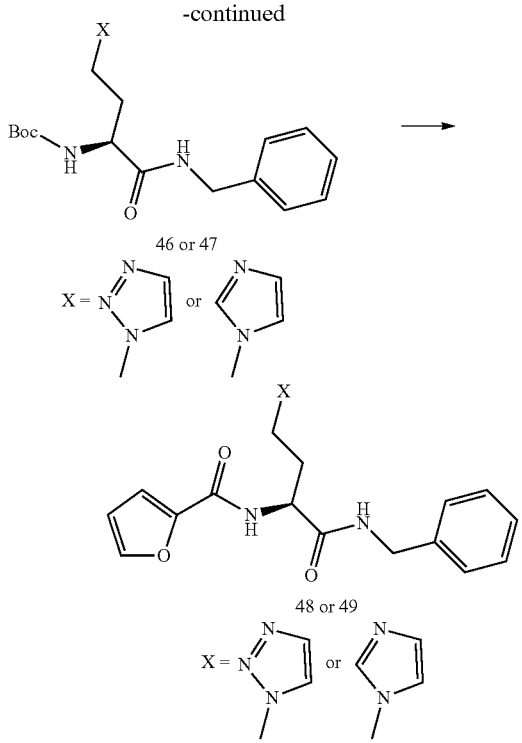

Examples 13 to 22 refer to numbers and schemes 3:

Example 13:
O-(Tert-butyldimethylsilyl)-L-Homoserine (41)

L-homoserine (40) (1 g, 8.4 mmol) and DBU (8.8 mmol) were dissolved in 20 mL of anhydrous MeCN and stirred at 0° C. Tertbutyldimethysilyl chloride (8.8 mmol) was dissolved in 20 mL of a MeCN and added dropwise over 5 min. The reaction mixture was warmed to rt and stirred overnight. A white precipitate formed was and was washed with MeCN (200 mL cold dH$_2$O (200 mL), and Et$_2$O (200 mL) and dried under vacuum to afford 41 as a white powder (78%). $^1$H NMR (CD$_3$OD) δ 3.87 (t, J=6 Hz, 2H), 3.71-3.68 (m, 1H), 2.21-1.93 (m, 2H), 0.93 (s, 9H), 0.12 (s, 6H).

Example 14: N-(Tert-butoxycarbonyl)-O-(tert-butyldimethylsilyl)-L-homoserine (42)

Compound 41 (10.11 mmol) was dissolved in a 50 mL solution of 1:1 acetone:dH2O. Et$_3$N (15.17 mmol) and Boc-anhydride (11.12 mmol) were added to reaction and stirred at rt. Reaction was monitored by TLC in 95:5 DCM:MeOH until 41 was completely consumed. Reaction solvent was evaporated in vacuo and remaining aqueous layer was acidified to pH 2.0 with 10% citric acid. The aqueous layer was extracted with EtOAc (3×200 mL) and dried over MgSO$_4$ to afford 42 as a viscous white solid (81%). $^{1H\ NMR}$ (CDCl$_3$): δ 5.92 (d, 1H, NH), 4.33, (q, 1H), 3.81 (m, 2H), 2.07 (m, 2H), 1.441 (s, 9H), 0.910 (s, 9H), 0.08 (d, J=4 Hz, 6H).

Example 15: Tert-butyl (S)-(1-(benzylamino)-4-((tert-butyldimethylsilyl)oxy)-1-oxobutan-2-yl)carbamate (43)

Compound 42 (8.16 mmol) were dissolved in 15 mL of anhydrous MeCN to which DIPEA (24.47 mmol) and HATU (8.97 mmol) were added and stirred at 4° C. Benzylamine (8.97 mmol) were added drop wise to reaction mixture and further stirred at 4° C. for 6 hr. Reaction solvent was evaporated in vacuo and resulting crude was dissolved in 15 mL of EtOAc, extracted with dH$_2$O (150 mL) and brine (150 mL), and dried over MgSO$_4$. Crude was then purified by silica chromatography in a 5-30% gradient of EtOAC in hexanesto yield 43 as a clear oil (85%). $^{1H\ NMR}$ (CDCl$_3$) (7.37 (m, 5H), 7.10 (d, 1H, NH), 6.20 (d, 1H, NH), 4.55 (dd, J 4 Hz, 2H), 4.41 (m, 1H), 3.85 (m, 2H), 2.12 (m, 2H), 1.52 (s, 9H), 0.99 (s, 9H), 0.145 (d, J=4 Hz, 6H).

Example 16: Tert-butyl (S)-(1-(benzylamino)-4-hydroxy-1-oxobutan-2-yl)carbamate (44)

Compound 43 (2.67 mmol) were dissolved in 10 mL of anhydrous THF and stirred at 0° C. TBAF (2.67 mmol) were added drop wise to reaction mixture and further stirred 0° C. Reaction was monitored by TLC 3:2 EtOAc:hexanes until 43 was consumed. Reaction solvent was removed and remaining crude was purified by silica chromatography in a 10-80% EtOAc gradient in hexanes to afford 44 as a white solid (82%). $^{1H\ NMR}$ (CDCl$_3$): δ 7.59 (d, 1H, NH), 7.30-7.20 (m, 5H), 5.86 (d, 1H, NH), 4.38 (dd, J=4 Hz, 2H), 4.31 (m, 1H), 3.60 (m, 2H), 1.98-1.69 (m, 2H), 1.40 (s, 9H).

Example 17: Tert-butyl (S)-(1-(benzylamino)-4-bromo-1-oxobutan-2-yl)carbamate (45a)

Compound 44 (810.71 μmol) and carbon tetrabromide (1.22 mmol) were dissolved in 10 mL anhydrous DCM and stirred at 0° C. Triphenylphosphine (1.22 mmol) was dissolved in 5 mL of anhydrous DCM and added dropwise to the reaction mixture over a 5 min period. Reaction was stirred at 0° C. for 10 min and then allowed to warm to rt. Reaction was monitored by TLC 3:7 EtOAc:hexanes until 44 was consumed. Reaction solvent was evaporated and crude was purified by silica chromatography in a 10-40% EtOAc gradient in hexanes to afford 45a as a white powder (58%). $^{1H\ NMR}$ (400 MHz, CDCl$_3$): δ 7.59 (d, 1H, NH), 7.22 (m, 5H), 6.09 (d, 1H, NH), 4.41 (dd, J=4 Hz, 2H), 4.31 (m, 1H), 3.39 (m, 2H), 2.42-2.14 (m, 2H), 1.40 (s, 9H).

Example 18: Tert-butyl (S)-(4-azido-1-(benzylamino)-1-oxobutan-2-yl)carbamate (45b)

Compound 44 (5.67 mmol) was dissolved in 5 mL of anhydrous DCM and stirred at 0° C. DIPEA (17.02 mmol) and MsCl (6.24 mmol) were added dropwise and further stirred at 0° C. until 44 was consumed. Reaction solvent was then evaporated and crude was redissolved in 30 mL of EtOAc and washed with dilute NH$_4$Cl (150 mL) and brine (150 mL) and dried over MgSO$_4$. Organic layer was evaporated and resulting yellow solid was redissolved in 5 mL of anhydrous DMF. Sodium azide (4.0 eq) was added to reaction and stirred at 60° C. for 2.5 hr. Reaction solvent was evaporated, crude was dissolved in EtOAc and worked up and purified by silica chromatography (EtOAc:hexanes) to yield 45b as a viscous liquid (55%). $^{1H\ NMR}$(CDCl$_3$) δ 7.32-7.24 (m, 5H), 6.684 (broad s, 1H, NH), 5.26 (d, 1H, NH), 4.40 (dd, J=4 Hz, 2H), 4.21 (septet, 1H), 3.41 (m, 2H), 2.09-2.01 (m, 1H), 1.96-1.92 (m, 1H), 1.42 (s, 9H).

Example 19: Tert-butyl(S)-(1-(benzylamino)-4-(1H-imidazol-1-yl)-1-oxobutan-2-yl)carbamate (46)

Compound 45a (1.40 mmol) were dissolved in 3 mL of anhydrous DMF and stirred at 0° C. A solution of imidazole (3.50 mmol) and DIPEA (2.10 mmol) in DMF was added drop wise to bromide mixture and further stirred at 0° C. Reaction was monitored by TLC 9:1 DCM: MeOH until 45a was consumed. Reaction solvent was evaporated in vacuo and resulting crude was dissolved in EtOAc (100 mL), worked up and was purified by silica chromatography in a 30-70% EtOAc gradient in hexanes and then in a 0-10% MeOH gradient in DCM to yield 46 as a yellow solid (76%). $^{1H\ NMR}$ (CDCl$_3$) δ 8.17 (s, 1H), 7.32 (d, J=4 Hz, 1H), 7.21 (m, 5H), 6.87 (d, J=4 Hz, 1H), 5.94 (d, 1H, NH), 4.38 (dd, J=4 Hz, 2H), 4.22 (m, 1H), 3.97 (m, 2H) 2.24-1.99 (m, 2H), 1.43 (s, 9H).

Example 20: Tert-butyl (S)-(1-(benzylamino)-1-oxo-4-(4-(trimethylsilyl)-1H-1,2,3-triazol-1-yl)butan-2-yl)carbamate (47)

To a suspension of CuI (1.28 mmol) in 5 mL of anhydrous THF, TEMED (1.28 mmol), Et$_3$N (1.28 mmol), and TMS-acetylene (6.45 mmol) were added and stirred at rt. 45b (2.58 mmol) was dissolved in 10 mL of anhydrous THF and immediately added to reaction mixture and allowed to stir at rt for 18 hr. Reaction was quenched with dH$_2$O and extracted in 60 mL EtOAc. Organic layer was then washed with brine (150 mL) and dried over MgSO$_4$. Resulting crude was purified by silica chromatography in a 30-60% EtOAc gradient in hexanes to afford a white solid. Compound was dissolved in 10 mL of anhydrous THF containing a 1M AcOH and stirred at 0° C. TBAF (470 μL, 1.62 mmol) was added and reaction was allowed to warm up to rt and stir for 16 hr. Reaction solvent was evaporated in vacuo and crude was purified by silica chromatography in a 0-5% MeOH gradient in DCM to yield 47 as a white solid (75%). $^{1H\ NMR}$ (CDCl$_3$): δ 7.65 (s, 1H), 7.56 (s, 1H), 7.32-7.26 (m, 5H), 6.74 (s (broad), 1H, NH), 5.32 (d, 1H, NH), 4.47 (dd, J=4 Hz, 2H), 4.43 (m, 2H), 4.11 (m, 1H), 2.47-2.2.40 (m, 1H), 2.33-2.26 (m, 1H), 1.42 (s, 9H).

Example 21: (S)—N-(1-(Benzylamino)-4-(1H-imidazol-1-yl)-1-oxobutan-2-yl) furan-2-carboxamide (48 or KP-301)

Compound 46 (1.40 mmol) was dissolved in a solution of anhydrous DCM with 30% TFA and stirred at 0° C. Reaction was monitored by TLC 95:5 DCM:MeOH until 46 was consumed. Reaction solvent was diluted with toluene and evaporated in vacuo to remove excess TFA to yield yellow crystalline solid (0.356 g, quantitative yield). This solid was then dissolved in 3 mL of anhydrous DCM to which DIPEA (1.84 mmol) were added and stirred at 0° C. 2-furoyl chloride (367.76 μmol) was added drop wise. Reaction was stirred 0° C. for 30 min and allowed to warm up to rt and stir for 12 hr. Reaction solvent was evaporated and resulting crude was dissolved in 15 mL of EtOAc and extracted with sat. NaHCO$_3$ (200 mL) dH$_2$O (until pH was neutralized), brine (200 mL), and dried over MgSO$_4$. Resulting crude was purified by silica chromatography in a 0-5% MeOH gradient in DCM to afford 48 as a yellow viscous solid (20%). $^{1H\ NMR}$ (CDCl$_3$) δ 8.41 (d, J=4 Hz, 2H), 7.69 (s, 1H), 7.47 (s, 1H), 7.28 (m, 5H), 7.09 (d, J=4 Hz, 1H), 6.92 (d, 1H), 6.50 (dd, J=4 Hz, 1H), 5.53 (d, 1H, NH) 4.72 (m, 1H), 4.40 (dd, J=4 Hz, 2H), 3.97 (m, 2H) 2.24-1.99 (m, 2H).

Example 22: (S)—N-(1-(Benzylamino)-1-oxo-4-(1H-1,2,3-triazol-1-yl)butan-2-yl)furan-2-carboxamide (49 or KP-313)

Compound 47 (1.196 mmol) was dissolved in 10 mL of anhydrous DCM with 30% TFA and stirred at 0° C. for 45 min. Reaction solvent was diluted with and evaporated to remove excess TFA to obtain a yellow viscous solid. Compound was then dissolved with DIPEA (3.53 mmol), were dissolved in 7 mL of anhydrous DCM and stirred at 0° C. for 45 min. 2-furoyl chloride (1.18 mmol), was added to reaction mixture dropwise and allowed to further stir at set temperature for 10 min. Reaction was stirred overnight, then concentrated and resulting crude was dissolved in 20 mL of EtOAc and was worked up. Resulting crude was purified by silica chromatography in a MeOH gradient in DCM to afford 26. $^{1H\ NMR}$ (CDCl$_3$): δ 7.77 (m, 1H, NH), 7.70 (d, J=7.2 Hz, 1H), 4.56 (s, 1H), 7.49 (d, J=4 Hz, 1H), 4.45 (s, 1H), 7.29-7.21 (m, 5H), 7.03 (dd, J=7.2 Hz, J=4 Hz, 1H), 6.48 (s (broad), 1H, NH), 4.70 (m, 1H), 4.49 (dd, J=4 Hz, 2H), 4.45 (m, 2H), 2.38-2.33 (m, 1H), 2.43-2.36 (m, 1H).

Examples 23-35 refer to the compounds and numbering found in Scheme 4:

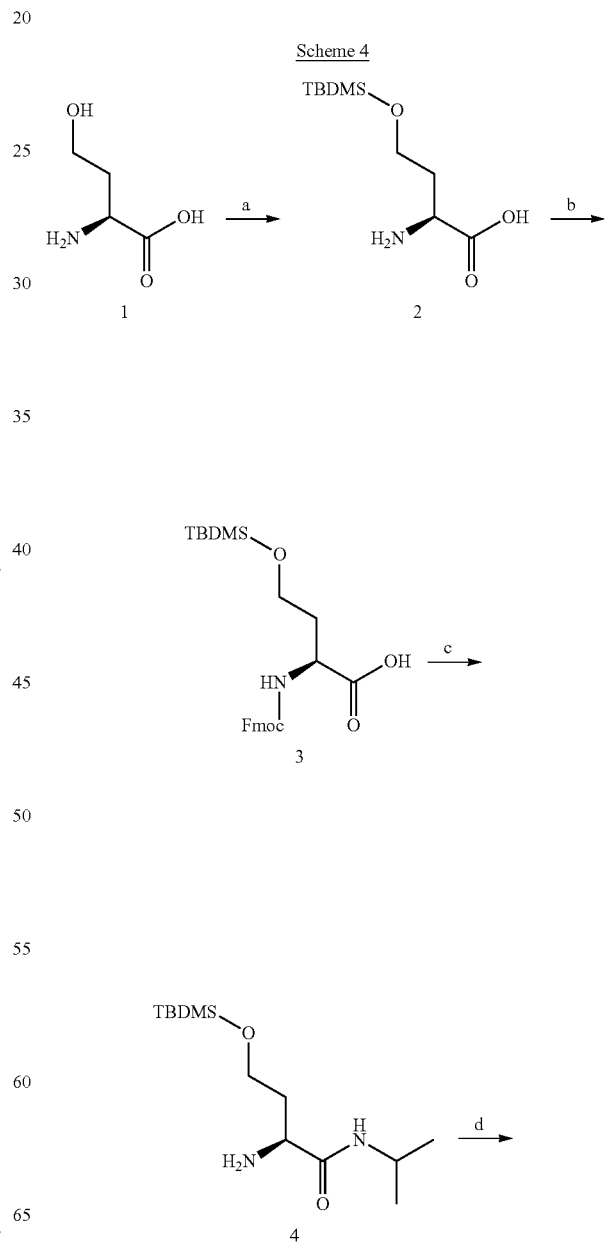

Scheme 4

-continued

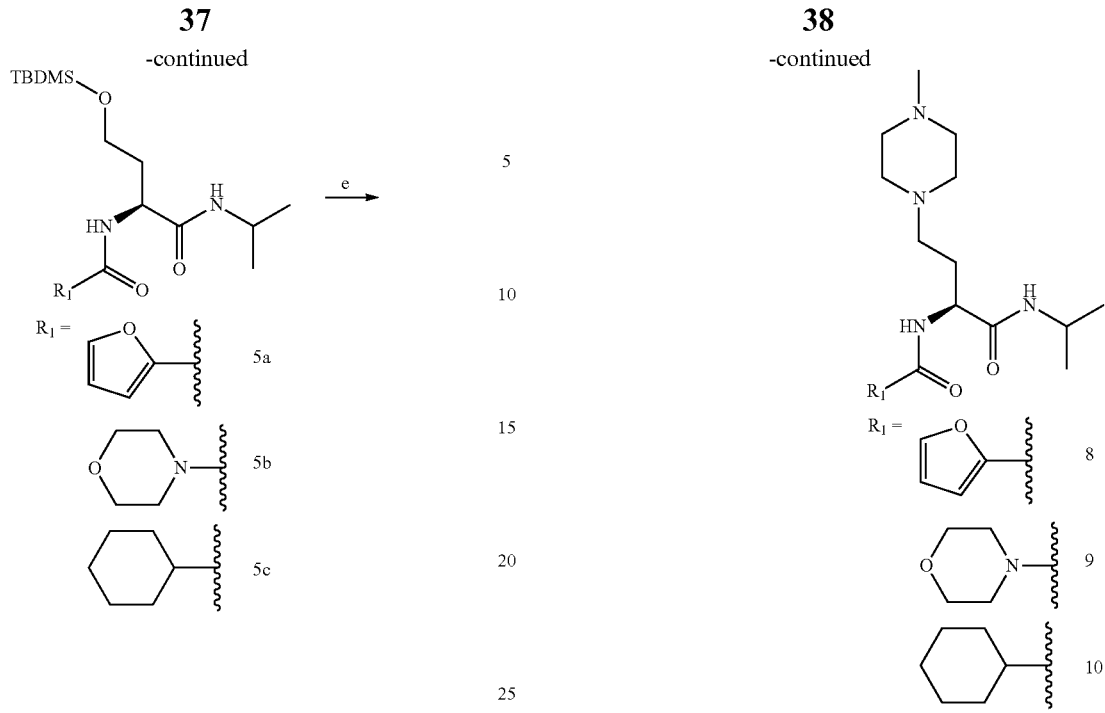

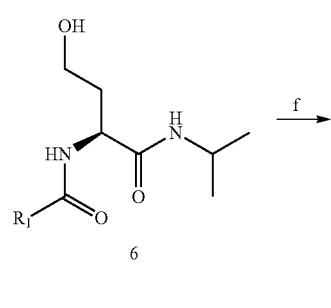

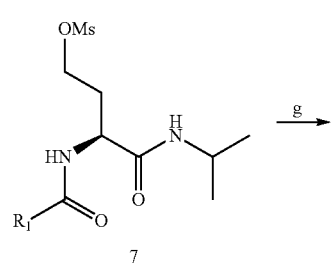

-continued

Reagents and conditions: (a) DBU (1.0 eq), TBDMSCl (1.5 eq), MeCN$_{(anh)}$, N$_2$ atm, rt, 16 hr; (b) Fmoc-Osu (1.1 eq), Et$_3$N (1.5 eq), 50:50 MeCN: H$_2$O, rt, 4 hr; (c) HATU (1.1 eq), DIPEA (3.0 eq), isopropylamine (10.0 eq), DMF$_{(anh)}$, N$_2$ atm, 0° C.→rt, 16 hr; (d) R$_1$COCl (1.0 eq), DIPEA (3.0 eq), DCM$_{(anh)}$, N$_2$ atm, 0° C.→rt, 2-5 hr; (e) TBAF (1.0 eq), THF$_{(anh)}$, N$_2$ atm, 0° C.-rt, 2 hr; (f) MsCl (1.0 eq), DIPEA (3.0 eq), DCM$_{(anh)}$, N$_2$ atm, 0° C., 2 hr; (g) N-methyl piperazine (1.0 eq), DIPEA (1.5 eq), DMF$_{(anh)}$, N$_2$ atm, 0° C.→rt, 16 hr.

Scheme 4 begins with the protection of the primary alcohol of L-homoserine by silylation with TBDMSCl and followed by amino protection with Fmoc carbamate to afford intermediate 3. Treatment of 3 with excess isopropylamine under HATU amino acid coupling conditions afforded intermediate 4 which was then treated with three different acyl chlorides to afford the respective intermediates 5a-5c. Desilylation followed by mesylation and direct substitution with N-methyl piperazine afforded compounds 8 (or KP-289), 9 (or KP-287), and 10 (or KP-295) with yields varying from 25-30%.

Example 23:
O-(tert-Butyldimethylsilyl)-L-Homoserine (2)

L-homoserine (1 g, 8.4 mmol) and DBU (1.32 mL, 8.8 mmol) were dissolved in 20 mL of anhydrous MeCN and stirred at 0° C. Tertbutyldimethysilyl chloride (1.32 g, 8.8 mmol) was dissolved in 20 mL of MeCN and added dropwise over 5 min. The reaction mixture was warmed to rt and stirred for 16 hr. A white precipitate formed and was washed with MeCN (200 mL), cold H2O (200 mL) and Et2O (200 mL), and dried under vacuum to afford 2 as a white powder (1.45 g, 78%). 1H NMR (CD3OD) δ 3.87 (t, J=6 Hz, 2H), 3.71-3.68 (m, 1H), 2.21-1.93 (m, 2H), 0.93 (s, 9H), 0.12 (s, 6H). 13C NMR (CD3OD) δ 61.9, 54.7, 34.4, 26.4, −5.4; m.p: 148-153° C.

Example 24: N-(((9[H]-Fluoren-9-yl) methoxy) carbonyl)-O-(tert-butyldimethylsilyl)-L-homoserine (3)

To a solution of 2 (1.45 g, 6.2 mmol) in 100 mL of 5% NaHCO3 (w/v) in 50% MeCN/H2O, Fmoc-O-succinimide (2.30 g, 6.8 mmol) was added. The reaction mixture was stirred at rt and monitored by TLC in 100% EtOAc until consumption of 2 was observed. Reaction solvent was removed in vacuo and the remaining suspension was acidified to pH 2.0 with 10% citric acid. Aqueous layer was extracted in EtOAc (3×200 mL) and dried over MgSO4. Resulting crude was purified by silica chromatography in a 5-40% EtOAc gradient in hexanes to afford 3 as a viscous white semi-solid (2.41 g, 82%). 1H NMR (CDCl3) δ 7.57 (d, J=7.6 Hz, 2H), 7.60 (t, J=6 Hz, 2H), 7.39 (t, J=7.6 Hz, 2H), 7.30 (t, J=7.2 Hz, 2H), 6.15 (d, J=7.2 Hz, 2H), 4.21 (t, J=6.8 Hz, 2H), 3.82 (t, 2H), 2.18-2.05 (m, 2H), 0.91 (s, 9H), 0.09 (s, 6H). 13C NMR (CDCl3) δ 156.4, 143.9, 141.4, 127.8, 127.2, 125.2, 120.1, 67.3, 60.7, 53.1, 47.3, 33.5, 25.9, 18.3, −5.5.

Example 25: (S)-2-Amino-4-((tert-Butyldimethylsilyl)oxy)-N-isopropylbutanamide (4)

Compound 3 (1.64 g, 3.6 mmol) was dissolved in 5 mL of anhydrous DMF to which DIPEA (1.88 mL, 10.8 mmol) and HATU (1.51 g, 3.6 mmol) were added and stirred at 4° C. Isopropylamine (4.56 mL, 36.0 mmol) was added drop wise to reaction mixture and further stirred at 4° C. Reaction was monitored by TLC in 7:3 EtOAc: Hexanes, until the complete deprotection of Fmoc was achieved. Reaction solvent was evaporated and crude was dissolved in 15 mL of DCM, washed with H2O (200 mL), brine (200 mL), and dried over MgSO4. Resulting crude was purified by silica chromatography in 30-100% EtOAc gradient in hexanes to afford 4 as yellow oil (0.39 g, 75%). 1H NMR (CDCl3) δ 6.68 (m, 1H, NH), 6.15 (m, 1H, NH), 4.10 (m, 1H), 4.03 (septet, 1H), 3.75 (m, 2H), 1.97 (m, 1H), 1.95 (m, 1H), 1.13 (d, J=6 Hz, 6H), 0.91 (s, 9H), 0.075 (d, J=4 Hz, 6H). 13C NMR (CDCl3) δ 170.3, 59.5, 51.1, 40.6, 38.2, 30.7, 25.8, 22.2, 22.1, −5.4.

Example 26: (S)—N-(4-((tert-Butyldimethylsilyl)oxy)-1-(isopropylamino)-1-oxobutan-2-yl)furan-2-carboxamide (5a)

Compound 4 (0.36 g, 1.46 mmol) was dissolved in 5 mL of anhydrous DCM to which DIPEA (762 µL, 4.38 mmol) was added and stirred at 0° C. 2-furoyl carbonyl chloride (215 µL, 2.19 mmol) was added drop-wise to mixture and further stirred at 0° C. for 3 hr. Reaction solvent was evaporated and resulting crude was dissolved in DCM (30 mL) and extracted with sat. NaHCO3 (200 mL), H2O (until pH was neutralized), and brine (200 mL), and dried over MgSO4. Resulting crude was purified by silica chromatography in a 0-5% MeOH gradient in DCM to afford 5a as yellow viscous semi-solid (0.14 g, 49%). 1H NMR (CDCl3) δ 7.77 (d, J=8 Hz, 1H), 7.12 (d, J=4 Hz, 1H), 6.70 (d, J=8 Hz, 1H), 6.50 (brs, 1H, NH), 4.73 (m, 1H), 4.09 (septet, 1H), 3.92 (m, 1H), 3.81 (m, 1H), 2.16 (m, 1H), 2.06 (m, 1H), 1.12 (d, J=4 Hz, 6H), 0.93 (s, 9H), 0.105 (d, J=4 Hz, 6H). 13C NMR (100 MHz, CDCl3) δ 170.0, 158.3, 147.7, 144.1, 114.6, 112.2, 61.0, 51.7, 41.6, 34.4, 26.0, 22.6, 18.4, −5.3.

Example 27: (S)—N-(4-((tert-Butyldimethylsilyl)oxy)-1-(isopropylamino)-1-oxobutan-2-yl)morpholine-4-carboxamide (5b)

Compound 4 (0.33 g, 1.20 mmol) was dissolved in 5 mL of anhydrous DCM to which DIPEA (1.05 mL, 6 mmol) were added and stirred at 0° C. Morpholine carbonyl chloride (210 µL, 1.8 mmol) was added drop-wise to the reaction at 0° C. The reaction was monitored as per the procedure described for compound 5a. Target compound 5b was obtained as a white semi-solid (0.245 g, 53%). 1H NMR (CDCl3) δ 6.71 (brs, 1H, NH), 6.02 (m, 1H, NH), 4.41 (q, 1H), 4.04 (dq, 1H), 3.85 (m, 1H), 3.75 (m, 1H), 3.67 (m, 4H), 3.37 (m, 4H), 1.99 (m, 1H), 1.92 (m, 1H), 1.15 (d, J=4 Hz, 6H), 0.91 (s, 9H), 0.085 (d, J=4 Hz, 6H). 13C NMR (CDCl3) δ 171.4, 157.5, 66.5, 61.4, 53.0, 44.5, 44.1, 35.3, 26.1, 22.8, 18.5, −5.1.

Example 28: (S)—N-(4-((tert-Butyldimethylsilyl)oxy)-1-(isopropylamino)-1-oxobutan-2-yl)cyclohexanecarboxamide (5c)

Compound 4 (0.33 g, 1.20 mmol) was dissolved in 5 mL of anhydrous DCM to which DIPEA (1.05 mL, 6 mmol) was added and stirred at 0° C. Cyclohexyl carbonyl chloride (240 µL, 1.8 mmol) was added drop-wise at 0° C. The reaction was monitored as per procedure described for 5a to obtain the target compound. Compound 5c was obtained as a white solid (0.2 g, 45%). 1H NMR (CDCl3) δ 6.61 (brs, 1H, NH), 5.85 (brs, 1H, NH), 4.40 (q, 1H), 4.05 (dq, 1H), 3.89 (m, 1H), 3.77 (m, 1H), 3.33 (m, 4H), 2.03 (m, 1H), 1.91 (m, 1H), 1.59-1.54 (m, 6H), 1.12 (d, J=4 Hz, 6H), 0.91 (s, 9H), 0.085 (d, J=4 Hz, 6H). 13C NMR (CDCl3) δ 171.6, 157.3, 61.4 53.0 47.8 44.8 41.2 34.8 25.9 25.5 24.3, 22.6, 22.5, −5.3. m.p: decomposes at 310° C.

Example 29: (S)—N-(4-Hydroxy-1-(isopropylamino)-1-oxobutan-2-yl) furan-2-carboxamide (6a)

Compound 5a (0.14 g, 379.87 µmol) was dissolved in 5 mL of anhydrous THF to which TBAF (165 µL, 569.81 µmol) was added and reaction was stirred at 0° C. for 30 min. Reaction solvent was evaporated and resulting crude purified by silica chromatography in 0-10% MeOH gradient in DCM to yield 6a as a yellow viscous semi-solid (0.075 g, 81%). 1H NMR (CDCl3) δ 7.53 (d, J=7.2 Hz, 1H), 7.45 (m, 1H, NH), 7.13 (d, 1H), 6.75 (d, J=7.3 Hz, 1H), 6.51 (m, 1H, NH), 4.75 (m, 1H), 4.08 (septet, 1H), 3.72 (m, 2H), 2.09 (m, 1H), 1.83 (m, 1H), 1.16 (d, J=4 Hz, 6H).

Example 30: (S)—N-(4-Hydroxy-1-(isopropylamino)-1-oxobutan-2-yl) morpholine-4-carboxamide (6b)

Compound 6b was synthesized from 5b (0.245 g, 632.11 µmol) following reaction procedure described for 6a. Compound 6b was afforded as a white solid (0.103 g, 63%). 1H NMR (CDCl3) δ 6.04 (d, 1H, NH), 5.75 (m, 1H, NH), 4.45 (septet, 1H), 4.21 (brs, 1H, OH), 4.05 (m, 1H) 3.69 (m, 6H), 3.34 (m, 4H), 1.97 (m, 1H), 1.65 (m, 1H), 1.17 (d, J=4 Hz, 6H). 13C NMR (CDCl3) δ 171.4, 157.5, 66.5, 61.4, 53.0, 44.5, 44.1, 35.3, 26.1, 22.8, 18.5, −5.1. m.p: decomposes at 210° C.

Example 31: (S)—N-(4-Hydroxy-1-(isopropylamino)-1-oxobutan-2-yl) cyclohexanecarboxamide (6c)

Compound 6c was synthesized from 5c (0.2 g, 519.98 µmol) following procedure described for synthesis of 6a. Compound 6c was afforded as a white semi-solid (0.11 g, 78%). 1H NMR (CDCl3) δ 6.61 (d, 1H, NH), 5.85 (d, 1H, NH), 4.40 (q, 1H), 4.05 (dq, 1H), 3.89 (m, 1H), 3.77 (m, 1H), 3.33 (m, 4H), 2.03 (m, 1H), 1.91 (m, 1H), 1.59-1.54 (m, 6H), 1.12 (d, J=4 Hz, 6H). 13C NMR (CDCl3) δ 171.6, 157.3, 61.40, 53.0, 47.8, 44.8, 41.2, 34.9, 25.9, 25.5, 24.3, 22.6.

Example 32: General Procedure for the Preparation of the Corresponding L-R1-Hse-OMs (7)

Corresponding compound 6a-6c (0.05 g) was dissolved in approximately 5 mL of anhydrous DCM to which DIPEA (3.0 eq) was added and stirred at 0° C. Methanesulfonyl chloride (2.5 eq) was added drop wise to the reaction at 0° C. Reaction was monitored by TLC in 95:5 DCM: MeOH until starting material was consumed. Solvent was evaporated and crude was dissolved in 10 mL of DCM, and washed with dilute NH4Cl (150 mL), brine (200 mL), and dried over MgSO4. Solvent was evaporated to afford the corresponding mesylate. Intermediates were used immediately for the next reaction without further purification.

Example 33: (S)—N-(1-(Isopropylamino)-4-(4-methylpiperazin-1-yl)-1-oxobutan-2-yl)furan-2-carboxamide (8; KP-289)

Compound 7a (0.05 g, 182.93 μmol) was dissolved in 2 mL of anhydrous DMF and stirred at 0° C. 1-methylpiperazine (18.15 μL, 163.62 μmol) was added drop wise at 0° C. and reaction was allowed to warm up 60° C. and stir for 2 hr. Upon reaction completion, solvent was removed in vacuo and resulting crude was dissolved in DCM (50 mL) and washed with H2O (150 mL), brine (150 mL) and dried over MgSO4. Crude was purified by silica chromatography in a gradient of 0-10% MeOH in DCM to afford 8 as a clear viscous semi-solid (0.019 g, 25%). 1H NMR (CDCl3) δ 7.89 (brs, 1H, NH), 7.49 (d, J=8 Hz, 1H), 7.16 (d, J=4 Hz, 1H) 6.78 (m, 1H, NH), 6.52 (dd, J=8 Hz, J=4 Hz, 1H) 4.47 (m, 1H), 4.28 (m, 1H), 3.69 (m, 4H), 3.39 (m, 4H), 2.79 (m, 2H), 2.20 (m, 2H), 2.12 (s, 3H), 1.21 (d, J=4 Hz, 6H).

Example 34: (S)—N-(1-(Isopropylamino)-4-(4-methylpiperazin-1-yl)-1-oxobutan-2-yl)morpholine-4-carboxamide (9; KP-287)

Compound 9 was synthesized from 7b (0.14 g, 243.85 μmol) following reaction protocol described for 8. Compound 9 was obtained as a viscous clear semi-solid. (0.056 g, 27%). 1H NMR (CDCl3) δ 4.68 (m, 1H), 4.06 (septet, 1H), 2.73 (m, 2H), 2.43 (s, 3H), 2.37 (m, 8H), 1.12 (d, J=4 Hz, 6H).

Example 35: (S)—N-(1-(Isopropylamino)-4-(4-methylpiperazin-1-yl)-1-oxobutan-2yl) cyclohexanecarboxamide (10; KP-295)

Compound 10 (0.05 g, 80.4 μmol) was synthesized from 7c following procedure described for synthesis of 8. Compound 10 was as a white solid (0.006 g, 30%). 1H NMR (CDCl3) δ 6.13 (d, 1H, NH), 4.54 (m, 1H), 4.19 (m, 1H), 4.125 (q, 2H), 2.85 (m, 1H), 2.17 (m, 1H), 2.14 (s, 3H), 1.91-1.37 (m, 10H), 1.23 (d, J=4 Hz, 6H). m.p.: 418-420° C.

Examples 36-45 refer to the compounds and numbering found in Scheme 5:

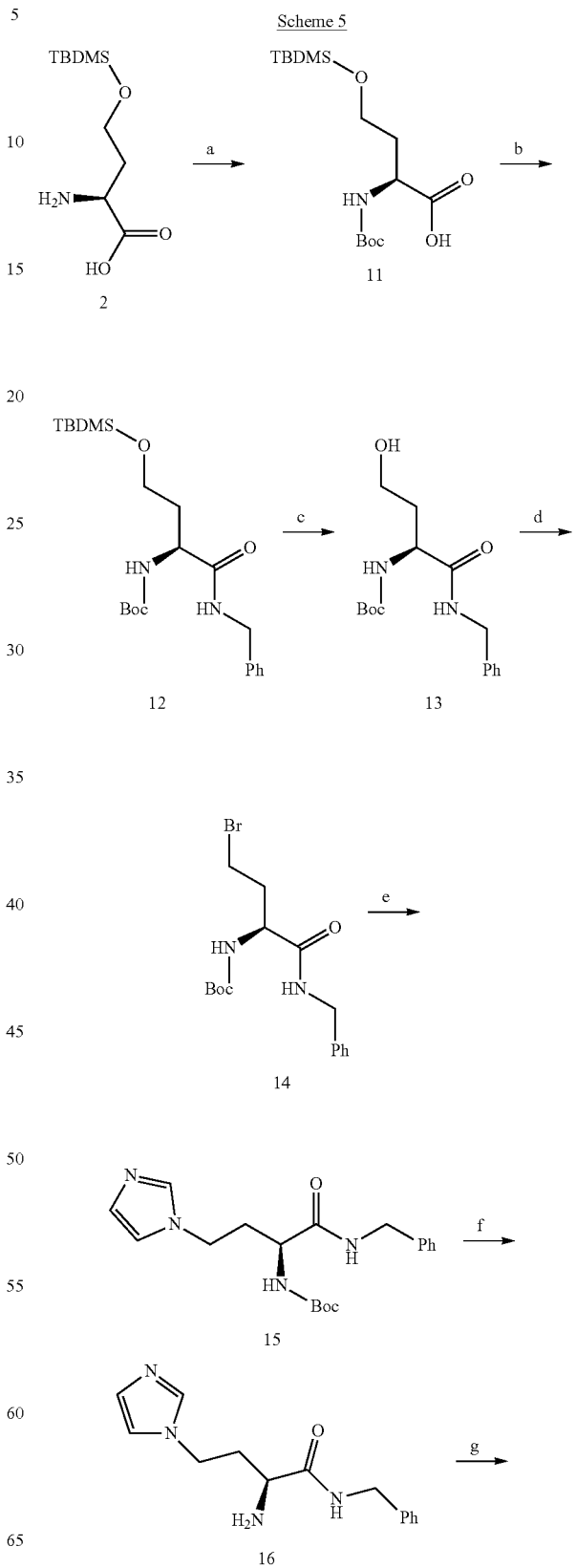

-continued

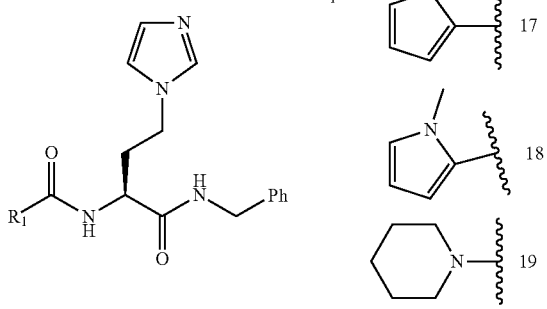

$R_1 =$ 17 (furan), 18 (N-methylpyrrole), 19 (piperidine)

Reagents and conditions: (a) Boc₂O (1.1 eq), Et₃N (1.5 eq), 50:50 MeCN:H₂O, rt, 4 hr; (b) HATU (1.10 eq), DIPEA (3.0 eq), benzylamine (1.1 eq), DMF$_{(anh)}$, N₂ atm, 0° C.→rt, 16 hr; (c) TBAF (1.0 eq), THF$_{(anh)}$, N₂ atm, 0° C.→rt, 2 hr; (d) CBr₄ (1.5 eq), PPh₃ (1.5 eq), DCM$_{(anh)}$, N₂ atm, 0° C.→rt, 2.5 hr; (e) imidazole (2.5 eq), DIPEA (1.5 eq), DMF$_{(anh)}$, N₂ atm, 0° C.→rt, 16 hr; (f) 30% TFA, DCM$_{(anh)}$, N₂ atm, 0° C., 45 min; (g) for R₂COCl:DIPEA (3.0 eq), DCM$_{(anh)}$, N₂ atm, 0° C., 4 hr; for R₂COOH:HATU (1.1 eq), DIPEA (3.0 eq), MeCN$_{(anh)}$, N₂ atm, 0° C.→rt, 16 hr.

N-imidazole substituted inhibitors were obtained by following Scheme 5, as attempts to synthesize these compounds from a mesylate intermediate showed to be unfavourable and the β, γ-unsaturated by-product. Amino protection of intermediate 2 was done with Boc instead of Fmoc due to the instability of the latter to the desilylation conditions normally used, and intermediate 11 was afforded. Coupling under HATU conditions with benzylamine was carried instead of isopropylamine due to the difficulties presented during bromination in the presence of this functional group and intermediate 13 was afforded. Desilylation and bromination with carbon tetrabromide and triphenylphosphine afforded intermediate 14. Substitutions of N-imidazole was optimized when 1H-imidazole was treated with one equivalent of DIPEA and stirred for one hour in DMF at 0° C. and added drop-wise to intermediate 14 to afford 15 in 65% yield. Treatment of 15 with TFA afforded amino 16 which was reacted with three different acyl chlorides and carboxylic acids to afford compounds 17 (or KP-301), 18 (or KP-302), and 19 (or KP-303) in 25-35% yields.

Example 36: N-(tert-Butoxycarbonyl)-O-(tert-butyldimethylsilyl)-L-homoserine (11)

Compound 2 (2.36 g, 10.11 mmol) was dissolved in a 50 mL solution of 1:1 acetone: H2O. Et3N (2.12 mL, 15.17 mmol) and Boc-anhydride (2.43 g, 11.12 mmol) were added to reaction and stirred at rt for 6 hr. Reaction was monitored by TLC in 95:5 DCM: MeOH until 2 was completely consumed. Reaction solvent was evaporated in vacuo and remaining aqueous layer was acidified to pH 2.0 with 10% citric acid. The aqueous layer was extracted with EtOAc (3×200 mL) and dried over MgSO4. Compound 11 was obtained as a viscous clear oil (2.72 g, 81%). 1H NMR (CDCl3) δ 5.92 (d, 1H, NH), 4.33 (q, 1H), 3.81 (m, 2H), 2.07 (m, 2H), 1.441 (s, 9H), 0.910 (s, 9H), 0.08 (d, J=4 Hz, 6H).

Example 37: tert-Butyl (S)-(1-(benzylamino)-4-((tert-butyldimethylsilyl)oxy)-1-oxobutan-2-yl)carbamate (12)

Compound 11 (2.72 g, 8.16 mmol) was dissolved in 15 mL of anhydrous MeCN to which DIPEA (4.26 mL, 24.47 mmol) and HATU (3.41 g, 8.97 mmol) were added and stirred at 4° C. Benzylamine (980.0 μL, 8.97 mmol) was added dropwise to reaction mixture and further stirred at 4° C. for 6 hr. Reaction solvent was evaporated in vacuo and resulting crude was dissolved in 15 mL of EtOAc and extracted with H2O (150 mL), brine (150 mL), and dried over MgSO4. Crude was purified by silica chromatography in a 5-30% gradient of EtOAC in hexanes to afford 12 as clear oil (2.29 g, 85%). 1H NMR (CDCl3) δ 7.37 (m, 5H), 7.10 (d, 1H, NH), 6.20 (d, 1H, NH), 4.55 (dd, J=4 Hz, 2H), 4.41 (m, 1H), 3.85 (m, 2H), 2.12 (m, 2H), 1.52 (s, 9H), 0.99 (s, 9H), 0.15 (d, J=4 Hz, 6H).

Example 38: tert-Butyl (S)-(1-(benzylamino)-4-hydroxy-1-oxobutan-2-yl)carbamate (13)

Compound 12 (1.13 g, 2.67 mmol) was dissolved in 10 mL of anhydrous THF and stirred at 0° C. TBAF (774.17 μL, 2.67 mmol) was added drop wise to reaction mixture and further stirred 0° C. for 30 min. Reaction was monitored by TLC 3:2 EtOAc: Hexanes until 12 was consumed. Reaction solvent was removed and remaining crude was purified by silica chromatography in a 10-80% EtOAc gradient in hexanes to afford 13 as a white solid (0.680 g, 82%). 1H NMR (CDCl3) δ 7.59 (d, 1H, NH), 7.30-7.20 (m, 5H), 5.86 (d, 1H, NH), 4.38 (dd, J=4 Hz, 2H), 4.31 (m, 1H), 3.60 (m, 2H), 1.98-1.69 (m, 2H), 1.40 (s, 9H). m.p.: 330-333° C.

Example 39: tert-Butyl (S)-(1-(benzylamino)-4-bromo-1-oxobutan-2-yl)carbamate (14)

Compound 13 (0.25 g, 810.71 μmol) and carbon tetrabromide (0.318 g, 1.22 mmol) were dissolved in 10 mL anhydrous DCM and stirred at 0° C. Triphenylphosphine (0.403 g, 1.22 mmol) was dissolved in 5 mL of anhydrous DCM and added dropwise to the reaction mixture over a 5 min period. Reaction was stirred at 0° C. for 10 min and then allowed to warm to rt. Reaction was monitored by TLC in 3:7 EtOAc: Hexanes until 13 was consumed. Reaction solvent was evaporated and crude was purified by silica chromatography in a 10-40% EtOAc gradient in hexanes to afford 14 as a white powder (0.173 g, 58%). 1H NMR (CDCl3) δ 7.59 (d, 1H, NH), 7.22 (m, 5H), 6.09 (d, 1H, NH), 4.41 (dd, J=4 Hz, 2H), 4.31 (m, 1H), 3.39 (m, 2H), 2.42-2.14 (m, 2H), 1.40 (s, 9H). m.p.: 328-330° C.

Example 40: tert-Butyl(S)-(1-(benzylamino)-4-(1[H]-imidazol-1-yl)-1-oxobutan-2-yl)carbamate (15)

Compound 14 (0.52 g, 1.40 mmol) was dissolved in 3 mL of anhydrous DMF and stirred at 0° C. A solution of imidazole (0.238 g, 3.50 mmol) and DIPEA (365.94 μL, 2.10 mmol) in DMF was added drop wise to bromide mixture and further stirred at 0° C. Reaction was monitored by TLC in 9:1 DCM: MeOH until 14 was consumed. Reaction solvent was evaporated in vacuo and resulting crude was dissolved in EtOAc (100 mL) and extracted with H2O (300 mL) and brine (300 mL), and dried over MgSO4. Resulting crude was purified by silica chromatography in a 30-70% EtOAc gradient in hexanes and then in a 0-10% MeOH gradient in DCM to yield 15 as a yellow semi-solid (0.38 g, 76%). 1H NMR (CDCl3) δ 8.17 (s, 1H), 7.32 (d, J=4 Hz, 1H), 7.21 (m, 5H), 6.87 (d, J=4 Hz, 1H), 5.94 (d, 1H, NH), 4.38 (dd, J=4 Hz, 2H), 4.22 (m, 1H), 3.97 (m, 2H) 2.24-1.99 (m, 2H), 1.43 (s, 9H).

Example 41: (S)-2-Amino-N-benzyl-4-(1[H]-imidazol-1-yl)butanamide (16)

Compound 15 (0.38 g, 1.40 mmol) was dissolved in a solution of anhydrous DCM with 30% TFA and stirred at 0°

C. Reaction was monitored by TLC in 95:5 DCM: MeOH until 15 was consumed. Reaction solvent was diluted with toluene and evaporated in vacuo to remove excess TFA to yield 16 as yellow crystalline solid (0.356 g, quantitative yield).

Example 42: (S)—N-(1-(Benzylamino)-4-(1[H]-imidazol-1-yl)-1-oxobutan-2-yl) furan-2-carboxamide (17; KP-301)

Compound 16 (0.095 g, 367.76 mol) was dissolved in 3 mL of anhydrous DCM to which DIPEA (320.29 µL, 1.84 mmol) was added and stirred at 0° C. 2-furoyl chloride (36.26 µL, 367.76 µmol) was added dropwise at 0° C. Reaction was stirred at 0° C. for 30 min and allowed to warm up to rt and stir for 12 hr. Reaction solvent was evaporated and resulting crude was dissolved in 15 mL of EtOAc and extracted with sat. NaHCO3 (200 mL), H2O (until pH was neutralized), brine (200 mL), and dried over MgSO4. Resulting crude was purified by silica chromatography in a 0-5% MeOH gradient in DCM to afford 17 as a yellow viscous semi-solid (0.025 g, 20%). 1H NMR (CDCl3) δ 8.41 (d, J=4 Hz, 2H), 7.69 (s, 1H), 7.47 (s, 1H), 7.28 (m, 5H), 7.09 (d, J=4 Hz, 1H), 6.92 (d, 1H), 6.50 (dd, J=4 Hz, 1H), 5.53 (d, 1H, NH) 4.72 (m, 1H), 4.40 (dd, J=4 Hz, 2H), 3.97 (m, 2H) 2.24-1.99 (m, 2H).

Example 43: (S)—N-(1-(Benzylamino)-4-(1[H]-imidazol-1-yl)-1-oxobutan-2-yl) piperidine-1-carboxamide (18; KP-302)

Compound 16 (0.095 g, 367.7 µmol) was dissolved in 3 mL of anhydrous DCM to which DIPEA (320.29 µL, 1.84 µmol) was added and stirred at 0° C. 1-piperidine carbonyl chloride (46 µL, 367.76 µmol) was added dropwise at 0° C. and stirred at rt for 4 hr. Reaction solvent was evaporated in vacuo and crude was dissolved in 10 mL EtOAc and extracted with H2O (100 mL) and brine (100 mL), and dried over MgSO4. Resulting crude was purified by silica chromatography 0-10% MeOH gradient in DCM to afford 18 as a white semi-solid (0.120 g, 65%). 1H NMR (CDCl3) δ 7.82 (s, 1H), 7.57 (d, 1H, NH), 7.33 (m, 5H), 6.59 (d, 1H, NH), 4.40 (dd, J=4 Hz, 2H), 4.29 (m, 1H), 3.66 (m, 2H), 3.6 (m, 2H), 2.50 (m, 1H), 2.23 (m, 1H), 1.74 (p, 4H), 1.54 (m, 2H).

Example 44: (S)—N-(1-(Benzylamino)-4-(1[H]-imidazol-1-yl)-1-oxobutan-2-yl)-1-methyl-1[H]-pyrrole-2-carboxamide (19; KP-303)

N-methylpyrrole-2-carboxylic acid (0.046 g, 367.76 µmol) was dissolved in 2 mL of anhydrous DMF to which DIPEA (320.29 µL, 1.84 mmol) and HATU (0.139 g, 367.76 µmol) were added and stirred at 0° C. for 20 min. Compound 16 (0.095 g, 367.76 µmol) was dissolved in 1 mL of DMF and added to reaction mixture and stirred for 1 hr at 0° C. and then warmed to rt and stirred for 12 hr. Reaction solvent was evaporated and crude was dissolved in 50 mL EtOAc and extracted with H2O (100 mL) and brine (100 mL), and dried over MgSO4. Resulting crude was purified by silica chromatography in a 0-15% MeOH gradient in DCM to afford 19 as a white semi-solid (0.02 g, 27%). 1H NMR (CDCl3) δ 8.18 (s, 1H), 7.53 (d, J=8 Hz, 1H), 7.35 (s, 1H), 7.34 (d, J=4 Hz, 1H), 7.27 (m, 5H), 7.08 (d, J=4 Hz, 1H), 6.92 (s, 1H), 6.74 (s, 1H), 6.09 (d, 1H, NH), 5.54 (d, 1H), 4.63 (m, 1H), 4.40 (dd, J=4 Hz, 2H), 4.00 (m, 2H), 3.88 (s, 3H), 2.24-1.99 (m, 2H). 13C NMR (CDCl3) δ 179.4, 171.1, 162.2, 138.1, 128.8, 127.7, 127.6, 113.1, 107.7, 50.2, 43.62, 3.91, 34.3.

Example 45: (S)—N-(4-(1[H]-imidazol-1-yl)-1-(isopropylamino)-1-oxobutan-2-yl) furan-2-carboxamide (20; KP-286)

A solution of imidazole (0.0536 g, 788.20 µmol) and DIPEA (0.0612 g, 472.92 µmol) in 2 mL of anhydrous DMF was prepared and stirred at rt for 30 min. Compound 5a (0.1 g, 315.28 µmol) was dissolved in 1 mL of anhydrous DMF and added drop wise to pre-stirring mixture at 0° C. Reaction was monitored by TLC in 3:1 EtOAc: hexanes until 5a was consumed. Reaction solvent was evaporated in vacuo and resulting crude was dissolved in 50 mL of EtOAc and washed with H2O (100 mL), and brine (100 mL), and dried over MgSO4. Resulting crude was purified by silica chromatography in a 30-100% EtOAc gradient in hexanes to afford 20 as a yellow viscous semi-solid (0.025 g, 35%). 1H NMR (CDCl3) δ 7.89 (s, 1H), 7.70 (s, 1H), 7.49 (d, J=7.2 Hz, 1H), 7.19 (d, J=4 Hz, 1H), 7.14 (d, J=7.3 Hz, 1H), 7.03 (d, 1H, NH), 6.78 (m, 1H, NH), 6.52 (dd, J=7.2 Hz, J=7.3 Hz, 1H), 6.15 (d, 1H, NH), 4.59 (m, 1H), 4.11 (m, 2H) 4.08 (m, 1H), 2.41 (m, 1H), 2.21 (m, 1H), 1.18 (d, J=4 Hz, 6H). 13C NMR (CDCl3) δ 171.3, 161.3, 137.8, 133.1, 128.7, 128.1, 126.0, 120.6, 113.3, 111.8, 50.3, 43.2, 38.5, 35.8. (S)—N-(4-(4-(Cyanomethyl)-1[H]-imidazol-1-yl)-1-(isopropylamino)-1-oxobutan-2-yl)furan-2-carboxamide (21). Similarly, compound 21 (KP-288) was synthesized from 6a (0.14 g, 213.3 µmol) following procedure described for 20 to obtained compound 21 as a yellow-brown semi-solid (0.035 g, 27%). $^1$H NMR (CDCl$_3$) δ7.55 (s, 1H), 7.17 (d, J 7.2 Hz, 1H), 7.07 (d, 1H, NH), 7.03 (m, J 4 Hz, 1H), 6.54 (dd, J 7.2 Hz, J 4 Hz, 1H), 4.55 (m, 1H), 4.05 (m, 2H), 3.74 (m, 1H), 3.67 (s, 2H), 2.34 (m, 2H), 2.18 (m, 2H), 1.15 (d, J 4 Hz, 6H).

Examples 46-52 refer to the compounds and numbering in Scheme 6:

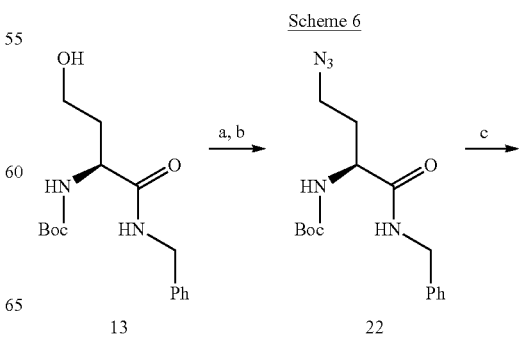

Scheme 6

-continued

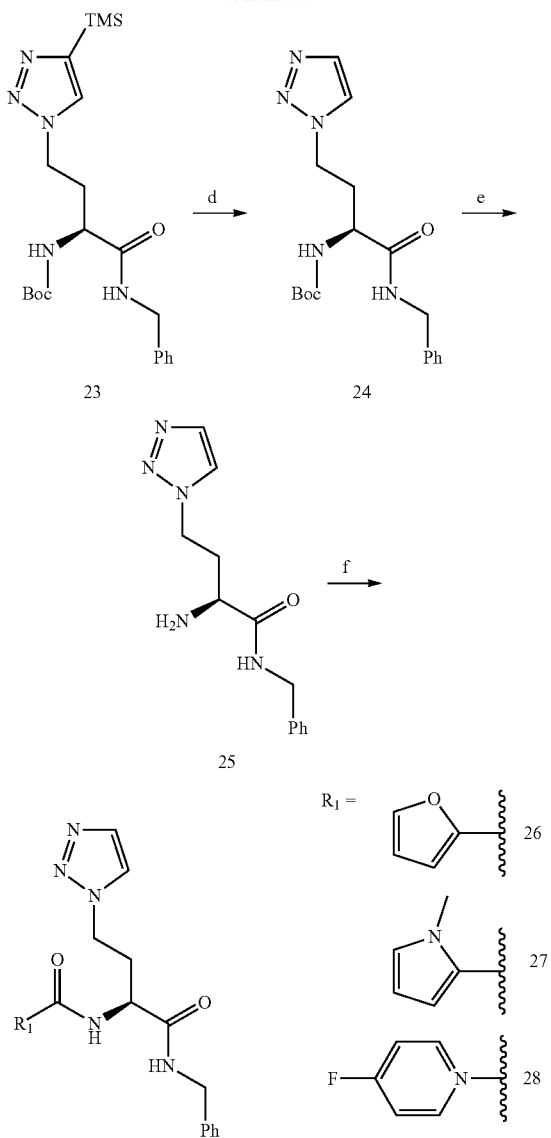

Reagents and conditions: a) MsCl (1.1 eq), DIPEA (3.0 eq), DCM$_{(anh)}$, N$_2$ atm, 0° C., 45 min; b) NaN$_3$ (4.0 eq), DMF$_{(anh)}$, N$_2$ atm, 60° C., 2.5 hr; c) CuI (1.0 eq), TEMED (1.0 eq), Et$_3$N (1.0 eq), TMS-acetylene (2.5 eq), THF$_{(anh)}$, N$_2$ atm, rt, 18 hr; d) TBAF (1.5 eq), THF$_{(anh)}$, 10% AcOH, N$_2$ atm, 0° C.→rt, 16 hr; e) 30% TFA, DCM$_{(anh)}$, N$_2$ atm, 0° C., 45 min; f) for R$_2$COCl:DIPEA (3.0 eq), DCM$_{(anh)}$, N$_2$ atm, 0° C., 4 hr; for R$_2$COOH:HATU (1.1 eq), DIPEA (3.0 eq), ACN$_{(anh)}$, N$_2$ atm, 0° C.→rt, 16 hr.

The synthesis of compounds 26-28 was carried using Scheme 6, as the direct substitutions of 1H, 2, 3- and 1H, 2, 4-triazoles with either a mesylate or a bromo intermediate were unsuccessful. Intermediate 13 was converted into azide intermediate 22, first by activation of the alcohol by mesylation, followed by treatment with sodium azide. The formation of 1H, 2, 3-triazole proceeded with the treatment of intermediate 22 with TMS-acetylene in the presence of a copper catalyst to afford 23 in 66% yield. The reaction mechanism for this triazole synthesis proceeds through a [1+3] Sharpless modified Huisgen cycloaddition mechanism. Desilytation and decarbamation yielded intermediated 24 which was coupled with the corresponding acyl chlorides and carboxylic acids to afford compounds 26 (or KP-314), 27 (or KP-313), and 28 (or KP-316) in 40-55% yields.

Example 46: tert-Butyl (S)-(4-azido-1-(benzylamino)-1-oxobutan-2-yl)carbamate (22)

Compound 13 (1.75 g, 5.67 mmol) was dissolved in 5 mL of anhydrous DCM and stirred at 0° C. DIPEA (2.97 mL, 17.02 mmol) and MsCl (483.16 μL, 6.24 mmol) were added dropwise and further stirred at 0° C. until 13 was consumed. Reaction solvent was then evaporated and crude was re-dissolved in 30 mL of EtOAc and washed with dilute NH4Cl (150 mL) and brine (150 mL), and dried over MgSO4. Organic layer was evaporated and resulting yellow solid was re-dissolved in 5 mL of anhydrous DMF. Sodium azide (1.47 g, 22.61 mmol) was added to reaction and stirred at 60° C. for 2.5 hr. Reaction solvent was evaporated and resulting crude was dissolved in 30 mL EtOAc and washed H2O (150 mL) and brine (150 mL), dried over MgSO4, and purified by silica chromatography in a 10-60% EtOAc gradient in hexanes to yield 22 as a clear viscous semi-solid (1.04 g, 55%). 1H NMR (CDCl3) δ 7.32-7.24 (m, 5H), 6.68 (brs, 1H, NH), 5.26 (d, 1H, NH), 4.40 (dd, J=4 Hz, 2H), 4.21 (septet, 1H), 3.41 (m, 2H), 2.09-2.01 (m, 1H), 1.96-1.92 (m, 1H), 1.42 (s, 9H).

Example 47: tert-Butyl (S)-(1-(benzylamino)-1-oxo-4-(4-(trimethylsilyl)-1[H]-1,2,3-triazol-1-yl)butan-2-yl)carbamate (23)

To a suspension of CuI (0.245 mg, 1.28 mmol) in 5 mL of anhydrous THF, TEMED (193 μL 1.28 mmol), Et3N (180 μL, 1.28 mmol), and TMS-acetylene (918 μL, 6.45 mmol) were added and stirred at rt. Compound 22 (0.860 g, 2.58 mmol) was dissolved in 10 mL of anhydrous THF and immediately added to reaction mixture and allowed to stir at rt for 18 hr. Reaction was quenched with H2O and extracted in 60 mL EtOAc. Organic layer was then washed with brine (150 mL) and dried over MgSO4. Resulting crude was purified by silica chromatography in a 30-60% EtOAc gradient in hexanes to afford 23 as a white semi solid (0.430 g, 62%). 1H NMR (CDCl3) δ 7.57 (s, 1H), 7.51 (m, 1H, NH), 7.28-7.19 (m, 5H), 5.87 (d, 1H, NH), 4.47 (dd, J=4 Hz, 2H), 4.39 (m, 2H), 4.30 (septet, 1H), 2.47-2.39 (m, 1H), 2.30-2.25 (m, 1H), 1.40 (s, 9H), 0.29 (s, 9H).

Example 48: tert-Butyl (S)-(1-(benzylamino)-1-oxo-4-(1[H]-1,2,3-triazol-1-yl)butan-2-yl)carbamate (24)

Compound 23 (0.7 g, 1.62 mmol) was dissolved in 10 mL of anhydrous THF containing 1M AcOH and stirred at 0° C. TBAF (470 μL, 1.62 mmol) was added at 0° C. and reaction was allowed to warm up to rt and stir for 16 hr. Reaction solvent was evaporated in vacuo and crude was purified by silica chromatography in a 0-5% MeOH gradient in DCM to yield 24 as a white semi-solid (0.435 g, 75%). 1H NMR (CDCl3) δ 7.65 (s, 1H), 7.56 (s, 1H), 7.32-7.26 (m, 5H), 6.74 (brs, 1H, NH), 5.32 (d, 1H, NH), 4.47 (dd, J=4 Hz, 2H), 4.43 (m, 2H), 4.11 (m, 1H), 2.47-2.2.40 (m, 1H), 2.33-2.26 (m, 1H), 1.42 (s, 9H).

Example 49: (S)-2-Amino-N-benzyl-4-(1[H]-1, 2,3-triazol-1-yl)butanamide (25)

Compound 24 (0.430 g, 1.196 mmol) was dissolved in 10 mL of anhydrous DCM with 30% TFA and stirred at 0° C. for 45 min. Reaction solvent was diluted with toluene and evaporated to remove excess TFA and afford 25 yellow viscous solid. Crude was used for next reaction without further purification (0.620 g, quantitative yield).

Example 50: (S)—N-(1-(Benzylamino)-1-oxo-4-(1[H]-1,2,3-triazol-1-yl)butan-2-yl)furan-2-carboxamide (26; KP-314)

Compound 25 (0.305 g, 1.18 mmol) and DIPEA (614.63 µL, 3.53 mmol) were dissolved in 7 mL of anhydrous DCM and stirred at 0° C. for 45 min. 2-furoyl chloride (116.31 µL, 1.18 mmol) was added to reaction mixture dropwise at 0° C. and allowed to further stir for 10 min. Reaction was allowed to warm up to rt and stir over 16 hr. Reaction solvent was evaporated and resulting crude was dissolved in 20 mL of EtOAc and washed sat NaHCO3 (200 mL), H2O (until pH was neutralized), brine (200 mL), and dried over MgSO4. Resulting crude was purified by silica chromatography in a 0-10% MeOH gradient in DCM to afford 26 as a light brown viscous semi-solid (75 mg, 45%). 1H NMR (CDCl3) δ 7.77 (m, 1H, NH), 7.70 (d, J=7.2 Hz, 1H), 4.56 (s, 1H), 7.49 (d, J=4 Hz, 1H), 4.45 (s, 1H), 7.29-7.21 (m, 5H), 7.03 (dd, J=7.2 Hz, J=4 Hz, 1H), 6.48 (brs, 1H, NH), 4.70 (m, 1H), 4.49 (dd, J=4 Hz, 2H), 4.45 (m, 2H), 2.38-2.33 (m, 1H), 2.43-2.36 (m, 1H). 13C NMR (CDCl3) δ 170.6, 157.9, 146.9, 143.8, 136.9, 129.2, 128.8, 126.7, 112.1, 111.1, 55.7, 46.8, 43.2, 30.1.

Example 51: (S)—N-(1-(Benzylamino)-1-oxo-4-(1[H]-1,2,3-triazol-1-yl)butan-2-yl)-1-methyl-1[H]-pyrrole-2-carboxamide (27; KP-313)

N-methylpyrrole-2-carboxylic acid (147.17 mg, 1.18 mmol) was dissolved in 3 mL of anhydrous DMF to which HATU (491.95 mg, 1.29 mmol) and DIPEA (614.63 µL, 3.53 mmol) were added and stirred at 0° C. for 45 min. Compound 25 (0.305 g, 1.18 mmol) was dissolved in 2 mL of DMF and added drop wise to mixture at 0° C. Reaction was allowed to warm to rt and stir for 16 hr. Reaction solvent was evaporated in vacuo and resulting crude was dissolved in 30 mL EtOAc and washed with H2O (200 mL) and brine (200 mL), and dried over MgSO4. Resulting crude was purified by silica chromatography in a 0-10% MeOH gradient in DCM to yield 27 as a white semi-solid (0.120 g, 62%). 1H NMR (CDCl3) δ 7.97 (s, 1H), 7.76 (d, J=7 Hz, 1H), 7.63 (s, 1H), 7.47 (d, J=4 Hz, 1H), 7.29-7.19 (m, 5H), 6.77 (d, J=7 Hz, 1H, NH), 6.05 (d, J=4 Hz, 1H), 5.30 (d, 1H, NH), 4.62 (septet, 1H), 4.52 (dd, J=4 Hz, 2H), 4.40 (m, 2H), 3.86 (s, 3H), 2.91-2.79 (m, 1H), 1.83-1.67 (m, 1H).

Example 52: (S)—N-(1-(Benzylamino)-1-oxo-4-(1[H]-1,2,3-triazol-1-yl)butan-2-yl)-4-fluorobenzamide (28; KP-316)

p-Fluorobenzoic acid (0.148 g, 1.0605 mmol), was dissolved in 5 mL of anhydrous DMF to which HATU (403.24 mg, 1.065 mmol) and DIPEA (510 µL, 2.892 mmol) were added and stirred at 0° C. for 45 min. Compound 25 (0.250 g, 0.964 mmol) was dissolved in 2 mL of DMF and added drop wise to mixture at 0° C. Reaction was allowed to warm to rt and stir for 16 hr. Reaction solvent was evaporated and resulting crude was dissolved in 30 mL of EtOAc and washed with H2O (200 mL), brine (200 mL), and dried over MgSO4. Resulting crude was purified by silica chromatography in a 0-10% MeOH gradient in DCM to yield 28 as a white solid (0.125 g, 62%). 1H NMR (CDCl3) δ 7.99 (t, 1H), 7.95 (t, 1H), 7.77 (td, 2H), 7.65 (d, 1H), 7.53 (s, 1H), 7.27-7.19 (m, 5H), 7.01 (td, 2H), 4.79 (septet, 1H), 4.46 (dd, J=4 Hz, 2H), 4.38 (d, 2H), 2.55-2.48 (m, 1H), 2.45-2.39 (m, 1H). 13C NMR (CDCl3) δ 170.9, 166.7, 163.7, 137.7, 129.7, 128.6, 127.5, 115.7, 115.4, 51.1, 46.9, 43.6, 33.3. 19F NMR (CDCl3) δ −107.14 (s, 1F). m.p.: 180-185° C.

Example 53: Inhibition of PAD Activity

Materials: PAD1, PAD2, PAD3 and PAD4 were purchased from commercial sources. Assay buffer: 50 mM Tris pH 7.5, 100 mM NaCl, 10 mM $CaCl_2$, 5 mM DTT. Color reagent: 1 volume of reagent A (80 mM diacetyl monoxime, 2 mM thiosemicarbazide) and 3 volumes of reagent B (17.35% v/v $H_3PO_4$, 33.7% v/v $H_2SO_4$, and 0.765 mg/mL ammonium iron (III) sulfate).

Figure 3:
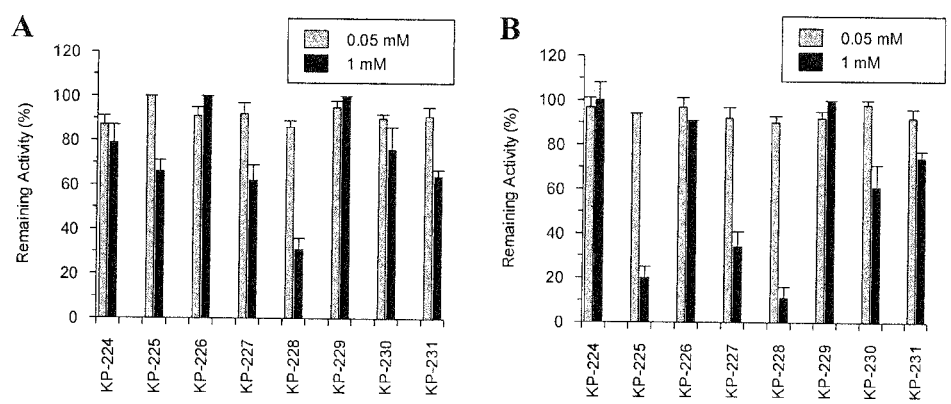
FIG. 3 is a bar graph showing the inhibition of (A) PAD1, and (B) PAD4 using compounds of the disclosure.
Figure 4:
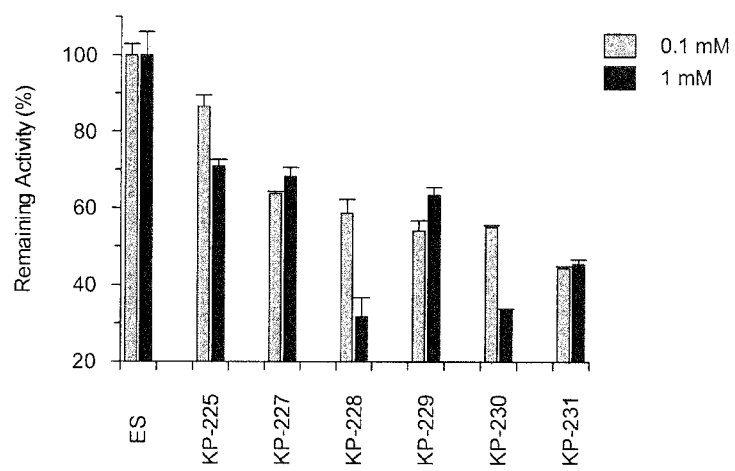
FIG. 4 is a bar graph showing the inhibition of mouse PAD2 using compounds of the disclosure.
Figure 5:
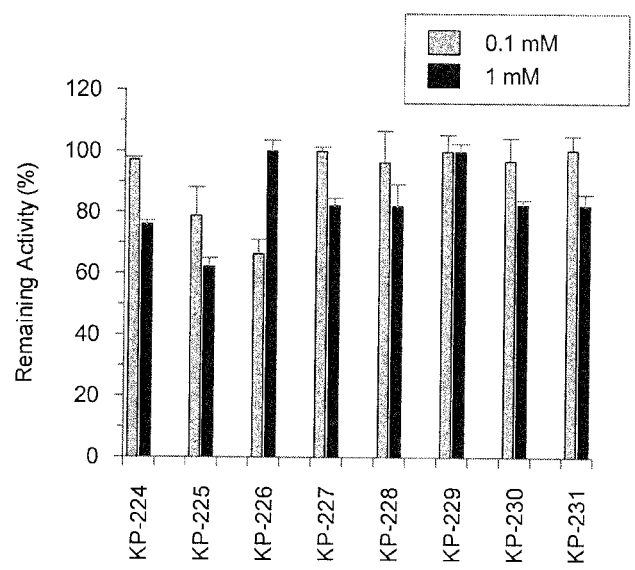
FIG. 5 is a bar graph showing the inhibition of human PAD4 using compounds of the disclosure.

The assays were conducted at 37° C. in the presence of each inhibitor in the concentration range of 1 to 1000 µM of each inhibitor tested. The inhibitor (12.5 µL of stock) was mixed with appropriate amount of substrate (BAEE) stock solution and preincubated at 37° C. for a period in the range of 0-60 min. The reaction was initiated by the addition of the enzyme. The reaction samples were incubated for a period in the range of 0-60 min. Color reagent was added (in the range of 50-300 µL/sample) and the samples were boiled for a period in the range of 0-45 min in a water bath. Samples were cooled on ice, vortexed and centrifuged. 200 µL aliquots were transferred to the 96-well plate and the absorbance was measured at 530 nm and the remaining activity was computed. Results for exemplary compounds of Formula I are shown in FIG. 3. The inhibition of PAD1 is shown in FIG. 3A while the inhibition of PAD4 is shown in FIG. 3B. The remaining activity data were plotted versus inhibitor concentration and fitted to the dose-response equation to calculate $IC_{50}$. Results for PAD1 for compounds of Formula I are shown in Table 1. Results for compounds of Formula I are shown in FIG. 4 and Table 2 for PAD2. Results for compounds of Formula I are shown in FIG. 5 and Tables 3 and 4, for PAD4. Results for PAD1, PAD2, and PAD4 for additional compounds of Formula I are shown in Table 5.

Example 54: Inhibition of PAD Activity (Table 6)

Human PAD1 and PAD4, and mouse PAD2 were purchased from SignalChem (Richmond, BC). Benzoyl Arginine Ethyl Ester (BAEE), DTT, diacetyl monoxime, thiosemicarbazide, and ammonium iron (III) sulfate were purchased from Sigma-Aldrich (Oakville, ON). Assay buffer: 100 mM Tris pH 7.5, 100 mM NaCl, 10 mM CaCl2, 5 mM DTT. Color reagent: 1 volume of reagent A (80 mM diacetyl monoxime, 2 mM thiosemicarbazide) and 3 volumes of reagent B (17.35% v/v H3PO4, 33.7% v/v H2SO4, and 0.765 mg/mL ammonium iron (III) sulfate). Experimental log P andpKa values were obtained using ChemBioDraw Ultra v. 13.0.

These inhibition studies of hPAD1, hPAD4, and mPAD2 were performed at 37° C. Assay buffer containing 5% DMSO was used to dissolve and dilute all tested inhibitors. The enzyme and substrate stock samples were also prepared in 5% DMSO/assay buffer. The inhibitor (12.5 µL of stock) was mixed with 25 µL enzyme and incubated at 37° C. for 30 min. Subsequently, 12.5 µL of 20 mM substrate was added and samples were returned to the incubator (37° C.) for additional 30 min. Control reaction with no inhibitor contained the same amount of DMSO as the inhibition samples. Final concentration of hPAD1, hPAD4 in the reaction mixture was 50 nM and PAD2 was 100 nM. Substrate concentration was 5 mM. The inhibitors were tested at 0.1, 0.5, 1, 2, 5, and 10 mM. After the 30 min incubation with substrate, the color reagent was added (200 µL/sample). Samples were boiled for 15 min in a water bath, cooled on ice, vortexed and briefly centrifuged. 200 µL aliquots were transferred to the 96-well plate and the absorbance was measured at 530 nm.

Enzymatic assays were carried with hPAD1, mPAD2 and hPAD4 and inhibition constants for the compounds were calculated along with experimental log P and pKa values (Table 6). Substitutions on the side chain amino acids as well as the groups on the amino and carboxy termini influenced the inhibitory activities of the synthesized PAD inhibitors. Compounds KP-301, KP-302, KP-303, KP-287 showed activity towards PADs ($K_i$>200-500 µM). Compounds KP-286, KP-288 carried the N-terminal furoyl moiety, the C-terminal isopropylamine, and the corresponding substituted imidazoles. KP-286 showed greater than 5-fold inhibitor efficacy for hPAD4 in comparison to hPAD1 and mPAD2 suggesting specificity and selectivity towards this isozyme. KP-288 showed at least 3-fold inhibitor efficacy towards hPAD1 in comparison to other isozymes. Substituted imidazole KP-302 and triazole KP-314 showed activities towards PADs ($K_i$<200 µM) with at least 2-fold selectivity towards mPAD2 in comparison to hPAD1 and hPAD4.

A SAR analysis was carried out to interpret the results from the inhibition data to elucidate on the effects of the side chains on overall inhibition as well as their implication in selectivity and specificity against the tested isozymes (Table 7). Selectivity was assessed by calculating the ratios of inhibition between each isozyme, for each isozyme, where ratios greater than 2-fold suggest selectivity.

Example 55: Studies on the MOG-EAE Mouse Model

MOG-EAE mouse model has been traditionally used as an autoimmune animal model of the multiple sclerosis disease in human.[51] A MOG-EAE mouse model (C57BL/6 mice, n=11) was used to investigate the efficacy of compounds of the application. Mice received a dose in the range of 1-150 mg/kg of the test compound q.d. (i.p.).

Figure 6:
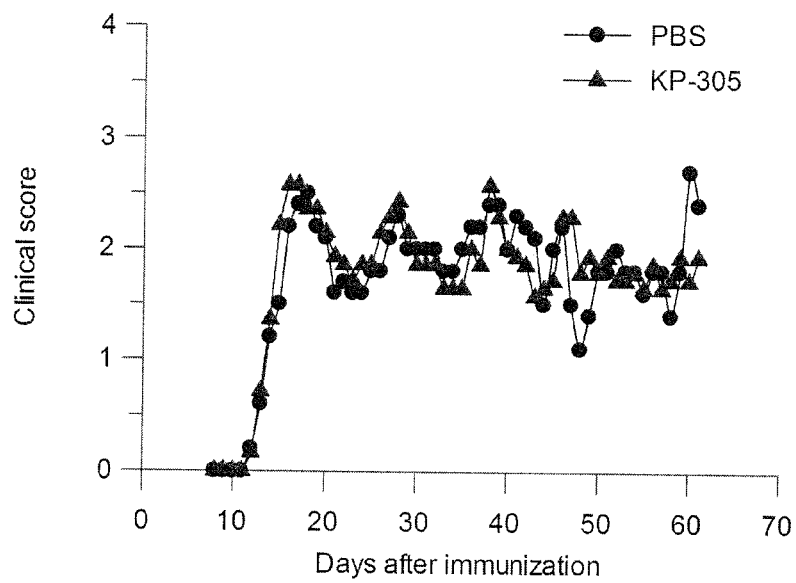
FIG. 6 is a graph showing the effect of compounds of the disclosure in an in vivo mouse model, EAE to study the efficacy of PAD inhibitors.
Figure 6:
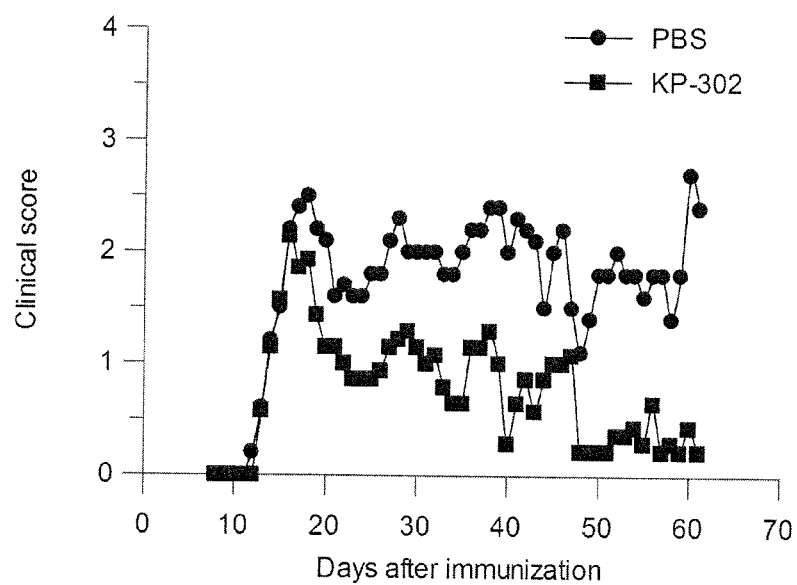
Figure 7:
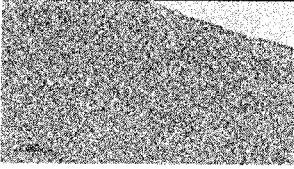
FIG. 7 shows the levels of PAD2 and citrullination in mouse cerebral cortex, corresponding to the study in FIG. 6.
Figure 7:
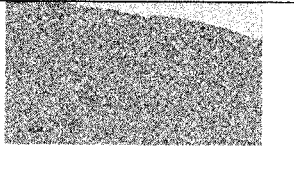
Figure 7:
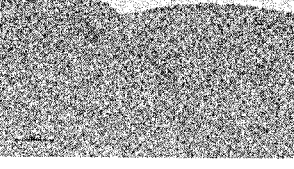
Figure 7:
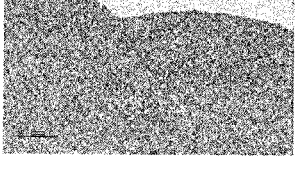
Figure 7:
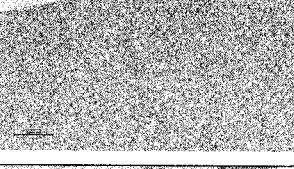
Figure 7:
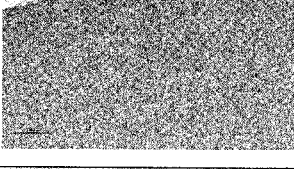
Figure 7:
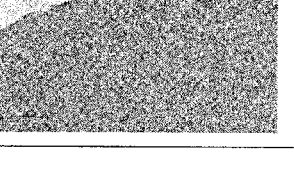
Figure 7:
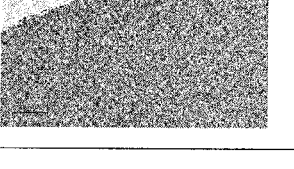

Treatment and Monitoring:

Compounds of the disclosure were prepared in PBS, filter sterilized and administered daily via IP injection. The mice in control group received PBS. The treatment started when mice reached score 2 or 2.5 (13-16 days post immunization) and continued until day 60. The weight and scores were recorded periodically. The scores were assigned according to the guidelines provided in SOP R-04 (UHN ARC). After the experiment was concluded, tissue (brain, spinal cord and liver) were removed for further analysis. FIG. 6 is a graph showing the effect of two compounds of the disclosure in an in vivo mouse model, EAE to study the efficacy of PAD inhibitors. FIG. 7 shows the levels of PAD2 and citrullination in mouse cerebral cortex, corresponding to the study in FIG. 6. Images show the coronal cross section of the cerebral cortex stained with PAD2 antibody and citrulline antibody. The tissue was collected from healthy and EAE affected mice. The EAE mice were treated with either PBS, KP-302 or KP-305. The secondary antibody is colored brown. The blue color spots is background staining. The same area of the brain in each specimen stained with PAD2 or citrulline is shown.

Example 56: Studies on the MOG-EAE Mouse Model (FIGS. 8-12)

Figure 8:
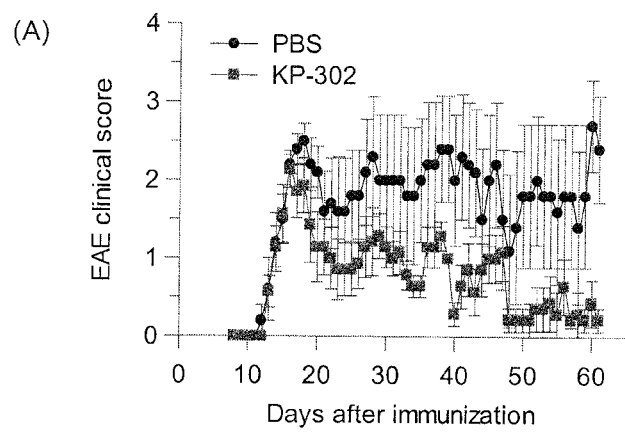
FIG. 8 shows (A) The progression of EAE in C57BL/6 female mice treated with PBS (n=5) or a compound of the disclosure (n=7). (B) Normalized weight of EAE mice treated with either PBS or a compound of the disclosure. (C) Survival graph showing the mortality rates in PBS and treated mice.
Figure 8:
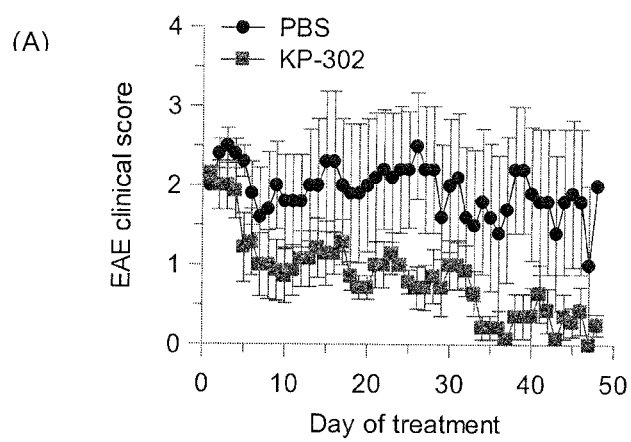
Figure 8:
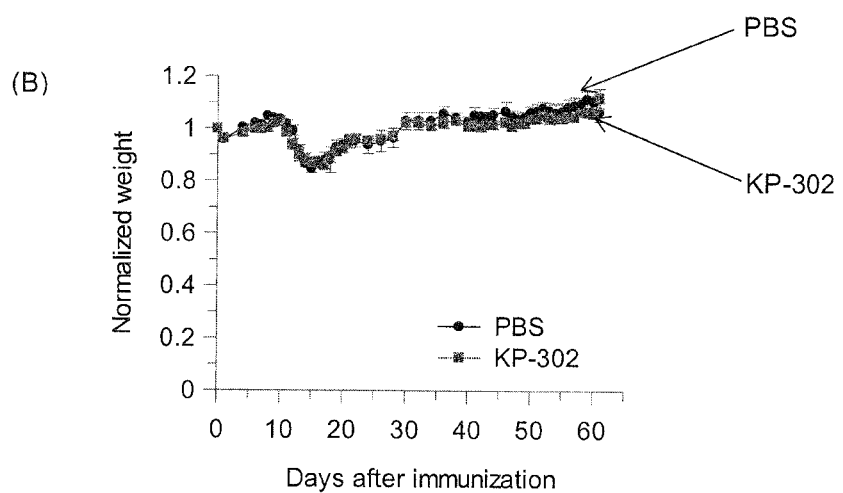
Figure 8:
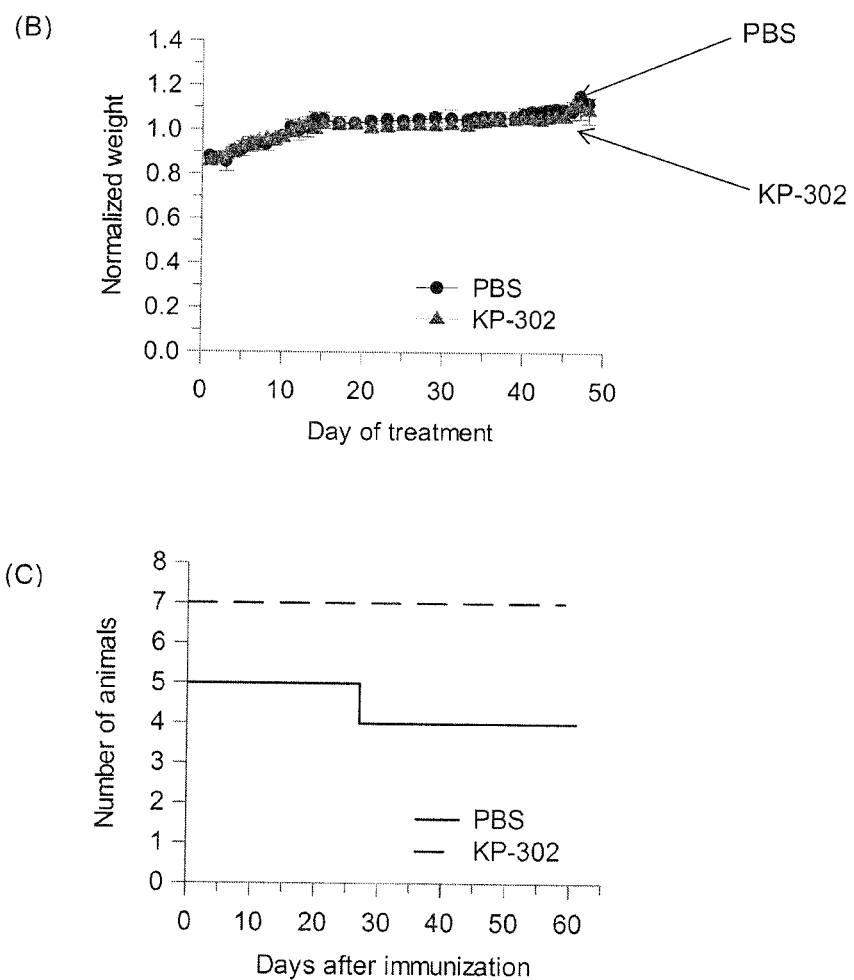

A study with compound 18 (labelled KP-302) was carried in EAE animal models (FIG. 8). C57BL/6 female mice (n=7) EAE induced with myelin oligodendrocyte glycoprotein (MOG) peptide were injected with a 10 mg/mL (dose 1 mg per mouse) solution of KP-302 after 12 days of immunization. Their EAE scores were measured and compared against the control group (PBS, n=5) to analyze the effects of KP-302 on motor function regeneration. There is a significant decrease in EAE scores in the treatment group in comparison to PBS over the course of treatment, suggesting that KP-302 has potential in re-establishing motor functions in diseased models.

Animal studies were performed according a protocol reviewed and approved by Animal Care Committee at Toronto General Hospital, University Health Network. The storage, handling and use of Pertussis toxin was approved by the UHN Biosafety Committee and by the Public Health Agency of Canada. The MOG peptide was purchased from Stanford Pan Facility. The Pertussis toxin was obtained from LIST Biologicals as a salt-free lyophilized powder. Incomplete Freund's adjuvant (IFA) (DIFCO, Cat 263910) and *Mycobacterium tuberculosis* H37RA (DIFCO, 231141) were purchased from BD Biosciences, Canada.

Seven weeks old female mice (C57BL/6) were purchased from Jackson Laboratories (NY, USA). Animals were housed in the Animal Resource Center facility (UHN, Toronto) and maintained under regulated light and temperature conditions. The food and water were available ad libitum. Experimental autoimmune encephalomyelitis (EAE) was induced in 8 weeks old mice by immunization with myelin oligodendrocyte glycoprotein ($MOG_{33-55}$) peptide emulsified in complete Freund's adjuvant (100 µg of MOG per mouse via subcutaneous injection) followed by the intraperitoneal administration of Pertussis toxin (PTX) (400 ng per mouse). PTX injection was repeated 48 hours after the initial immunization. Mice were monitored daily for the symptoms of EAE. The symptoms started to develop 8-14 days after the immunization. Mice were weighted and EAE scores were assigned every day. The treatment was initiated once the animals reached score 2 (limp tail and mild paresis of at least one hind limb).

KP-302 was prepared in 1× sterile PBS pH 7.4, filter sterilized and administered daily via intraperitoneal injection. The dose of KP-302 was 1 mg per mouse. Control mice received the same volume of PBS. The collected organs were processed and stained at TCP (Toronto Center for Phenogenomics, Toronto, ON). The brain and spinal cord tissues were stained with Luxol Fast Blue (LFB) and Hematoxylin and Eosin (H&E). The brain tissue was also stained with antibody against PAD2, PAD4, citrulline, and T-cells (CD3+ve).

The slides were digitalized using brightfield scanner ScanScope XT (Aperio Technologies) at 20× maximum magnification. The images were viewed and analyzed with the free image viewer ImageScope (Aperio Technologies). The quantitative analyses of the brain lesions were performed using Positive Pixel Count Algorithm included in the ImageScope program. Visual inspection of the slides allowed evaluation of the type of lesions affecting the CNS tissue. The extent of inflammation was determined by calculating the ratio of the area affected to the total area of the tissue cross section per specimen. The Positive Pixel Count algorithm was used to quantify the amount of a specific stain present in the scanned image. The color parameters (hue and saturation) were specified for the analysis of CD3+ve stained tissue. The intensity ranges were left at default values.

First, the inflamed areas were manually selected and the number of positive pixels corresponding to the appropriate stain was obtained using the Positive Pixel Count algorithm. The total area of the tissue was carefully selected excluding hollow spaces (ventricular systems) and the area was calculated. The number of stained cells per unit of area (μm2) was calculated based on the pixel area, the average area of the stained cells (picked at random, measured and averaged).

Figure 9:
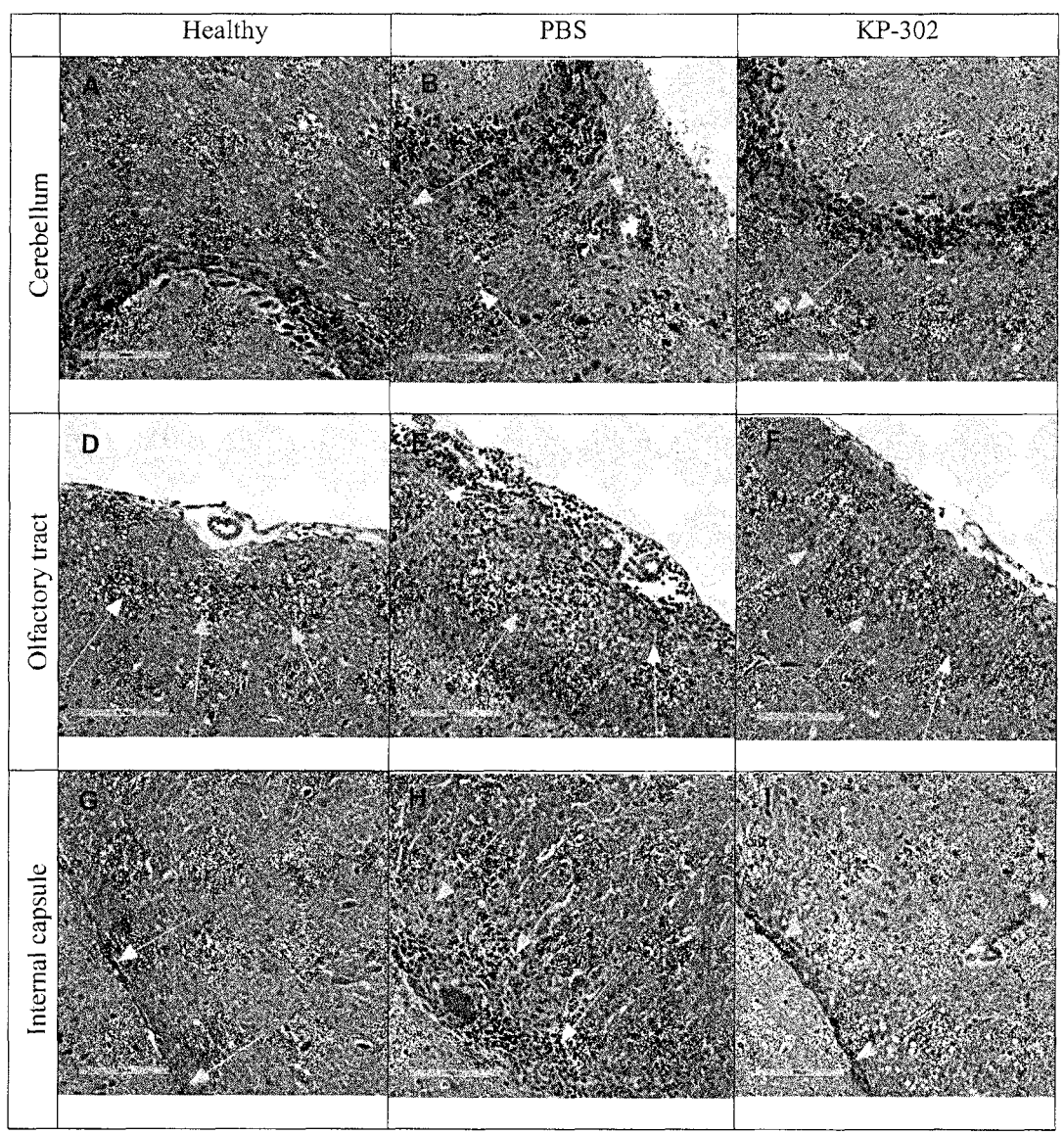
FIG. 9 are micrographs showing Cerebellum of healthy (A) and EAE affected mice (B and C). EAE control animals received PBS and drug treated animals were injected (i.p.) a compound of the disclosure.

FIG. 9 are micrographs showing Cerebellum of healthy (A) and EAE affected mice (B and C). EAE control animals received PBS and drug treated animals were injected (i.p.) with 1 mg per mouse of KP-302 daily. Arrows point to lesions (perivascular cuffs) formed in the cerebellum of sick mice. The PBS receiving mice had higher number of more pronounced lesions as compared to KP-302 treated mice. Lateral olfactory tract area (Figure D-F) was often observed to be affected by lesions. (E) Shown is a lesion and lymphocytic leptomeningitis in PBS treated mouse. The corresponding areas (indicated by arrows) in healthy and KP-302 treated mouse are clear. Perivascular leukoencepahlitis, lymphocytic and neutrophilic inflammation along the internal capsule. (G) healthy control, (H) PBS control, (I) KP-302 treated. Magnification 20×. Scale bar indicates 100 μm. Magnification 20× (ImageScope viewer).

Figure 10:
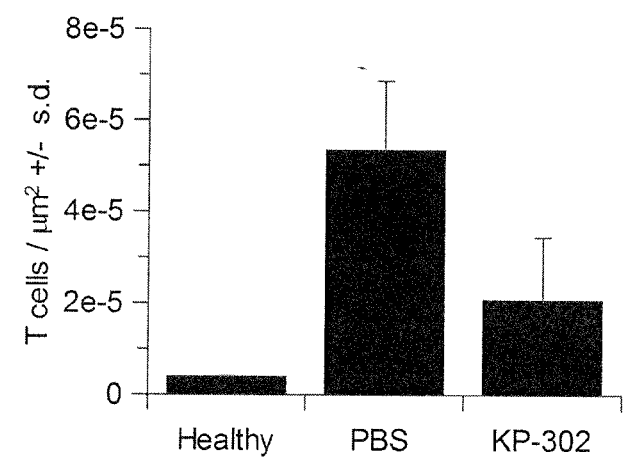
FIG. 10 are bar graphs showing Immunohistochemistry of EAE affected mice brains. The tissue was probed with CD3+ve antibody to detect T lymphocytes in the CNS of healthy and sick mice. The sick animals were treated with PBS or a compound of the disclosure.
Figure 10:
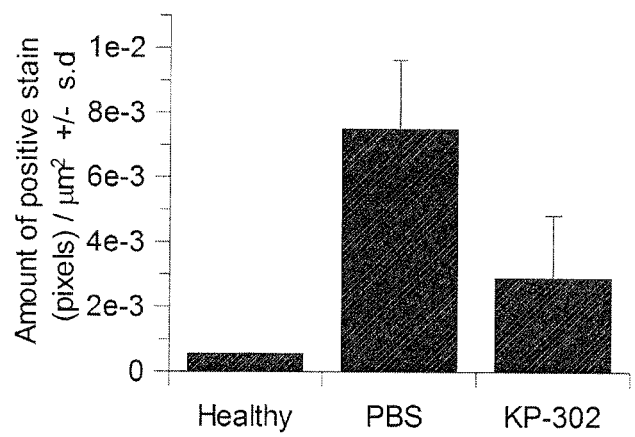

FIG. 10 shows Immunohistochemistry of EAE affected mice brains. The tissue was probed with CD3+ve antibody to detect T lymphocytes in the CNS of healthy and sick mice. The sick animals were treated with PBS or KP-302.

Figure 11:
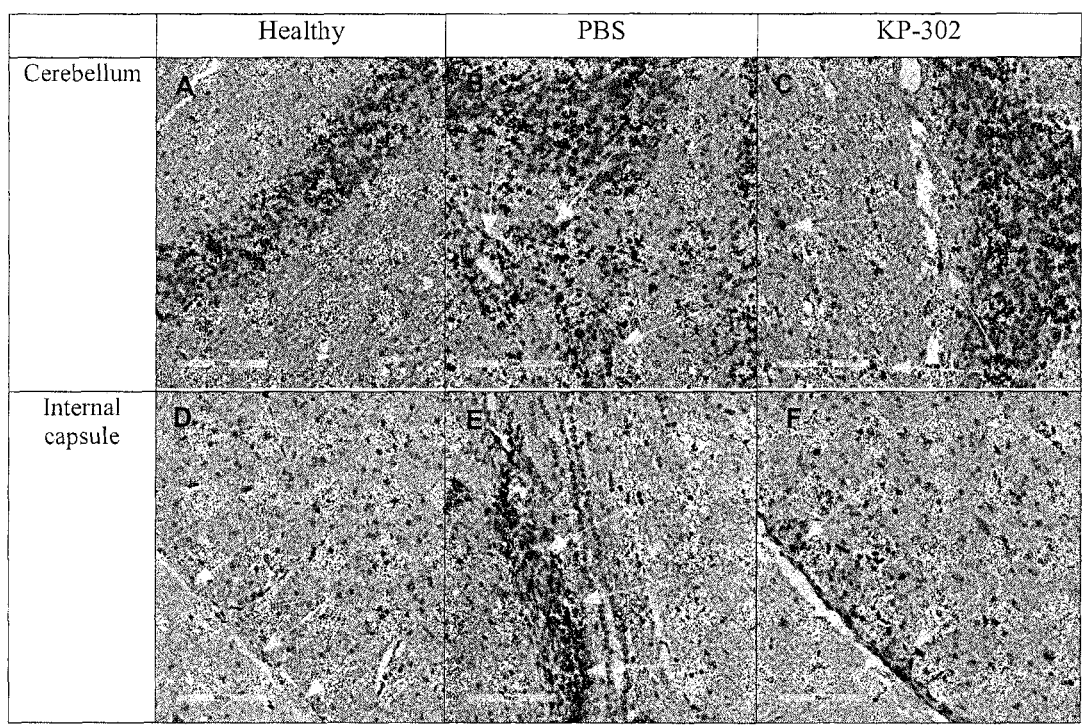
FIG. 11 are micrographs showing CD3+ve staining for T-cells lymphocytes showing inflammation in cerebellum (A-C) and along the internal capsule (D-F).

FIG. 11 shows CD3+ve staining for T-cells lymphocytes. Shown is the inflammation in cerebellum (A-C) and along the internal capsule (D-F). The inflammation as indicated by the number of infiltrating T cells was in general more severe in the PBS receiving mice. The tissue collected from KP-302 treated mice shown milder lesions and scattered T cells not clearly associated with any specific lesion. Magnification 20× (ImageScope viewer)

Figure 12:
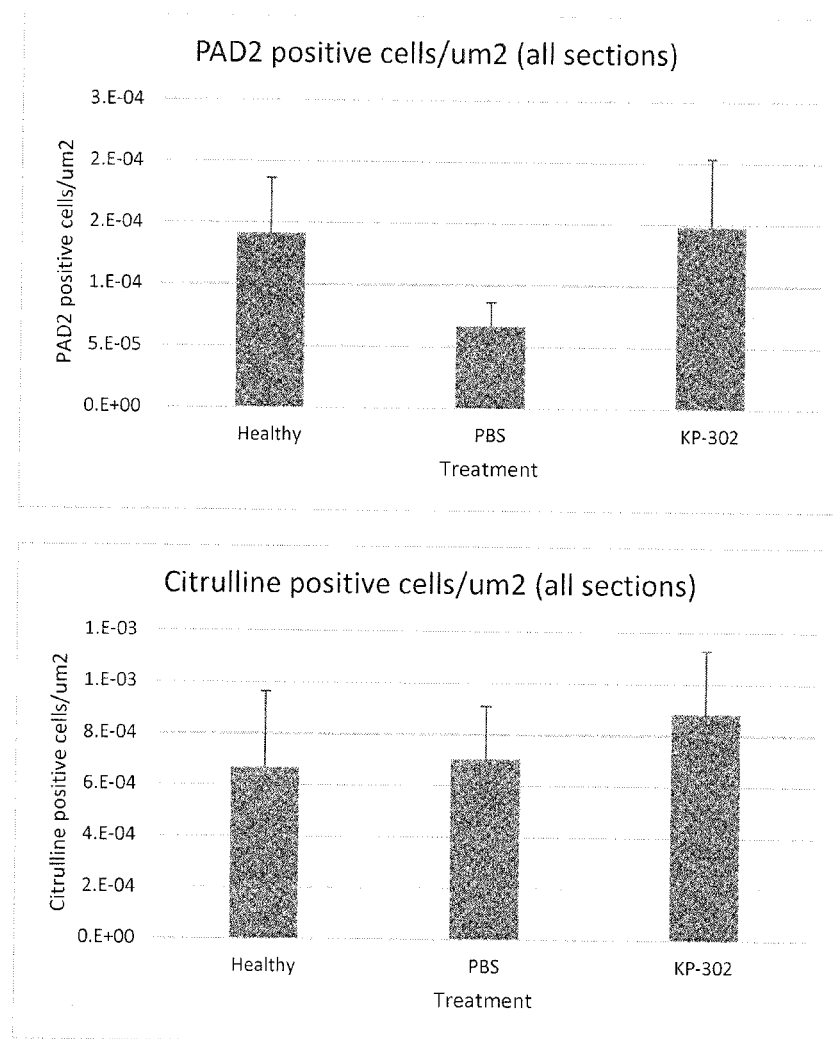
FIG. 12 shows PAD2 positive cells and citrulline positive cells as quantified for healthy, EAE control (PBS), and EAE treated mice brain tissue.

FIG. 12 shows PAD2 positive cells and citrulline positive cells as quantified for healthy, EAE control (PBS), and EAE treated (KP-302) mice brain tissue.

While the present application has been described with reference to what are presently considered to be the preferred examples, it is to be understood that the scope of the claims should not be limited by the preferred embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

PAD1, PAD2, and PAD4 inhibition constant $K_i$ for KP-224, and KP-226 (compound 31) determined.

| | $K_i$ ± Std Error (μM) | | |
|---|---|---|---|
| Code | PAD1 | PAD2 | PAD4 |
| KP-224 | 64.0 ± 4.2 | 21.3 ± 3.4 | 35.2 ± 7.0 |
| KP-226 | 64.6 ± 7.6 | 19.7 ± 2.0 | 27.6 ± 8.1 |

TABLE 2

Remaining activity of PAD2 in the presence of PAD inhibitors.

| | Remaining Activity (%) | |
|---|---|---|
| | [I] = 100 μM | [I] = 1 mM |
| KP-225 (compound 37) | 86.6 ± 3.0 | 70.8 ± 1.7 |
| KP-227 (compound 39) | 63.7 ± 0.6 | 68.2 ± 2.3 |
| KP-228 (compound 33) | 58.6 ± 3.6 | 31.8 ± 4.9 |
| KP-229 | 54.0 ± 2.7 | 63.3 ± 2.0 |
| KP-230 | 55.1 ± 0.5 | 33.5 ± 0.4 |
| KP-231 | 44.4 ± 0.5 | 45.5 ± 1.1 |

TABLE 3

Remaining activity of PAD4 in the presence of PAD inhibitors.

| | Remaining Activity (%) | |
|---|---|---|
| | [I] = 100 μM | [I] = 1 mM |
| KP-224 | 97.2 ± 0.8 | 76.0 ± 1.2 |
| KP-226 (compound 31) | 66.3 ± 4.7 | 100.0 ± 3.6 |

TABLE 4

Remaining activity of PAD4 in the presence of PAD inhibitors.

| | Remaining Activity (%) | |
|---|---|---|
| | [I] = 100 μM | [I] = 1 mM |
| KP-225 (compound 37) | 78.7 ± 9.5 | 62.2 ± 2.7 |
| KP-227 (compound 39) | 100.0 ± 1.3 | 82.2 ± 2.4 |
| KP-228 (compound 33) | 96.4 ± 10.4 | 82.1 ± 7.2 |
| KP-229 | 100.0 ± 5.5 | 100.0 ± 2.6 |
| KP-230 | 96.9 ± 7.6 | 82.4 ± 1.7 |
| KP-231 | 100.4 ± 4.6 | 82.3 ± 3.7 |

TABLE 5

Activity for PAD1, PAD2, PAD4

| Structure | KP code | PAD1 $K_i$ ± std error (μM) | PAD2 $K_i$ ± std error (μM) | PAD4 $K_i$ ± std error (μM) |
|---|---|---|---|---|
| 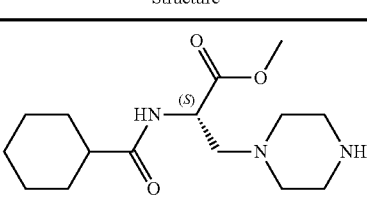 | KP-224 | | | No inhibition up to 10 mM |

TABLE 5-continued

Activity for PAD1, PAD2, PAD4

| Structure | KP code | PAD1 $K_i \pm$ std error ($\mu$M) | PAD2 $K_i \pm$ std error ($\mu$M) | PAD4 $K_i \pm$ std error ($\mu$M) |
| --- | --- | --- | --- | --- |
| 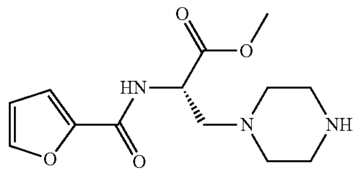 [SMILES: COC(=O)[C@H](CN1CCNCC1)NC(=O)c1ccco1] | KP-225 | | | |
| 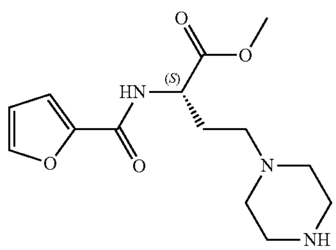 | KP-226 | | $286 \pm 27$ | |
| 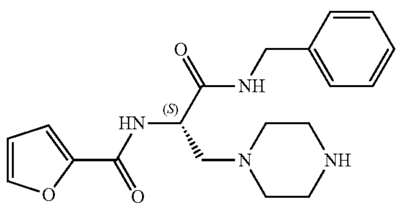 | KP-227 | | | |
| 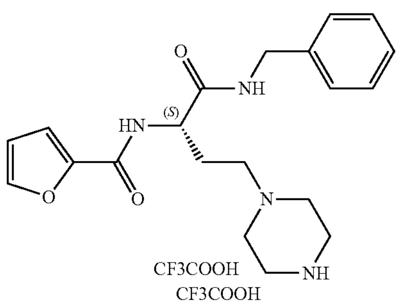 | KP-228 | | | |
| 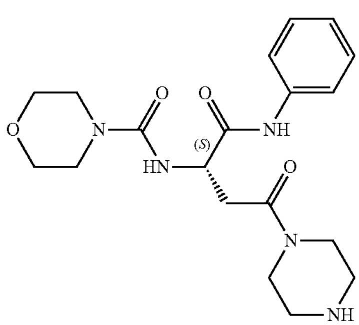 | KP-229 | | | |

TABLE 5-continued

Activity for PAD1, PAD2, PAD4

| Structure | KP code | PAD1 $K_i$ ± std error (µM) | PAD2 $K_i$ ± std error (µM) | PAD4 $K_i$ ± std error (µM) |
|---|---|---|---|---|
| 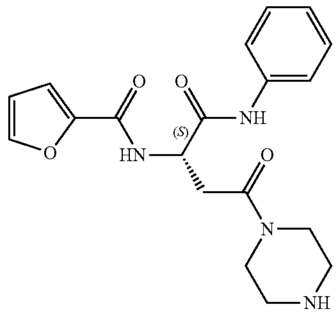 | KP-230 | | | |
| 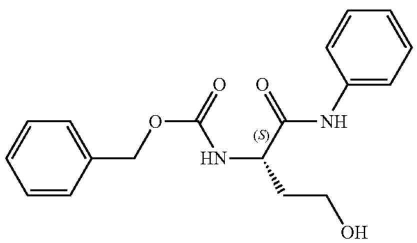 | KP-231 | | | |
| 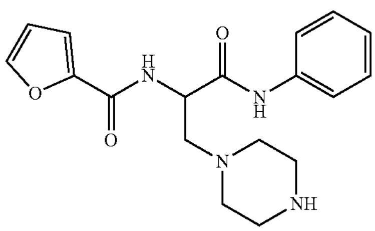 [SMILES: O=C(NC(CN1CCNCC1)C(=O)Nc1ccccc1)c1ccco1] | KP-257 | | | |
| 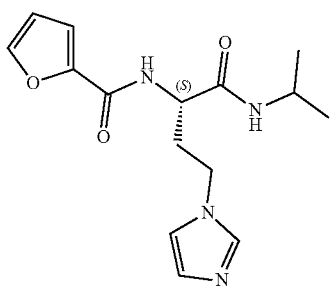 | KP-286 | 2495 ± 1785 | 554 ± 93 | 714 ± 100 |
| 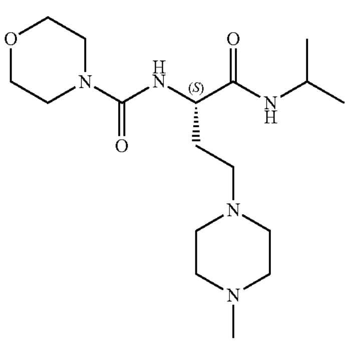 | KP-287 | Some inhibition but IC50 not calculated - no Ki | 600 ± 1332 | No inhibition up to 10 mM |

TABLE 5-continued

Activity for PAD1, PAD2, PAD4

| Structure | KP code | PAD1 $K_i$ ± std error (μM) | PAD2 $K_i$ ± std error (μM) | PAD4 $K_i$ ± std error (μM) |
|---|---|---|---|---|
| 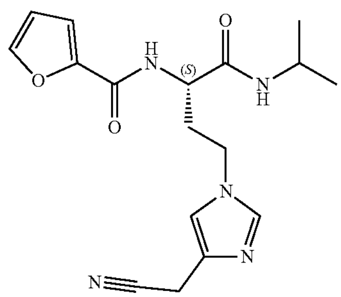 | KP-288 | 914 ± 59 | 176 ± 62 | 591 ± 77 |
| 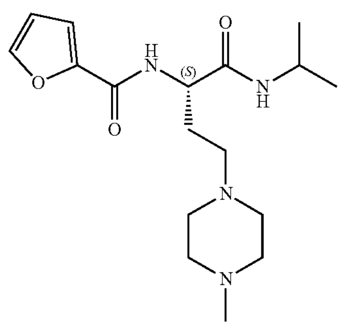 | KP-289 | | 1786 ± 2420 | 488 ± 47 |
| 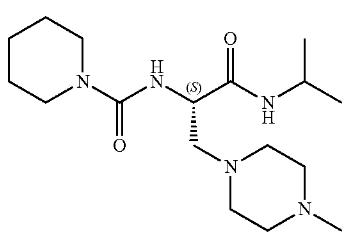 | KP-290 | | | No inhibition up to 10 mM |
| 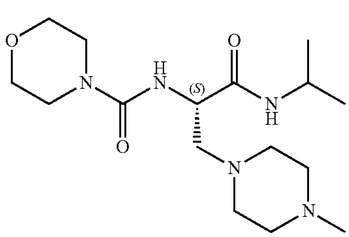 | KP-291 | No inhibition up to 10 mM | No inhibition up to 10 mM | No inhibition up to 10 mM |
| 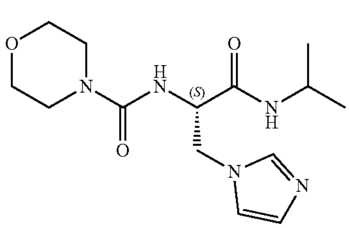 | KP-292 | | | ~14940 |

TABLE 5-continued

Activity for PAD1, PAD2, PAD4

| Structure | KP code | PAD1 $K_i \pm$ std error ($\mu$M) | PAD2 $K_i \pm$ std error ($\mu$M) | PAD4 $K_i \pm$ std error ($\mu$M) |
|---|---|---|---|---|
| 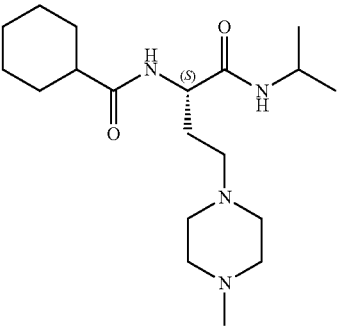 | KP-295 | | No inhibition up to 10 mM | No inhibition up to 10 mM |
| 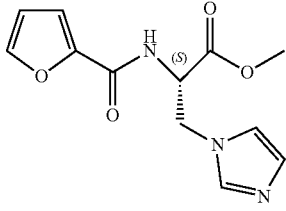 | KP-298 | 785 ± 384 | 662 ± 210 | 1238 ± 1393 |
| 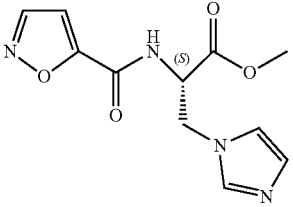 | KP-299 | Not soluble - not tested | Not soluble - not tested | Not soluble - not tested |
| 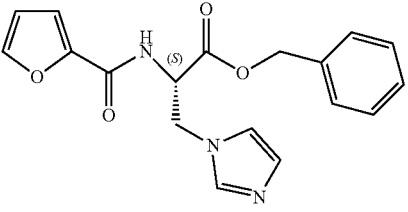 | KP-300 | No inhibition up to 10 mM | 739 ± 339 | 1068 ± 427 |
| 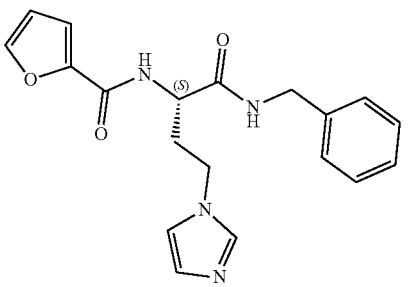 | KP-301 | No inhibition up to 10 mM | No inhibition up to 10 mM | No inhibition up to 10 mM |

TABLE 5-continued

Activity for PAD1, PAD2, PAD4

| Structure | KP code | PAD1 $K_i$ ± std error ($\mu$M) | PAD2 $K_i$ ± std error ($\mu$M) | PAD4 $K_i$ ± std error ($\mu$M) |
|---|---|---|---|---|
| 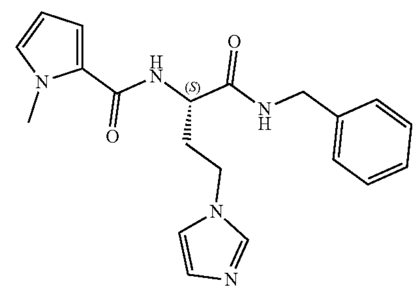 | KP-302 | 402 ± 98 | 60 ± 12 | 180 ± 12 |
| 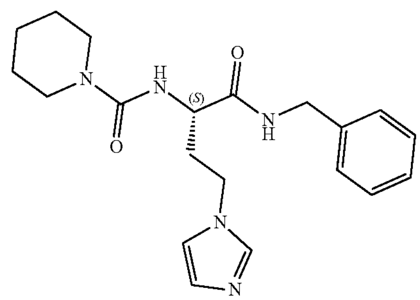 | KP-303 | 392 ± 72 | 1387 ± 270 | 220 ± 35 |
| 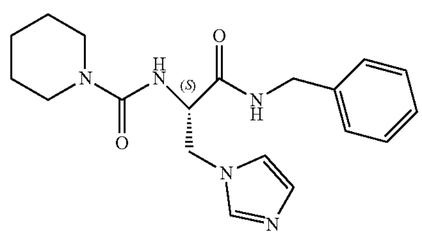 | KP-304 | | 5300 ± 7830 | No inhibition up to 10 mM |
| 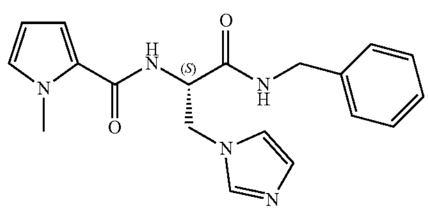 | KP-305 | 147 ± 52 | 58 ± 5 | 75 ± 9 |
| 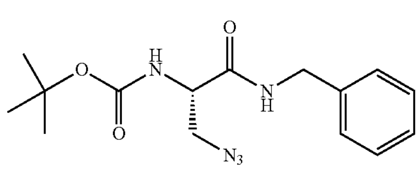 [SMILES: CC(C)(C)OC(=O)N[C@@H](CN=[N+]=[N-])C(=O)NCc1ccccc1] | KP-306 | No inhibition up to 10 mM | No inhibition up to 10 mM | No inhibition up to 10 mM |
| 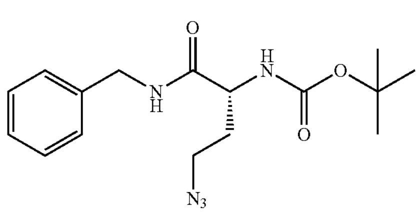 [SMILES: CC(C)(C)OC(=O)N[C@H](CCN=[N+]=[N-])C(=O)NCc1ccccc1] | KP-310 | 3430 ± 1941 | 1429 ± 186 | 1453 ± 187 |

TABLE 5-continued

Activity for PAD1, PAD2, PAD4

| Structure | KP code | PAD1 $K_i \pm$ std error ($\mu$M) | PAD2 $K_i \pm$ std error ($\mu$M) | PAD4 $K_i \pm$ std error ($\mu$M) |
| --- | --- | --- | --- | --- |
| 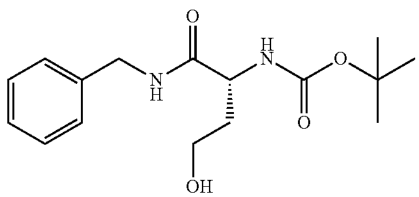 [SMILES: CC(C)(C)OC(=O)N[C@H](CCO)C(=O)NCc1ccccc1] | KP-311 | No inhibition up to 10 mM | No inhibition up to 10 mM | No inhibition up to 10 mM |
| 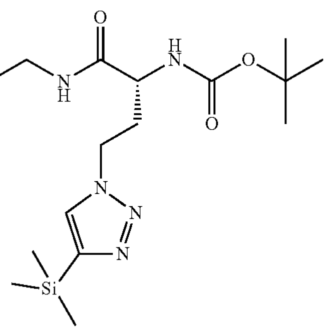 | KP-312 | | | |
| 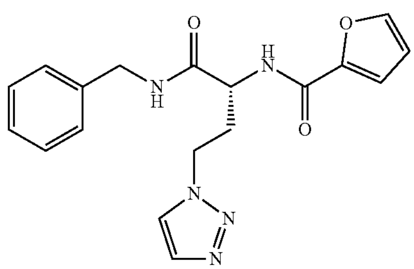 [SMILES: O=C(N[C@H](CCn1ccnn1)C(=O)NCc1ccccc1)c1ccco1] | KP-313 | 1086 ± 499 | 282 ± 86 | 2823 ± 1804 |
| 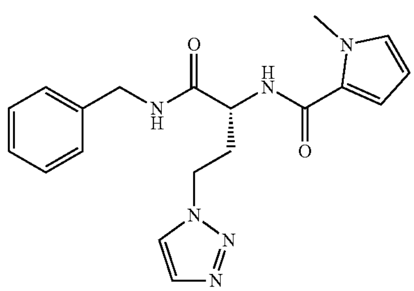 [SMILES: Cn1cccc1C(=O)N[C@H](CCn1ccnn1)C(=O)NCc1ccccc1] | KP-314 | 112 ± 17 | 71 ± 18 | 65 ± 28 |
| 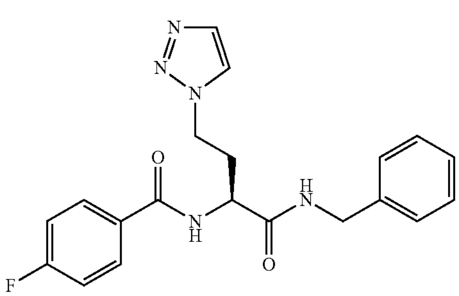 [SMILES: O=C(N[C@@H](CCn1ccnn1)C(=O)NCc1ccccc1)c1ccc(F)cc1] | KP-316 | 77690 ± 91480 | Some inhibition but IC50 can't be calculated - no Ki | Some inhibition but IC50 can't be calculated - no Ki |

TABLE 6

Enzyme inhibition kinetics for non-covalent compounds hPAD1, mPAD2, and hPAD4 and IC$_{50}$ CHO cell toxicity assays for synthesized non-covalent inhibitors.

| # | K$_i$ (μM) hPAD1 | mPAD2 | hPAD4 | IC$_{50}$ CHO Cells (μM) | Predicted side chain pKa | Predicted logP |
|---|---|---|---|---|---|---|
| KP-289 | N/A | 1838 ± 2421 | 488 ± 47 | >2000 | 6.1, 5.8 | −.69 |
| KP-287 | >10,000 | >10,000 | >10,000 | >2000 | 6.1, 5.8 | −1.45 |
| KP-295 | N/A | >10,000 | >10,000 | N/A | 6.1, 5.8 | 0.78 |
| KP-286 | 964 ± 689 | 554 ± 93 | 88 ± 29 | 546 ± 136 | 7.2 | −1.11 |
| KP-301 | >10,000 | >10,000 | >10,000 | N/A | 7.2 | −0.04 |
| KP-303 | 151 ± 27 | 1388 ± 269 | 220 ± 35 | >2000 | 7.2 | 0.32 |
| KP-302 | 155 ± 38 | 60 ± 12 | 180 ± 12 | >2000 | 7.2 | 0.13 |
| KP-288 | 353 ± 23 | 1001 ± 876 | 591 ± 77 | >2000 | 8.6 | −0.71 |
| KP-314 | 112 ± 17 | 71 ± 18 | 64 ± 28 | N/A | 13.3 | 0.53 |
| KP-313 | 1,086 ± 499 | 282 ± 86 | 2,823 ± 1,804 | N/A | 13.3 | 0.37 |
| KP-316 | >10,000 | N/A | N/A | N/A | 13.3 | 1.91 |

TABLE 7

SAR table for novel non-covalent inhibitors towards PAD enzymes.

| # | R$_1$ | R$_2$ | R$_3$ | hPAD1 | mPAD2 | hPAD4 |
|---|---|---|---|---|---|---|
| KP-289 | 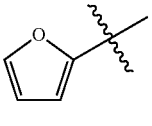 | 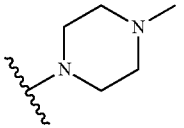 [SMILES: *N1CCN(C)CC1] | 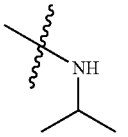 [SMILES: *NC(C)C] | N/A | 0.3 (PAD4) | 3.7 (PAD2) |
| KP-286 | 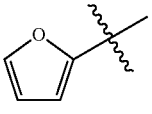 [SMILES: *c1ccco1] | 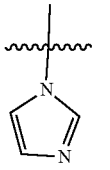 [SMILES: *n1ccnc1] | 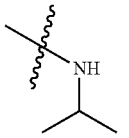 [SMILES: *NC(C)C] | 0.6 (PAD2)<br>0.1 (PAD4) | 1.7 (PAD2)<br>0.2 (PAD4) | 11 (PAD1)<br>6.3 (PAD2) |
| KP-288 | 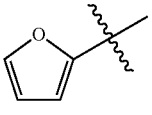 [SMILES: *c1ccco1] | 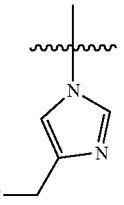 | 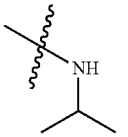 [SMILES: *NC(C)C] | 2.8 (PAD2)<br>1.6 (PAD4) | 0.4 (PAD1)<br>0.6 (PAD4) | 0.6 (PAD1)<br>1.7 (PAD2) |
| KP-301 | 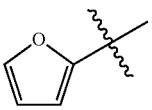 [SMILES: *c1ccco1] | 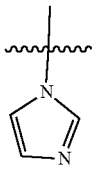 [SMILES: *n1ccnc1] | 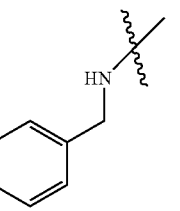 | N/A | N/A | N/A |

TABLE 7-continued

SAR table for novel non-covalent inhibitors towards PAD enzymes.

| # | R₁ | R₂ | R₃ | hPAD1 | mPAD2 | hPAD4 |
|---|----|----|----|-------|-------|-------|
| KP-313 | furan | triazole | benzylamine (HN-CH₂-Ph) | 0.3 (PAD2) 2.6 (PAD4) | 3.9 (PAD1) 10 (PAD4) | 0.4 (PAD1) 0.1 (PAD2) |
| KP-302 | N-methylpyrrole | imidazole | benzylamine | 0.4 (PAD2) 1.2 (PAD4) | 2.6 (PAD1) 3 (PAD4) | 0.9 (PAD1) 0.3 (PAD2) |
| KP-314 | N-methylpyrrole | triazole | benzylamine | 0.6 (PAD2) 0.6 (PAD4) | 1.6 (PAD1) 1.1 (PAD4) | 1.8 (PAD1) 1.1 (PAD2) |
| KP-287 | morpholine | N-methylpiperazine | isopropylamine | N/A | N/A | N/A |
| KP-295 | cyclohexyl | N-methylpiperazine | isopropylamine | N/A | N/A | N/A |
| KP-303 | piperidine | imidazole | benzylamine | 9.2 (PAD2) 1.5 (PAD4) | 0.1 (PAD1) 0.2 (PAD4) | 0.7 (PAD1) 6.3 (PAD2) |
| KP-316 | 4-fluorophenyl | triazole | benzylamine | N/A | N/A | N/A |

The following publications are hereby incorporated by reference:
1. Popescu, B. F.; Lucchinetti, C. F. Pathology of demyelinating diseases. *Annu. Rev. Pathol.* 2012, 7, 185-217.
2. Dutta, R.; Trapp, B. D. Pathogenesis of axonal and neuronal damage in multiple sclerosis. *Neurology* 2007, 68(2), S22-S31.
3. Noseworthy, J. H. Progress in determining the causes and treatment of multiple sclerosis. *Nature* 1999, 399, A40-A47.
4. Aluord, E. C. Acute disseminated encephalomyelitis and allergic encephalopathies. In Vinken P. I., Bruyan G. W. Handbook of clinical neurology, New York, N. Y., Elsevier. 1970, 9, 560-571.
5. Hashim, G. A.; Wood, D. D.; Moscarello, M. A. Myelin lipophilin induced demyelinating diseases of the central nervous system. *Neurochem. Res.* 1980, 5, 1117-1115.
6. Sospedra, M.; Martin, R. Immunology of multiple sclerosis. *Annu. Rev. Immunol.* 2005, 23, 683-747.
7. Lebar, R.; Lubetzki, C.; Vincent, C.; Lombrail, P.; Boutry, J. M. The M2 autoantigen of central nervous system myelin, a glycoprotein present in oligodendrocyte membrane. *Clin. Exp. Immunol.* 1986, 66(2), 423-434.
8. Bahreini, S. A.; Jabalameli, M. R.; Saadatnia, M.; Zahednasab, H. The role of non-HLA single nucleotide polymorphisms in multiple sclerosis susceptibility. *J Neuroimmunol.* 2010, 229, 5-15.
9. Steinman, L.; Zamvil, S. S. Multiple sclerosis in need of a critical reappraisal. *Med. Hypothesis.* 2006, 54, 99-106.
10. Lopez-Diego, R. S.; Weiner, H. L. Novel therapeutic strategies for multiple sclerosis—a multifaceted adversary. *Nature Rev. Drug Discov.* 2008, 7, 909-925.
11. Weinstock-Guttman, B.; Jacobs, L. D. What is new in the treatment of multiple sclerosis. *Drugs* 2000, 59, 401-410.
12. Quirke, A. M.; Fisher, B. A.; Kinloch, A. J.; Venables, P. J. Citrullination of autoantigens: upstream of TNFα in the pathogenesis of rheumatoid arthritis. *FEBS Lett.* 2011, 585(23), 3681-3688.
13. Lange, S.; Gogel, S.; Leung, K. Y.; Vemay, B.; Nicholas, A. P.; Causey, C. P.; Thompson, P. R.; Greene, N. D.; Ferretti, P. Protein deiminases: new players in the developmentally regulated loss of neural regenerative ability. *Dev. Biol.* 2011, 355(2), 205-214.
14. Kidd, B. A.; Ho, P. P.; Sharpe, O.; Zhao, X.; Tomooka, B. H.; Kanter, J. L.; Steinman, L.; Robinson, W. H. Epitope spreading to citrullinated antigens in mouse models of autoimmune arthritis and demyelination. *Arthritis Res. Ther.* 2008, 10, R119.
15. Harauz, G.; Musse, A. A. A tale of two citrullines—structural and functional aspects of myelin basic protein deimination in health and disease. *Neurochem. Res.* 2007, 32, 137-158.
16. Moscarello, M. A.; Wood, D. D.; Ackerley, C.; Boulias, C. Myelin in multiple sclerosis is developmentally immature. *J Clin. Invest.* 1994, 94, 146-154.
17. Wood, D. D.; Bilbao, J. M.; O'Connors, P.; Moscarello, M. A. Acute multiple sclerosis (Marburg type) is associated with developmentally immature myelin basic protein. *Ann. Neurol.* 1996, 40, 18-24.
18. Brady, G. W.; Fein, D. B.; Wood, D. D.; Moscarello, M. A. The interaction of basic proteins from normal and multiple sclerosis myelin with phosphatidylglycerol vesicles. *FEBS Lett.* 1981, 125, 159-160.
19. Brady, G. W.; Murthy, N. S.; Fein, D. B.; Wood, D. D.; Moscarello, M. A. The effect of basic myelin protein on multilayer membrane formation. *Biophys. J.* 1981, 34(2), 345-350.
20. Boggs, J. M.; Wood, D. D.; Moscarello, M. A. Hydrophobic and electrostatic interactions of myelin basic proteins with lipid. Participation of N-terminal and C-terminal portions. *Biochemistry* 1981, 20(5), 1065-1073.
21. Epand, R. M.; Moscarello, M. A.; Zierenberg, B.; Vail, W. J. The folded conformation of the encephalitogenic protein of the human brain. *Biochemistry* 1974, 13, 1264-1267.
22. Deber, C. M.; Hughes, D. W.; Fraser, P. E.; Pawagi, A. B.; Moscarello, M. A. Binding of human normal and multiple sclerosis-derived myelin basic protein to phospholipid vesicles: effects on membrane head group and bilayer regions. *Arch. Biochem. Biophys.* 1986, 245(2), 455-463.
23. Carrillo-Vico, A.; Leech, M. D.; Anderton, S. M. Contribution of myelin autoantigen citrullination to T cell autoaggression in the central nervous system. *J. Immunol.* 2010, 184 (6), 2839-2846.
24. Raijmakers, R.; Vogelzangs, J.; Croxford, J. L.; Wesseling, P.; van Venrooij, W. J.; Pruijn, G. J. Citrullination of central nervous system proteins during the development of experimental autoimmune encephalomyelitis. *J. Comp. Neurol.* 2005, 486(3), 243-253.
25. Gyorgy, B.; Toth, E.; Tarcsa, E.; Falus, A.; Buzas, E. I. Citrullination: a posttranslational modification in health and disease. *Int. J. Biochem. Cell. Biol.* 2006, 38 (10), 1662-1677.
26. Curis, E.; Nicolis, I.; Moinard, C.; Osowska, S.; Zerrouk, N.; Benazeth, S.; Cynober, L. Almost all about citrulline in mammals. *Amino Acids* 2005, 29 (3), 177-205.
27. Vossenaar, E. R.; Zendman, A. J.; van Venrooij, W. J.; Pruijn, G. J. PAD, a growing family of citrullinating enzymes: genes, features and involvement in disease. *Bioessays* 2003, 25(11), 1106-1118.
28. Anzilotti, C.; Pratesi, F.; Tommasi, C.; Migliorini, P. Peptidylarginine deiminase 4 and citrullination in health and disease. *Autoimmun Rev.* 2010, 9(3), 158-160.
29. Anzilotti, C.; Pratesi, F.; Tommasi, C.; Migliorini, P. Peptidylarginine deiminase 4 and citrullination in health and disease. *Autoimmun Rev.* 2010, 9(3), 158-160.
30. Chirivi, R. G. S.; van Rosmale, J. W. G.; Jenniskens, G. J.; Pruijn, G. J.; Raats, J. M.-H. itrullination: A trget for disease intervention in multiple sclerosis and other inflammatory disorders. *J Clin. Cell. Immunol.* 2-13, 4, 3.
31. Carrillo-Vico, A.; Leech, M. D.; Anderton, S. M. Contribution of myelin autoantigen citrullination to T cell autoaggression in the central nervous system. *J Immunol.* 2010, 184(6), 2839-2846.
32. Musse, A. A.; Harauz, G. Molecular "negativity" may underlie multiple sclerosis:
role of the myelin basic protein family in the pathogenesis of MS. *Int. Rev. Neurobiol.* 2007, 79, 149-172.
33. Deraos, G.; Chatzantoni, K.; Matsoukas, M. T.; Tselios, T.; Deraos, S.; Katsara, M.; Papathanasopoulos, P.; Vynios, D.; Apostolopoulos, V.; Mouzaki, A.; Matsoukas, J. Citrullination of linear and cyclic altered peptide ligands from myelin basic protein (MBP(87-99)) epitope elicits a Th1 polarized response by T cells isolated from multiple sclerosis patients: implications in triggering disease. *J. Med. Chem.* 2008, 51(24), 7834-7842.
34. Moscarello, M. A.; Lei, H.; Mastronardi, F. G.; Winer, S.; Tsui, H.; Li, Z.; Ackerley, C.; Zhang, L.; Raijmakers, R.; Wood, D. D. Inhibition of peptidyl-arginine deiminases reverses protein-hypercitrullination and disease in mouse models of multiple sclerosis. *Dis. Model. Mech.* 2013, 6(2), 467-478.

35. Moscarello, M. A.; Lei, H.; Mastronardi, F. G.; Winer, S.; Tsui, H.; Li, Z.; Ackerley, C.; Zhang, L.; Raijmakers, R.; Wood, D. D. Inhibition of peptidyl-arginine deiminases reverses protein-hypercitrullination and disease in mouse models of multiple sclerosis. *Dis. Model. Mech.* 2013, 6(2), 467-478.

36. Suzuki, A.; Yamada, R.; Yamamoto, K. Citrullination by Peptidylarginine Deiminase in Rheumatoid Arthritis. *Ann. N.Y. Acad. Sci.* 2007, 1108, 323-339.

37. Arita, K.; Hashimoto, H.; Shimizu, T.; Nakashima, K.; Yamada, M.; Sato, M. Structural basis for Ca(2+)-induced activation of human PAD4. *Nature Struct. Mol. Biol.* 2004, 11, 777-783.

38. Knuckley, B.; Luo, Y.; Thomson, P. R. Profiling protein arginine deiminase 4 (PAD4): A novel screen to identify PAD4 inhibitors. *Bioorg. Med. Chem.* 2008, 16(2), 739-745.

39. Luo, Y.; Knuckley, B.; Lee, Y. H.; Stallcup, M. R.; Thomson, P. R. A fluoroacetamidine-based inactivator of protein arginine deiminase 4: design, synthesis, and in vitro and in vivo evaluation. *J. Am. Chem. Soc.* 2006, 128, 1092-1093.

40. Bello, A. M.; Poduch, E.; Wei, L.; Moscarello, M.; Kotra, L. P. Interrogation of the active site of protein arginine deiminase (PAD) using designer probes. *ACS Med. Chem. Lett.* 2013, 4 (2), 249-253.

41. Ishigami, A. et al. Importance of research on peptidylarginine deiminase and citrullinated proteins in age-related disease. *Geriatr. Gerontol. Int.* 2010, 10 Suppl. 1, S53-S58.

42. Gould, R. M. et al. Messenger RNAs located in myelin sheath assembly sites. *J. Neurochem.* 2000, 75, 1834-1844.

43. Moscarello, M. A. et al. Peptidylarginine deiminase: a candidate factor in demyelinating disease. *J. Neurochem.* 2002, 81, 335-343.

44. Bartzokis, G. Age-related myelin breakdown: a developmental model of cognitive decline and Alzheimer's disease. *Neurobiol. Aging* 2004, 25, 5-18.

45. Tian, J. et al. Relationships between arteriosclerosis, cerebral amyloid angiopathy and myelin loss from cerebral cortical white matter in Alzheimer's disease. *Neuropathol. Appl. Neurobiol.* 2004, 30, 46-56.

46. Asaga, H. et al. Protein deimination in the rat brain: generation of citulline-containing proteins in cerebrum perfused with oxygen-deprived media. *Biomed. Res.* 2000, 21, 197-205.

47. Asaga, H. et al. Protein deimination in the rat brain after kainite administration: citulline-containing proteins as a novel marker of neurodegeneration. *Neurosci. Lett.* 2001, 299, 5-8.

48. Asaga, H. et al. Increased and type II specific expression of peptidylarginine deiminase in activated-microglia but not hyperplastic astrocytes following kainic acid-evoked neurodegeration in the rat brain. *Neurosci. Lett.* 2002, 326, 129-132.

49. Shimada, N. et al. Developmental and age-related changes of peptidylarginine deiminase 2 in the mouse brain. *J Neurosci. Res.* 2010, 88, 798-806.

50. Moscarello, M. A. et al. Inhibition of peptidyl-arginine deiminases reverses protein-hypercitrullination and disease in mouse models of multiple sclerosis. *Dis. Model. Mech.* 2013, 6, 467-478.

51. Wei, L. et al. Novel Inhibitors of Protein Arginine Deiminase with Potential Activity in Multiple Sclerosis Animal Model. *J. Med. Chem.* 2013, 56 (4), 1715-1722.

52. Acharya, N. K. et al. Neuronal PAD4 expression and protein citrullination: possible role in production of autoantibodies associated with neurodegenerative disease. *J. Autoimmun.* 2012, 38, 369-380.

53. Ishigami, A. et al. Abnormal accumulation of citullinated proteins catalyzed by peptidylarginine deiminase in hippocampal extracts from patients with Alzheimer's disease. *J. Neurosci. Res.* 2005, 80, 120-128.

54. Akiyama, K. et al. Localization of peptidylarginine deiminase type II in a stage-specific immature oligodendrocyte from rat cerebral hemisphere. *Neurosci. Lett.* 1999, 274, 53-55.

55. Lamensa J W E, Moscarello M A. Deimination of Human Myelin Basic Protein by a Peptidylarginine Deiminase from Bovine Brain. *J Neurochem* 1993; 61: 987-996

56. Sambandam T, Belousova M, Accaviti-Lope M A, Blanquicett C, Geurcello V, Raijmakers R, Nicholas A P. Increased peptidylarginine deiminase type II in hypoxic astrocytes. Biochem Biophys Res Commun 2004; 325: 1324-1329

57. Guerrin M, Ishigami A, Mechin M-C, Nachat R, Valmary S, Sebbag M, Simon M, Senshu T, Serre G. cDNA cloning, gene organization and expression analysis of human peptidylarginine deiminase type I. Biochem J. 2003, 370, 167-174.

58. Akiyama K, Inoue K, Senshu T. Immunocytochemical demonstration of skeletal muscle type peptidylarginine deiminase in various rat tissues. Cell Biol Int Rep 1990; 14: 267-273

59. Dekan, Z.; Vetter, I.; Daly, N. L.; Craik, D. J.; Lewis, R. J.; Alewood, P. F. alpha-Conotoxin ImI incorporating stable cystathionine bridges maintains full potency and identical three dimensional structure. *J. Am. Chem. Soc.* 2011, 133, 15866-15869.

60. Nakamura, T.; Noguchi, T.; Kobayashi, H.; Miyachi, H.; Hashimoto, Y. Mono- and dihydroxylated metabolites of thalidomide: synthesis and TNF-alpha production inhibitory activity. *Chem. Pharm. Bull.* (Tokyo) 2006, 54, 1709-1714.

We claim:

1. A compound of Formula I:

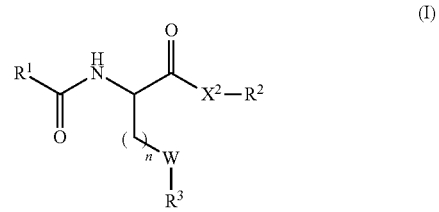

wherein:
R$^1$ is

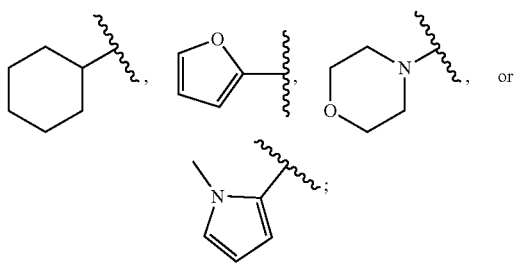

$X^2$ is O or NH;
$R^2$ is $CH_3$,
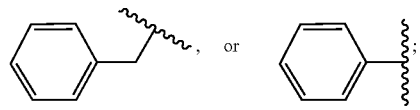 [SMILES: *Cc1ccccc1 ; *c1ccccc1]
n is 0 or 1;
$R^3$ is
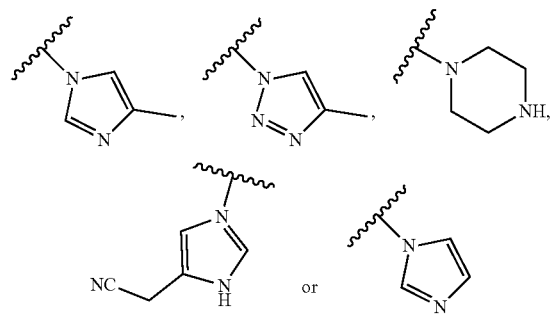
and
W is —$CH_2$- or —C(O);
or a pharmaceutically acceptable salt, solvate thereof, or stereoisomer thereof.
2. The compound of claim 1, wherein the compound of Formula I is:
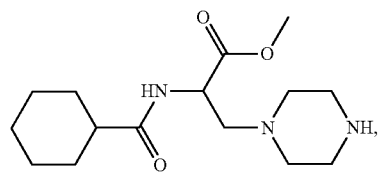
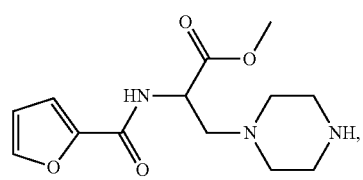
•2$CF_3$CHOOH
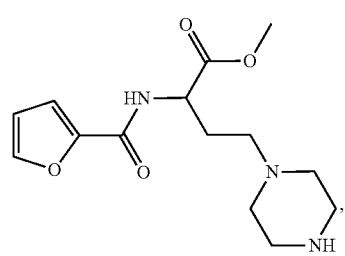
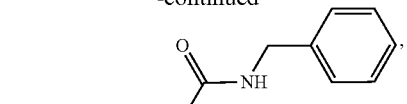
•2$CF_3$COOH
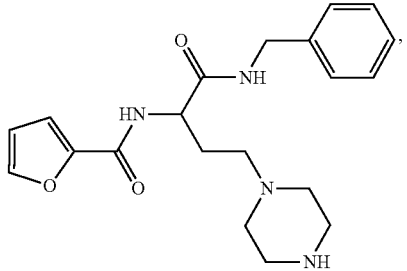
•2$CF_3$COOH
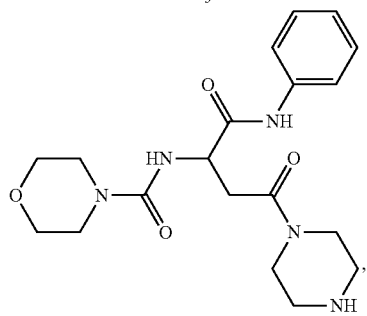
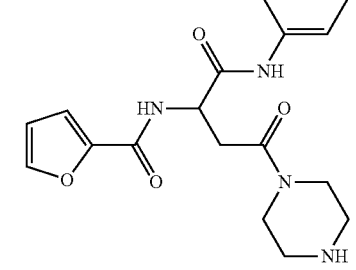
•2$CF_3$COOH
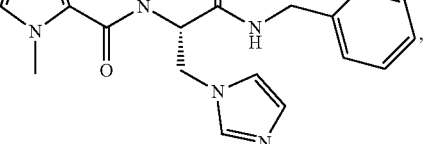
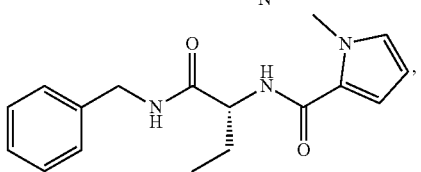
or -continued

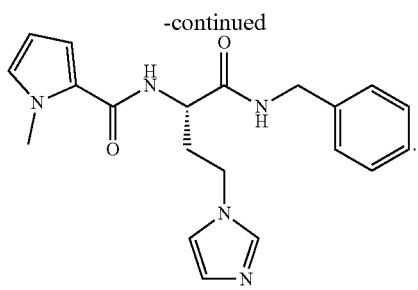

5

10

3. A pharmaceutical composition comprising one or more compounds of claim 1 and a pharmaceutically acceptable carrier.

4. A method for treating diseases, disorders or conditions characterized by or associated with the hypercitrullination of proteins by peptidyl arginine deiminase (PAD) enzymes comprising administering to a subject or patient, a therapeutically effective amount of one or more compounds of Formula I as defined in claim 1, wherein said subject or patient suffers from a disease, disorder or condition characterized by or associated with the hypercitrullination of proteins by peptidyl arginine deiminase (PAD) enzymes.

* * * * *